(12) United States Patent
Markovitz et al.

(10) Patent No.: US 7,691,582 B2
(45) Date of Patent: Apr. 6, 2010

(54) METHODS OF SECRETORY VIMENTIN DETECTION AND MODULATION

(75) Inventors: David M. Markovitz, Ann Arbor, MI (US); Nirit Mor-Vaknin, Ann Arbor, MI (US); Antonello Punturieri, Ann Arbor, MI (US)

(73) Assignee: The Regents of the University of Michigan, Ann Arbor, MI (US)

( * ) Notice: Subject to any disclaimer, the term of this patent is extended or adjusted under 35 U.S.C. 154(b) by 856 days.

(21) Appl. No.: 10/670,065

(22) Filed: Sep. 24, 2003

(65) Prior Publication Data

US 2004/0121419 A1    Jun. 24, 2004

Related U.S. Application Data

(60) Provisional application No. 60/414,210, filed on Sep. 27, 2002.

(51) Int. Cl.
*G01N 33/53* (2006.01)
(52) U.S. Cl. .................. 435/7.1; 435/7.2; 435/7.32; 435/325; 436/501; 424/130.1
(58) Field of Classification Search .................. 435/7.1, 435/7.2, 7.32, 325; 436/501; 424/130.1
See application file for complete search history.

(56) References Cited

U.S. PATENT DOCUMENTS

2002/0137110 A1    9/2002    Morishima et al.

FOREIGN PATENT DOCUMENTS

| DE | 1810423 | 10/1969 |
|---|---|---|
| WO | WO 98/39298 | 9/1998 |
| WO | WO 2005/012872 A2 | 2/2005 |

OTHER PUBLICATIONS

Steinberg et al. (Journal of Molecular and Cellular Cardiology, vol. 33, No. 6/01, p. A104).*
Yatsunami et al. (Biochemical and Biophysical Research Communications, 1991, vol. 177 No. 3, pp. 1165-1170).*
Rasmusen et al. (Environmental Health Perspectives, vol. 84, Mar. 1990, pp. 31-34).*
Vorgias et al. (Bioscience Reports, 1986, vol. 6, No. 1, pp. 57-64).*
Danskine et al. (Human Immunology, 2002, vol. 63, Supplement 1, pp. S30).*
Yang et al. (Clinical and Experimental Immunology, Apr. 2002, vol. 128, No. 1, pp. 169-174).*
Bohn et al. (Experimental Cell Research, vol. 201, No. 1, Jul. 1992, pp. 1-7) Abstract Only.*
Pallini et al. (Journal of Neuro-Oncology, vol. 49, 2000, pp. 9-17).*
See Blasi et al. (Clinical Pulmonary Medicine, Sep. 1, 2002, 6-12).*
Traub, P. Intermediate Filaments A Review, (Springer-Verlag, New York, Tokyo, 1985).
Fuchs, E. & Weber, K. Intermediate filaments: structure, dynamics, function, and disease. Annu Rev Biochem 63, 345-82 (1994).
Christian, J.L., Edelstein, N. G. & Moon, R.T. Overexpression of wild-type and dominant negative mutant vimentin subunits in developing Xenopus embryos. New Biol 2, 700-11. (1990).
Colucci-Guyon, E. et al. Mice lacking vimentin develop and reproduce without an obvious phenotype. Cell 79, 679-94. (1994).
Eckes, B. et al. Impaired mechanical stability, migration and contractile capacity in vimentin-deficient fibroblasts. J Cell Sci 111, 1897-907 (1998).
Galou, M. et al. Disrupted glial fibrillary acidic protein network in astrocytes from vimentin knockout mice. J Cell Biol 133, 853-63. (1996).
Eckes, B. et al. Impaired wound healing in embryonic and adult mice lacking vimentin. J Cell Sci 113, 2455-62 (2000).
Cain, H., Kraus, B., Krauspe, R., Osborn, M. & Weber, K. Vimentin filaments in peritoneal macrophages at various stages of differentiation and with altered function. Virchows Arch B Cell Pathol Incl Mol Pathol 42, 65-81 (1983).
Rius, C., Cabanas, C. & Aller, P. The induction of vimentin gene expression by sodium butyrate in human promonocytic leukemia U937 cells. Exp Cell Res 188, 129-34 (1990).
Rius, C. & Aller, P. Vimentin expression as a late event in the in vitro differentiation of human promonocytic cells. J Cell Sci 101, 395-401 (1992).
Reddy, V.Y., Zhang, Q.Y. & Weiss, S.J. Pericellular mobilization of the tissue-destructive cysteine proteinases, cathepsins B, L, and S, by human monocyte-derived macrophages. Proc Natl Acad Sci U S A 92, 3849-53 (1995).
Punturieri, A. et al. Regulation of Elastinolytic Cysteine Proteinase Activity in Normal and Cathepsin K-deficient Human Macrophages. J Exp Med 192, 789-800 (2000).
Cain, H., Krauspe, R. & Kraus, B. The cytoskeleton in activated and in functionally disordered cells of the macrophage system. Pathol Res Pract 175, 162-79 (1982).
Gao, Y. & Sztul, E. A novel interaction of the Golgi complex with the vimentin intermediate filament cytoskeleton. J Cell Biol 152, 877-94. (2001).
Traub, P. Large scale isolation, purification, and partial characterization of the intermediate filament-specific, Ca2 +-activated proteinase from porcine kidney and Ehrlich ascites tumor cells: a comparative study. Arch Biochem Biophys 228, 120-32. (1984).
Traub, P., Scherbarth, A., Willingale-Theune, J., Paulin-Levasseur, M. & Shoeman, R. Differential sensitivity of vimentin and nuclear lamins from Ehrlich ascites tumor cells toward Ca2+ -activated neutral thiol proteinase. Eur J Cell Biol 46, 478-90. (1988).
Yoshida, H., Murachi, T. & Tsukahara, I. Degradation of actin and vimentin by calpain II, a Ca2+-dependent cysteine proteinase, in bovine lens. FEBS Lett 170, 259-62. (1984).

(Continued)

*Primary Examiner*—Lisa V Cook
(74) *Attorney, Agent, or Firm*—Casimir Jones S.C.

(57) ABSTRACT

The present invention relates to methods for screening and modulating the bioavailability of extracellular secretory vimentin. In particular, the present invention provides inhibitors and activators of secretory vimentin including antibodies, small interfering RNAs, and antisense oligonucleotides. The present invention thus provides novel drug targets for enhanced anti-microbial response, and methods of using such modulators to beneficially alter the pathophysiologic effects of secretory vimentin.

9 Claims, 19 Drawing Sheets

OTHER PUBLICATIONS

Perides, G., Kuhn, S., Scherbarth, A. & Traub, P. Probing of the structural stability of vimentin and desmin-type intermediate filaments with 30 -activated proteinase, thrombin and lysine-specific endoproteinase Lys-C. Eur J Cell Biol 43, 450-8. (1987.

Tozser, J. et al. Effect of serine and tyrosine phosphorylation on retroviral proteinase substrates. Eur J Biochem 265, 423-9. (1999).

Ben-Ze'ev, A., Babiss, L.E. & Fisher, P.B. Cleavage of vimentin in dense cell cultures. Inhibition upon transformation by type 5 adenovirus. Exp Cell Res 166, 47-62. (1986).

Belin, M.T. & Boulanger, P. Processing of vimentin occurs during the early stages of adenovirus infection. J Virol 61, 2559-66. (1987).

Cheng, T.J. & Lai, Y.K. Identification of mitogen-activated protein kinase-activated protein kinase-2 as a vimentin kinase activated by odadaic acid in 9L rat brain tumor cells. J Cell Biochem 71, 169-81. (1998).

Turowski, P., Myles, T., Hemmings, B.A., Fernandez, A. & Lamb, N.J. Vimentin dephosphorylation by protein phosphatase 2A is modulated by the targeting subunit B55. Mol Biol Cell 10, 1997-2015 (1999).

Yasui, Y. et al. Protein kinases required for segregation of vimentin filaments in mitotic process. Oncogene 20, 2868-76. (2001).

Lo, C.-J., Fu, M. & Cryer, H.G. Interleukin 10 Inhibits Alveolar Macrophage Production of Inflammatory Mediators Involved in Adult Respiratory Distress Syndrome. Journal of Surgical Research 79, 179-184 (1998).

Bhattacharyya, S., Ghosh, S., Jhonson, P.L., Bhattacharya, S.K.-& Majumdar, S. Immunomodulatory Role of Interleukin-10 in Visceral Leishmaniasis: Defective Activation of Protein Kinase C-Mediated Signal Transduction Events. Infect. Immun. 69, 1499-1507 (2001).

Bogdan, C., Vodovotz, Y. & Nathan, C. Macrophage deactivation by interleukin 10. J Exp Med 174, 1549-55. (1991).

Schlosser-Silverman, E., Elgrably-Weiss, M., Rosenshine, I., Kohen, R. & Altuvia, S. Characterization of *Escherichia coli* DNA lesions generated within J774 macrophages. J Bacteriol 182, 5225-30 (2000).

Klymkowsky, M.W., Bachant, J.B. & Domingo, A. Functions of intermediate filaments. Cell Motil Cytoskeleton 14, 309-31 (1989).

Lehto, V.P., Hovi, T., Vartio, T., Badley, R.A. & Virtanen, I. Reorganization of cytoskeletal and contractile elements during transition of human monocytes into adherent macrophages. Lab Invest 47, 391-9 (1982).

Owen, P.J., Johnson, G.D. & Lord, J.M. Protein kinase C-delta associates with vimentin intermediate filaments in differentiated HL60 cells. Exp Cell Res 225, 366-73 (1996).

Chu, J.J. et al. Taxol induces concomitant hyperphosphorylation and reorganization of vimentin intermediate filaments in 9L rat brain tumor cells. J Cell Biochem 68, 472-83. (1998).

Szalay, J. et al. Associations of PKC isoforms with the cytoskeleton of B16F10 melanoma cells. J Histochem Cytochem 49, 49-66. (2001).

Shoeman, R.L. et al. Human immunodeficiency virus type 1 protease cleaves the intermediate filament proteins vimentin, desmin, and glial fibrillary acidic protein. Proc Natl Acad Sci U S A 87, 6336-40. (1990).

Kontny, E., Kurowska, M., Szczepanska, K. & Maslinski, W. Rottlerin, a PKC isozyme-selective inhibitor, affects signaling events and cytokine production in human monocytes, J Leukoc Biol 67, 249-58. (2000).

Hansson, G.K., Lagerstedt, E., Bengtsson, A. & Heideman, M. IgG binding to cytoskeletal intermediate filaments activates the complement cascade. Exp Cell Res 170, 338-50 (1987).

Sanchez, A. Ossorio, C., Alvaro-Gracia, J.M., Padilla, R. & Avila, J. A subset of antibodies from the sera of patients with systemic lupus erythematosus react with vimentin and DNA. J Rheumatol 17, 205-9 (1990).

Senecal, J.L. & Rauch, J. Hybridoma lupus autoantibodies can bind major cytoskeletal filaments in the absence of DNA-binding activity. Arthritis Rheum 31, 864-75 (1988).

Franch, A., Castellote, C., Vila, J.L., Vilaro, S. & Castell, M. Anticytoskeletal autoantibody development in adjuvant arthritis. J Rheumatol 21, 489-97 (1994).

Lane, B.R. et al. TNF-alpha inhibits HIV-1 replication in peripheral blood monocytes and alveolar macrophages by inducing the production of RANTES and decreasing C-C chemokine receptor 5 (CCR5) expression. J Immunol 163, 3653-61 (1999).

Terasaki, M. & Reese, T.S. Characterization of endoplasmic reticulum by co-localization of BiP and dicarbocyanine dyes. J Cell Sci 101, 315-22. (1992).

Matsukawa, A. et al. Pivotal role of the CC chemokine, macrophage-derived chemokine, in the innate immune response. J Immunol 164, 5362-8 (2000).

Cherry et al., Enzyme-Linked Fluorescent Detection for Automated Multiplex DNA Sequencing, Genomics 20, 68074 (1994).

Schmitt et al., Expression of Gene 1.2 and Gene 10 of Bacteriophage T7 Is Lethal to F Plasmid-Containing *Escherichia coli*, J of Bacteriology 173, 1536-1543 (1991).

Slilaty et al., Accurate insertional inactivation of lacZa: construction of pTrueBlue and M13TrueBlue cloning vectors, Gene 213, 83-91 (1998).

Henrich et al., Use of the I ysis gene of bacteriophage oX174 for the contruction of a positive selection vector, Gene 42, 345-349 (1986).

Viera et al., The pUC plasmids, anM13mp7-derived system for insertion mutagenesis and sequencing with synthetic universal primers, Gene 19, 259-268 (1982).

Quandt et al., Versatile suicide vectors which allow direct selection for gene replacement in Gram-negative bacteria, Gene 127, 15-21 (1993).

Wiemann et al., Simultaneous On-Line DNA Sequencing on Both Strands with Two Fluorescent Dyes, Analytical Biochemistry 224, 117-121 (1995).

Bernard et al., Positive-selection vectors using the F plasmid ccdB killer gene, Gene 148, 71-74 (1994).

Dillard et al., Analysis of *Strepococcus pneumoniae* sequences Cloned into *Escherichia coli*: Effect of Promoter Strength and Transcription Terminators, J of Bacteriology 173, 5105-5109 (1991).

Geider et al., A plasmid cloning system utilizing replication and packaging functions of the filamentous bacterio-phage fd, Gene 33, 341-349 (1985).

Smith et al., fluorescence detection in automated DNA sequence analysis, Nature 321, 674-679 (1986).

Reynolds et al., Parameters Affecting Transcription Termination by *Escherichia coli* RNA Polymerase, J Mol Biol 224, 31-51 (1992).

Hoffmann-Berling, Virology 22, 305-313 (1964).

Church et al., Multiplex DNA Sequencing, Science 240, 185-188 (1988).

Prober et al., A System for Rapid DNA Sequencing with Fluorescent Chain-Terminating Dideoxynucleotides, Science 238, 336-341 (1987).

Wiemann et al., "Doublex" Fluorescent DNA Sequencing: Two Independent Sequences Obtained Simultaneously in One Reaction with Internal Labeling and Unlabeled Primers, Analytical Biochemistry 234, 166-174 (1996).

Egholm et al., PNA hybridizes to complementary oligonucleotides obeying the Watson-Crick hydrogen-bonding rules, Nature 365, 566-568 (1993).

Sanger et a., DNA sequencing with chain-terminating inhibitors, PNAS 74, 5463-5467 (1977).

Lipman et al., A tool for multiple sequence alignment, PNAS 86, 4412-4415 (1989).

Fitzgerald et al., Rapid shotgun cloning utilizing the two base recognition endonucleases CviJ1, Nucleic Acids Research 20, 3753-3762 (1992).

Rose, Nucleic Acids Research 16, 355 (1988).

Tabor et al., A single residue in DNA polymerases of the *Escherichia coli* DNA polymerase I family is critical for distinguishing between deoxy-and dideoxyribonucleotides, PNAS 92, 6339-6343 (1995).

Chen et al., Cloning of *Streptococcus pneumoniae* DNA fragments in *Escherichia coli* requires vectors protected by strong transcriptional terminatores. Gene 55, 179-187 (1987).

Bolivar et al., Construction and Characterization of New Cloning Vehicles, Gene 2, 95-113 (1977).

Liu et al., An Efficient Method for Blunt-End Ligation of PCR Products, Biotechniques 12, 28-29 (1992).

Creasey et al., Application of a Novel Chemiluminescence-Based DNA Detection Method to Single-Vector and Multiplex DNA Sequencing, BioTechniques 11, 102-109 (1991).

Neurath et al., Antibodies to Interleukin 12 Abrogate Established Experimental Colitis in Mice, J of Ex Med 182, 1281-1290 (1995).

Chen et al., Construction and properties of a new insertion vector, pJDC9, that is protected by transcriptional terminators and useful for cloning of DNA from *Streptococcus pneumoniae*, Gene 64, 155-164 (1988).

Podor et al., Vimentin Exposed on Activated Platelets and Platelet Microparticles Localizes Vitrenectin and Plasminogen Activator Inhibitor Complexes on Their Surface, J. Biol Chem 277(9):7529 (2002).

Perides et al., Electrostatic and hydrophobic interactions of the intermediate filament protein vimentin and its amino terminus with lipid bilayers, J Biol Chem 262:13742-13749 (1987).

Nishimura et al., A di-acidic signal required for selective export from the endoplasmic reticulum, Science 277:556-559 (1997).

Nishimura et al., A di-acidic (DXE) code directs concentration of cargo during export from the endoplasmic reticulum, J Biol Chem274:15937-15946 (1999).

Hansson et al., Fc-mediated binding of IgG to vimentin-type intermediate filaments in vascular endothelial cells, PNAS USA 81:3103-3107 (1984).

Traub P. et al., "Salt-stable interaction of the amino-terminal head region of vimentin with the alpha-helical rod domain of cytoplasmic intermediate filament proteins and its relevance to protofilament structure and filament formation and stability" Journal of Cell Science, 1992, 363-381, vol. 101, No. 2 (ISSN 0021-9533).

Mor-Vaknin et al., "Vimentin is secreted by activated macrophages" Nature Cell Biology, Jan. 2003, 59-63, vol. 5 (Abstract Only).

\* cited by examiner

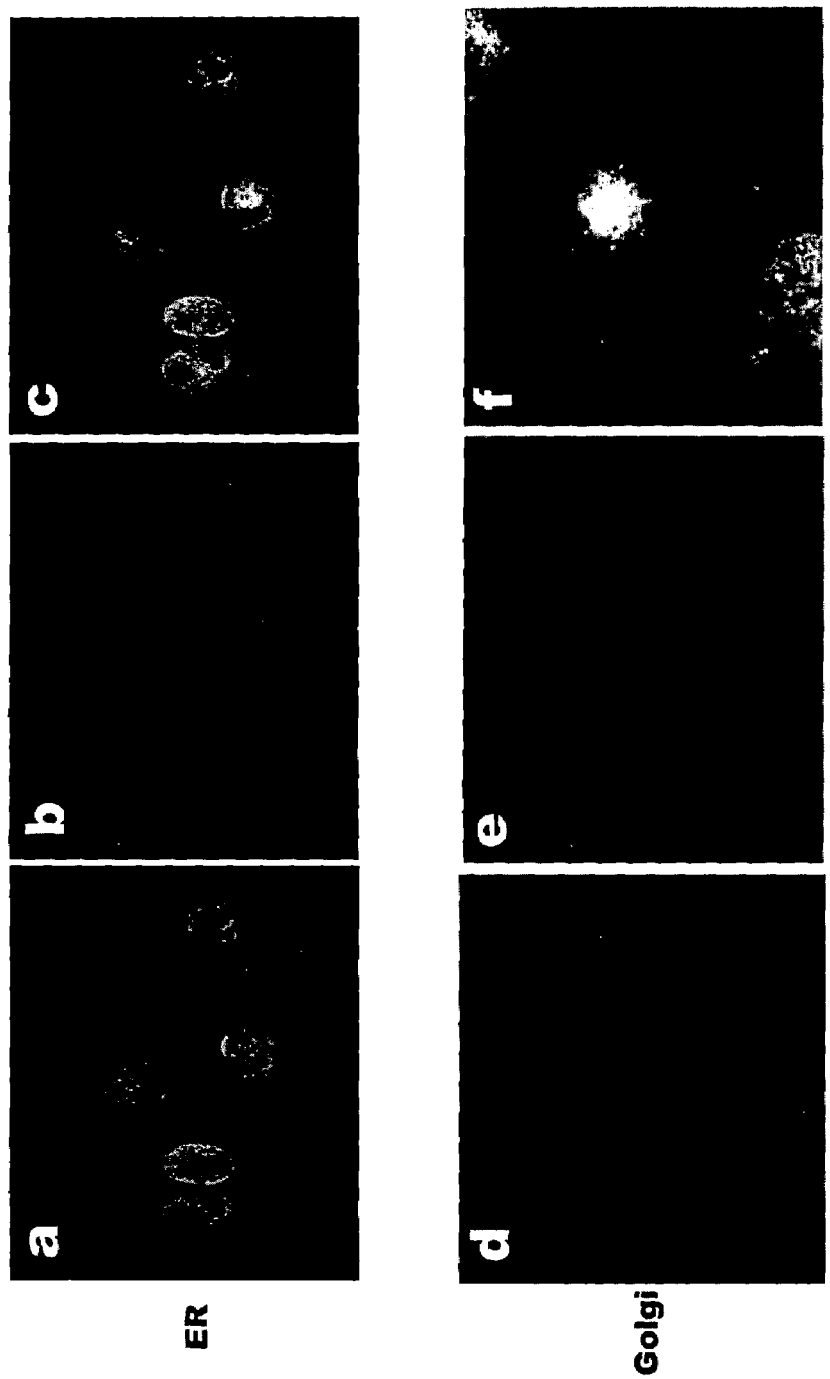

10 day 40%

7 day 10%

7A

7B

METHODS OF SECRETORY VIMENTIN DETECTION AND MODULATION

The present invention claims priority to U.S. Provisional Application, Ser. No. 60/414,210, filed Sep. 27, 2002, the disclosure of which is hereby incorporated by reference in its entirety.

This invention was made with government support grant number AR48310 awarded by the National Institute of health. The government has certain rights in the invention.

FIELD OF THE INVENTION

The present invention relates to methods for screening and modulating the bioavailability of extracellular secretory vimentin. In particular, the present invention provides inhibitors and activators of secretory vimentin including antibodies, small interfering RNAs, and antisense oligonucleotides. The present invention thus provides novel drug targets for enhanced anti-microbial response, and methods of using such modulators to beneficially alter the pathophysiologic effects of secretory vimentin.

BACKGROUND OF THE INVENTION

Vimentin is is highly expressed in cells of mesenchymal origin, as well as in most transformed cell lines and tumors. Like other intermediate filament (IF) proteins, intracellular vimentin is important for stabilizing the architecture of the cytoplasm, and contributes to specific dynamic cellular process such as mechanical stability, migration and wound healing.[5,6,7]

Vimentin is abundant in human monocytes, activated macrophages and in multinucleated giant cells.[8] Increased vimentin expression is a late event in the differentiation of human monocytic cells.[9,10] Human monocytes cultured in 40% human serum differentiate into monocyte-derived macrophages (MDM). These cells take on the characteristics of in vivo activated tissue macrophages, becoming multi-nucleated, and secreting proteases that destroy connective tissue elements.[11,12] Prior to the present disclosure, extracellular secretion of vimentin and its role in inflammation and anti-pathogen activity was unrecognized. Thus, effective methods of screening for the contribution of secreted vimentin to physiologic or pathologic pathways are clearly needed, as are modulators of vimentin bioavailability for use in the treatment of secretory vimentin-mediated pathologies.

SUMMARY OF THE INVENTION

The present invention relates to methods for screening and modulating the bioavailability of extracellular secretory vimentin. In particular, the present invention provides inhibitors and activators of secretory vimentin including antibodies, small interfering RNAs, and antisense oligonucleotides. The present invention thus provides novel drug targets for enhanced anti-microbial response, and methods of using such modulators to beneficially alter the pathophysiologic effects of secretory vimentin.

Accordingly, in some embodiments the present invention provides a method for screening the capacity of compounds to alter the activity of secretory vimentin, comprising: providing a first polypeptide comprising at least a portion of vimentin; a second polypeptide comprising at least a portion of a protein known to interact with vimentin; and one or more test compounds; and combining the portion of vimentin, the second polypeptide and the test compound under such conditions that the first polypeptide, second polypeptide and test compound interact, such that the test compound inhibits or activates the interaction action between the said polypeptide sequence comprising at least a portion of secretory vimentin and said polypeptide sequence comprising at least a portion of a protein known to interact with vimentin. In some embodiments the first polypeptide is selected from a group including, but not limited to, secretory vimentin, vimentin fragments, vimentin byproducts, and vimentin metabolites. In some preferred embodiments the second polypeptide is a monoclonal antibody. In further embodiments the test compound inhibits the binding of vimentin to a monoclonal antibody. In other embodiments the second polypeptide is a polyclonal antibody. In further embodiments the test compound inhibits the binding of vimentin to a polyclonal antibody. In some embodiments vimentin is secreted from a cell of mesenchymal origin. In further embodiments vimentin is secreted from a monocyte. In some embodiments vimentin is secreted from a monocyte-derived macrophage. In other embodiments secretory vimentin is bound to a cell of its origin. In yet other embodiments secretory vimentin is unbound. In still further embodiments secretory vimentin is bound to a cell other than its cell of origin.

The present invention also provides a method for pathogen killing comprising: providing a pathogen; and one or more test compounds that decrease the bioavailability of secretory vimentin; and combining in any order the pathogen and said one or more compounds under conditions such that said pathogen is exposed to a decreased amount of bioavailable secretory vimentin. In some embodiments the pathogen is bacterial. In some embodiments the compound decreases vimentin secretion. In another embodiment, the compound increases vimentin metabolism. In one embodiment the compound comprises an antisense oligonucleotide. In a preferred embodiment the compound comprises siRNA. In other embodiments the compound inhibits extracellular bioavailability of secretory vimentin. In a preferred embodiment the compound comprises a monoclonal antibody. In other embodiments the compound comprises a polyclonal antibody. In further embodiments the compound is a small molecule. In still further embodiments the compound comprises a secretory vimentin antagonist. In preferred embodiments the compound is a neutral thiol proteinase.

DESCRIPTION OF THE FIGURES

FIG. 3 shows the time course and specificity of vimentin secretion by 12 day MDM. A pulse-chase analysis of 12 day MDM was performed to analyze vimentin secretion with time. After a 12 h labeling of 10 day MDM with $^{35}$S-methionine (pulse), the supernatant was collected at the indicated times (chase). The supernatants were immunoprecipitated with anti-vimentin or anti-actin antibodies (3a); the quantitation of vimentin in the supernatants and cell fractions as assessed by densitometry is shown in FIG. 3b. In FIG. 3e, 11 day MDM were incubated with the cysteine proteinase inhibitor E-64 and vimentin was detected by Western blot analysis using V9 monoclonal antibody.

GENERAL DESCRIPTION OF THE INVENTION

The present invention relates to methods for screening and modulating the bioavailability of extracellular secretory vimentin. In particular, the present invention provides inhibitors and activators of secretory vimentin including antibodies, small interfering RNAs, and antisense oligonucleotides. The present invention thus provides novel drug targets for enhanced anti-microbial response, and methods of using such modulators to beneficially alter the pathophysiologic effects of secretory vimentin.

Central to the present disclosure is the discovery that vimentin, previously regarded exclusively as an intracellular protein, is secreted, and that secretory vimentin plays a role in the ability of MDM to kill bacteria, and in inflammation. Activated human macrophages secrete vimentin into the extracellular space using the classical Golgi pathway. Western blot, immunoprecipitation, and direct protein sequencing demonstrate the presence of vimentin in the supernatants of mature MDM. Cellular mortality does not account for the extracellular presence of vimentin, since the presence of the cytoskeletal protein β-tubulin cannot be detected in the supernatants, and only trace amounts of the highly abundant cytoskeletal actin protein are simultaneously detected. This shows that intracellular proteins other than vimentin do not non-specifically leak into the supernatants.

Figure 4:
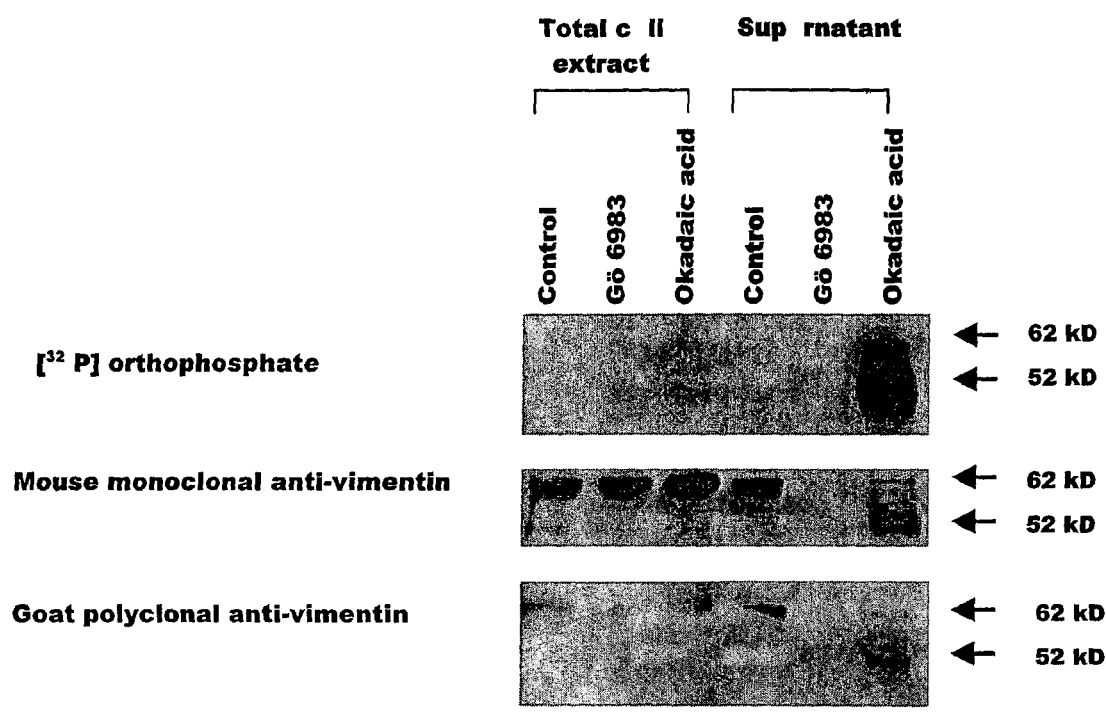
FIG. 4 shows that the PKC pathway phosphorylates vimentin; secretion is enhanced by the phosphatase inhibitor okadaic acid (OA) and blocked by the PKC inhibitor GÖ 6983. (a) 10 day MDM cultured in 40% serum were incubated for 2 h with GÖ 6983 [250 nM], the p38 mitogen activated protein kinase inhibitor SB 203580 [100 μM], or okadaic acid [100 nM], and the supernatant analyzed by anti-vimentin Western blot. (b) 7 day MDM cultured in 10% serum were incubated with okadaic acid [100 nM] for 2 h, or preincubated with GÖ 6983 [250 nM] for 2 h prior to OA treatment. The supernatant was analyzed as in FIG. 4a. (c) Total cell extracts or supernatants from 10 day MDM cultured in 40% serum were immunoprecipitated with a specific polyclonal anti-phospho-(Ser/Thr) antibody and vimentin was detected by the V9 monoclonal anti-vimentin antibody. Total vimentin was also detected with anti-vimentin V9 antibody in cell extract and supernatant before the immunoprecipitation (WB only lanes). (d) 7 day MDM cultured in 10% serum were incubated with okadaic acid [100 nM] for 2 h, or incubated with GÖ 6983 [250 nM] for 2 h. Proteins were immunoprecipitated from either cellular extracts or supernatants with a polyclonal anti-phospho-(Ser/Thr) antibody and vimentin was detected as in c. In (e), [$^{32}$P]-labeled vimentin was immunoprecipitated from 12 day MDM using V9 vimentin monoclonal antibody (conjugated to agarose beads) after incorporation of [$^{32}$P]orthophosphate in the absence (control) or the presence of GÖ 6983 [250 nM] or okadaic acid [100 nM]. The same membrane was also probed for vimentin using both the monoclonal (middle panel) and goat polyclonal (bottom panel) anti-vimentin antibodies.

The secretion of vimentin is a specific, active process, consistent with previously published studies that examined secretion of other proteins from activated MDM[12]. Experiments conducted during the development of the present invention have found that monensin and tunicamycin are able to block the secretion of vimentin, showing that it is an active rather than passive process that works through the Golgi, in accord with immunohistochemical results. It is further demonstrated that the secretion of vimentin is enhanced by the phosphatase inhibitor OA, and blocked by the specific PKC inhibitor GÖ46983, directly implicating the PKC pathway in the secretion of vimentin. The findings using in-vivo incorporation of [$^{32}$P] orthophosphate (FIG. 4) indicate that the secreted vimentin is phosphorylated at serine and threonine residues, and implicate PKC in the secretion process of vimentin.

The organization and stability of vimentin filaments is regulated by proteases[15,16,20]. Experiments conducted during the development of the present invention show that the cysteine proteinase inhibitor E-64 changes the pattern of intracellular and extracellular vimentin as detected by Western blot.

Experiments conducted during the development of the present invention also show that the anti-inflammatory cytokine Interleukin-10 (IL-10), which has been found to exert its effect on macrophages by inhibiting the PKC pathway, blocks vimentin secretion. In addition, the pro-inflammatory cytokine tumor necrosis factor-alpha triggers vimentin secretion that cannot be blocked by the PKC blocker GÖ6983. A role for individual PKC isoenzymes in the induction of pro-inflammatory cytokine synthesis, including that of TNF-α has been identified (35). IL-10 potently suppresses many effector functions of monocytes and macrophages, including the release of cytokines such as TNF-α[27]. Thus, an amplification cascade in which stimulation of the PKC pathway triggers secretion of vimentin as well as production of TNF-α, which then activates others pathways leading to vimentin secretion is initiated. When anti-inflammatory agents such as IL-10 inhibit PKC signaling, vimentin secretion is then reduced directly, as well as in response to the accompanying reduction in the level of TNF-α.

Figure 6A:
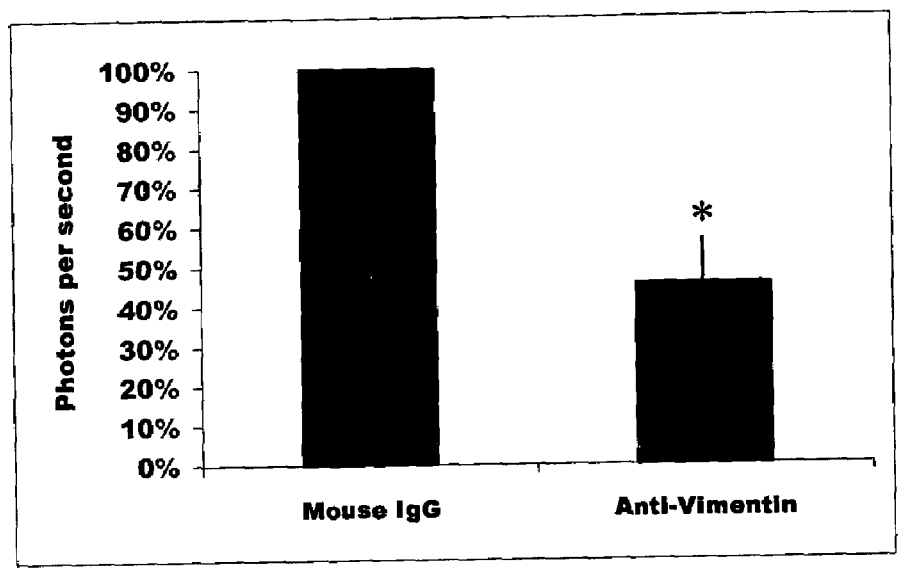
FIG. 6 shows that antibodies to vimentin inhibit the killing of E. coli by MDM. (a). 12 day MDM preincubated overnight with 180 μg ml$^{-1}$ of anti-vimentin produce lower levels of oxidative metabolites than cells treated with control mouse IgG. The results shown represent the mean of four experiments, with the asterisk indicating p=0.003 as measured by Student's t-test. (b). Ten day MDM preincubated overnight with 180 μg ml$^{-1}$ of anti-vimentin or the same concentration of mouse IgG, and challenged with 10$^6$ colony-forming units (CFU) E. coli, do not differ in their ability to phagocytose bacteria. (c) When cells from (b) are given an additional 2 h after phagocytosis for intracellular processing, anti-vimentin treated MDM show a significant impairment in bacterial killing. Data shown in (b) and (c) represent the mean of four independent experiments. The p value (asterisk) in (c) is 0.043, as measured by Student's t-test.
Figure 6B:
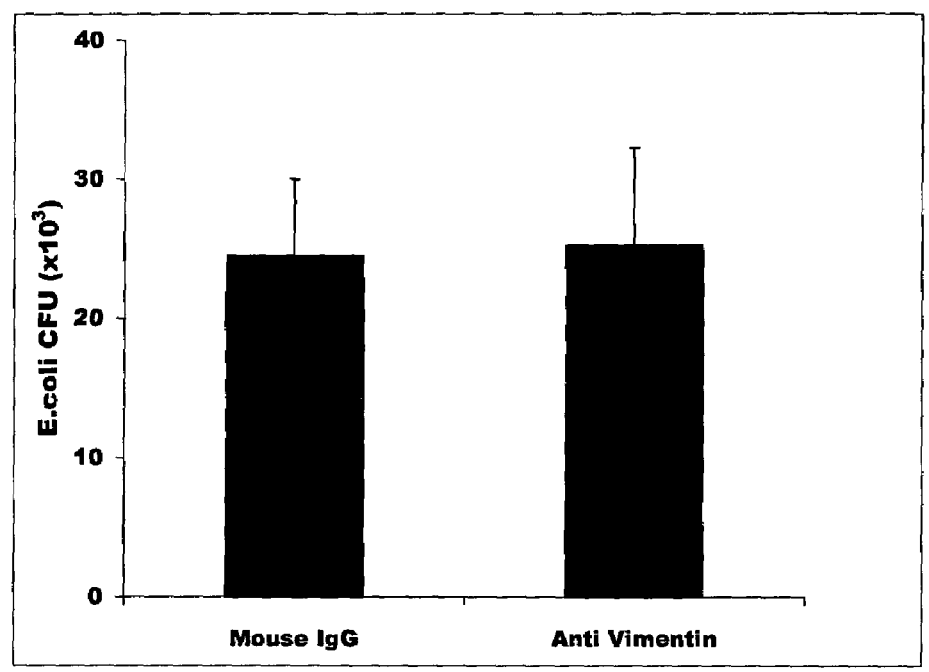
Figure 6C:
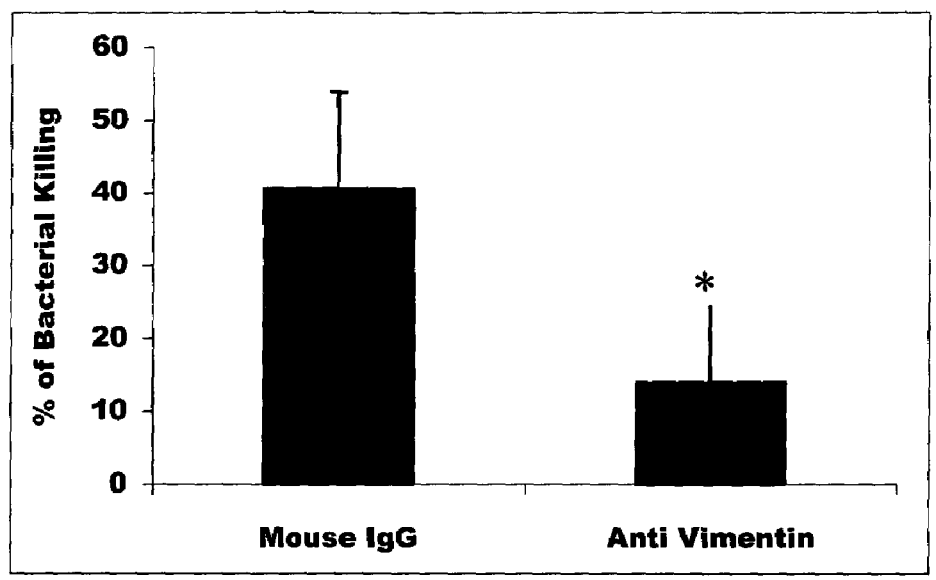
Figure 7:
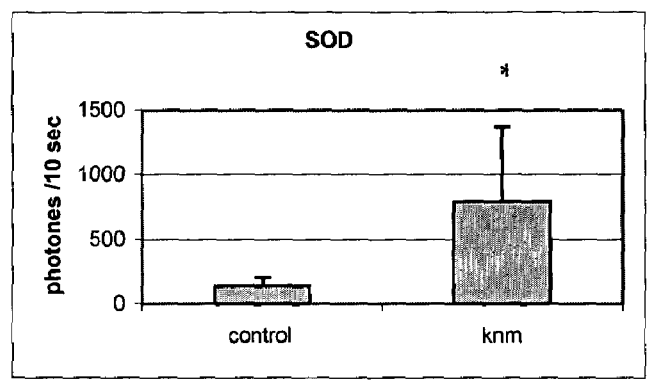
FIG. 7 shows increased superoxide production by peritoneal macrophages from vimentin knockout mice compared to wild-type mice. In (a) resident peritoneal macrophages were harvested from mice (total of 8 mice from each group). Cells were incubated with 50 μM luminol and 100 nM PMA for 5 min at 37° C. Light emission was measured by Chemiluminescence Microlumat LB 96 P (EG&G Berthold). The data shown here are an average of three different experiments. *p value=0.018. In (b) shows increased nitric oxide production by peritoneal macrophages from vimentin knockout mice compared to wild-type mice. Peritoneal macrophages in 10% F.C.S were incubated for 48 h with IFN γ 50 ng/ml and LPS 1000 ng/m. The media were collected and analyzed for the presence of NO by Griess reagent. Four wild-type and five knockout mice were used in these experiments. *p value=0.057.
Figure 7:
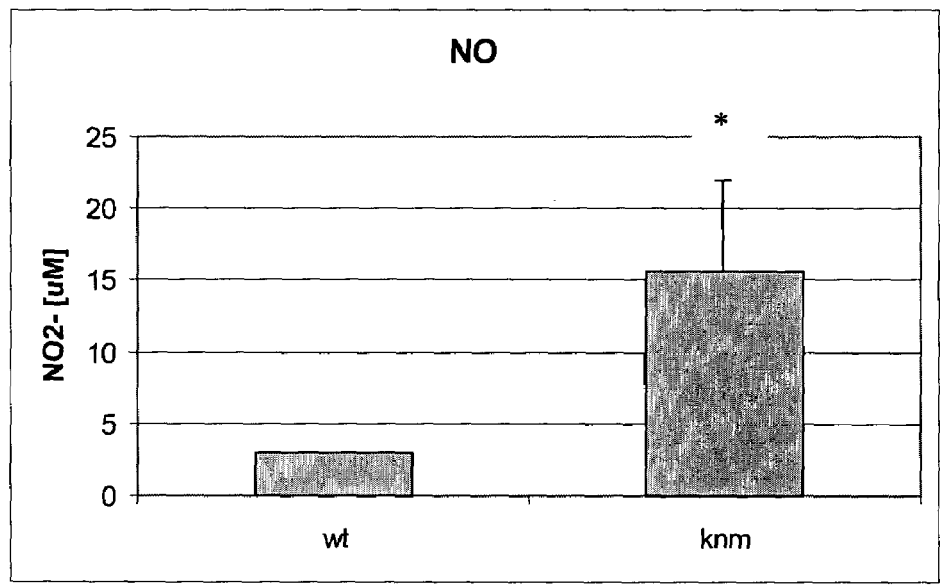

Finally, secretory vimentin is involved in the generation of oxidative metabolites and bacterial killing, two important functions of activated macrophages. Treatment of mature MDM with antibodies to vimentin decreases the oxidative burst (FIG. 6a) and bactericidal activity against E. coli (FIG. 6c). As well, superoxide and nitric oxide production is increased in the peritoneal macrophages of vimentin knockout compared to wild-type mice (FIGS. 7a and 7b). Thus, extracellular vimentin is necessary for specific components of the response of MDM to pathogens. These data establish that vimentin, an intermediate filament that until now has been studied exclusively as an intracellular protein, is secreted by macrophages in response to PKC as well as other signaling pathways, and thereby plays an important role in immune function. Complement factors bind to intracellular vimentin exposed during cell injury (36). The present discovery of secretory vimentin introduces a greater degree of specificity to the process than simple compromise of membrane integrity.

Autoantibodies to vimentin occur in chronic inflammatory and infectious conditions such as rheumatoid arthritis, leprosy, mononucleosis, and cytomegalovirus infections[1,37-39]. Prior to the present disclosure it was assumed that the appearance of autoantibodies to vimentin resulted from cellular destruction and subsequent leakage of cytoplasmic contents. To the contrary, active secretion of vimentin explains the origin of autoantibodies to vimentin in these and related conditions, providing novel and specific opportunities for drug development and therapeutic intervention.

Definitions

To facilitate an understanding of the present invention, a number of terms and phrases are defined below:

As used herein, the terms "vimentin" and "vimentin-related proteins" refer to intermediate filament proteins highly expressed in cells of mesenchymal origin, as well as in transformed cell lines, tumors and cells of distinct embryonic origin.

As used herein, the terms "vimentin fragments, byproducts, or metabolites" refer to any fragments (e.g., truncations) or chemical variants (e.g., enzymatic modifications that add or remove one or more chemical constituents) of vimentin. The terms include both naturally occurring fragments, byproducts, and metabolites, as well as, artificially generated fragments, byproducts, or metabolites.

As used herein, the term "secretion," when used in conjunction with extracellular molecules (e.g., proteins), refers to the process of moving or transporting a molecule from an intracellular location (e.g., cytoplasm) to an extracellular location (e.g., extracellular surface of plasma membrane or free extracellular space). Secretion includes, but is not limited to such natural cellular processes as secretion through the Golgi and endoplasmic reticulum, secretion through pores or channels, and secretion through flipping across a cellular membrane. Secretion does not include extracellular movement of molecules due to destruction or damage to a cell (e.g., cellular necrosis). Secreted molecules can be "bound" to a cell, which means that the molecules are affixed to the cell through covalent or non-covalent chemical interactions. Secreted molecules can also be "unbound," which means that the molecules are not fixed to the surface of a cell, but are free to move in the extracellular environment (e.g., move to a region of the extracellular environment of a different cell).

As used herein, the term "bioavailable" refers to molecules that are present in a form that allows them to exhibit a biological activity in the presence of a different target molecule. For example, a protein is bioavailable when it is presented to a target molecule (e.g., a receptor) so as to change the chemical activity or behavior of the target molecule. Bioavailable extracellular vimentin is considered bioavailable when in a form that exhibits a biological activity in the extracellular space (e.g., an effect on microbial killing or inflammation). Vimentin may be considered not bioavailable for such uses where, for example, the vimentin is located intracellularly.

As used herein, the term "small molecule" refers to any non-polymeric, biologically active chemical entity.

As used herein, the term "pathogen" refers to a specific causative agent of infectious disease. A pathogen may be, for example, bacteria, fungi, virus, protozoa, or a multicellular parasite.

As used herein, the term "inflammation" refers to a response to cellular injury characterized by one or more signs and symptoms of capillary dilatation, leukocyte infiltration, erythema, heat, pain, swelling and loss of function.

As used herein, the term "mesenchymal" refers to loosely organized undifferentiated mesodermal cells that give rise to such structures as connective tissues, vascular constituents, lymphatics, bone, and cartilage.

As used herein, the term "monocyte" refers to a white blood cell with finely granulated chromatin dispersed throughout the nucleus that is formed in the bone marrow, enters the blood, and migrates into the connective tissue where it is capable of differentiation into a macrophage.

As used herein, the term "macrophage" refers to a phagocytic tissue cell of the mononuclear phagocyte system that may be fixed or freely motile, is derived from a monocyte, and functions in the protection of the body against infection and noxious substances.

As used herein, the term "metabolism" refers to the sum of the processes by which a substance is handled (as by assimilation and incorporation, or by detoxification and excretion) in the living body.

As used herein, the term "proteinase inhibitor" refers to any compound or compounds that inhibit the activity of enzymes or other molecules that degrade or destroy proteins.

As used herein, the term "subject" refers to any animal (e.g., a mammal), including, but not limited to, humans, non-human primates, rodents, and the like, which is to be the recipient of a particular treatment. Typically, the terms "subject" and "patient" are used interchangeably herein in reference to a human subject.

As used herein, the term "non-human animals" refers to all non-human animals including, but are not limited to, vertebrates such as rodents, non-human primates, ovines, bovines, ruminants, lagomorphs, porcines, caprines, equines, canines, felines, etc.

As used herein, the term "sample" is used in its broadest sense. In one sense, it is meant to include a specimen or culture obtained from any source, as well as biological and environmental samples. Biological samples may be obtained from animals (including humans) and encompass fluids, solids, tissues, and gases. Biological samples include blood products, such as plasma, serum and the like. Environmental samples include environmental material such as surface matter, soil, water, crystals and industrial samples. Such examples are not however to be construed as limiting the sample types applicable to the present invention.

As used herein, the term "host cell" refers to any cell (e.g., mammalian cells, avian cells, amphibian cells, plant cells, fish cells, and insect cells), whether located in vitro or in vivo.

As used herein, the term "contacting said test compound and said peptide under conditions such that the ability of said test compound to inhibit the binding of said peptide to said vimentin protein is determined" refers to the measurement of the ability of test compounds to compete for binding to vimentin protein in the presence of an peptide inhibitor of the present invention. The binding may be determined using any suitable method. For example, in some embodiments, binding is determined by labeling the peptide inhibitor and determining the amount of peptide inhbitor bound in the presence and absence of the test compound.

As used herein, the term "competes for binding" is used in reference to a first polypeptide with an activity which binds to the same substrate as does a second polypeptide with an activity, where the second polypeptide is a variant of the first polypeptide or a related or dissimilar polypeptide. The efficiency (e.g., kinetics or thermodynamics) of binding by the first polypeptide may be the same as or greater than or less than the efficiency substrate binding by the second polypeptide. For example, the equilibrium binding constant ($K_D$) for binding to the substrate may be different for the two polypeptides. The term "$K_M$" as used herein refers to the Michaelis-Menton constant for an enzyme and is defined as the concentration of the specific substrate at which a given enzyme yields one-half its maximum velocity in an enzyme catalyzed reaction.

As used herein, the term "response" when used in reference to an assay, refers to the generation of a detectable signal (e.g., accumulation of reporter protein, increase in ion concentration, accumulation of a detectable chemical product).

The term "test compound" refers to any chemical entity, pharmaceutical, drug, and the like that can be used to treat or prevent a disease, illness, sickness, or disorder of bodily function, or otherwise alter the physiological or cellular status of a sample. Test compounds comprise both known and potential therapeutic compounds. A test compound can be determined to be therapeutic by screening using the screening methods of the present invention. A "known therapeutic compound" refers to a therapeutic compound that has been shown (e.g., through animal trials or prior experience with administration to humans) to be effective in such treatment or prevention. In some embodiments of the present invention, test compounds include antisense compounds.

As used herein, the term "cell culture" refers to any in vitro culture of cells. Included within this term are continuous cell lines (e.g., with an immortal phenotype), primary cell cultures, finite cell lines (e.g., non-transformed cells), and any other cell population maintained in vitro, including oocytes and embryos.

As used herein, the term "in vitro" refers to an artificial environment and to processes or reactions that occur within an artificial environment. In vitro environments can consist of, but are not limited to, test tubes and cell culture. The term "in vivo" refers to the natural environment (e.g., an animal or a cell) and to processes or reaction that occur within a natural environment.

As used herein, the term "protein kinase" refers to proteins that catalyze the addition of a phosphate group from a nucleoside triphosphate to an amino acid side chain in a protein. Kinases comprise the largest known enzyme superfamily and vary widely in their target proteins. Kinases may be categorized as protein tyrosine kinases (PTKs), which phosphorylate tyrosine residues, and protein serine/threonine kinases (STKs), which phosphorylate serine and/or threonine residues. Some kinases have dual specificity for both serine/threonine and tyrosine residues. Almost all kinases contain a conserved 250-300 amino acid catalytic domain. This domain can be further divided into 11 subdomains. N-terminal subdomains I-IV fold into a two-lobed structure that binds and orients the ATP donor molecule, and subdomain V spans the two lobes. C-terminal subdomains VI-XI bind the protein substrate and transfer the gamma phosphate from ATP to the hydroxyl group of a serine, threonine, or tyrosine residue. Each of the 11 subdomains contains specific catalytic residues or amino acid motifs characteristic of that subdomain. For example, subdomain I contains an 8-amino acid glycine-rich ATP binding consensus motif, subdomain II contains a critical lysine residue required for maximal catalytic activity, and subdomains VI through IX comprise the highly conserved catalytic core. STKs and PTKs also contain distinct sequence motifs in subdomains VI and VIII, which may confer hydroxyamino acid specificity. Some STKs and PTKs possess structural characteristics of both families. In addition, kinases may also be classified by additional amino acid sequences, generally between 5 and 100 residues, which either flank or occur within the kinase domain.

Examples of protein kinases include, but are not limited to, cAMP-dependent protein kinase, protein kinase C, and cyclin-dependent protein kinases (See, e.g., U.S. Pat. Nos. 6,034,228; 6,030,822; 6,030,788; 6,020,306; 6,013,455; 6,013,464; and 6,015,807, all of which are incorporated herein by reference).

As used herein, the term "protein phosphatase" refers to proteins that remove a phosphate group from a protein. Protein phosphatases are generally divided into two groups, receptor and non-receptor type proteins. Most receptor-type protein tyrosine phosphatases contain two conserved catalytic domains, each of which encompasses a segment of 240 amino acid residues (See e.g., Saito et al., Cell Growth and Diff. 2:59 [1991]). Receptor protein tyrosine phosphatases can be subclassified further based upon the amino acid sequence diversity of their extracellular domains (See e.g., Krueger et al., Proc. Natl. Acad. Sci. USA 89:7417-7421 [1992]). Examples of protein phosphatases include, but are not limited to, cdc25 a, b, and c, PTP20, PTP1D, and PTPλ (See e.g., U.S. Pat. Nos. 5,976,853; 5,994,074; 6,004,791; 5,981,251; 5,976,852; 5,958,719; 5,955,592; and 5,952,212, all of which are incorporated herein by reference).

As used herein, the term "apoptosis" refers to non-necrotic cell death that takes place in metazoan animal cells following activation of an intrinsic cell suicide program. Apoptosis is a normal process in the development and homeostasis of metazoan animals. Apoptosis involves characteristic morphological and biochemical changes, including cell shrinkage, zeiosis, or blebbing, of the plasma membrane, and nuclear collapse and fragmentation of the nuclear chromatin, at intranucleosomal sites, due to activation of an endogenous nuclease.

As used herein, the term "epitope" refers to that portion of an antigen that makes contact with a particular antibody. As used herein, the term "vimentin epitope" refers to a portion of a protein, and variants thereof that are at least 80% identical, wherein said protein has at least one activity of vimentin.

As used herein, the term "antibody" encompasses polyclonal and monoclonal antibody preparations including hybrid antibodies, altered antibodies, F(ab')$_2$ fragments, F(ab) fragments, F$_v$ fragments, single domain antibodies, chimeric antibodies, humanized antibodies, and functional fragments thereof, which retain specificity for vimentin. Thus, if the antibody is to be used in a human, the antibody can be "humanized" in order to reduce immunogenicity yet retain activity.

As used herein, the term "antigen" or "immunogen" refers to a molecule that contains one or more epitopes that will stimulate a host's immune system to make a secretory, humoral and/or cellular antigen-specific response.

As used herein the term "antigenic determinant" refers to that portion of an antigen that makes contact with a particular antibody (i.e., an epitope). When a protein or fragment of a protein is used to immunize a host animal, numerous regions of the protein may induce the production of antibodies that bind specifically to a given region or three-dimensional structure on the protein; these regions or structures are referred to as antigenic determinants. An antigenic determinant may compete with the intact antigen (i.e., the "immunogen" used to elicit the immune response) for binding to an antibody.

As used herein the terms "polypeptide" and "protein" refer to a polymer of amino acid residues and are not limited to a minimum length of the product. Thus peptides, oligopepetides, dimmers, multimers, and the like, are included within the definition. Both full-length proteins and fragments thereof are encompassed by the definition. The terms also include postexpression modifications of the polypeptide, for example, glycosylsation, acetylation, phosphorylation and the like.

"Amino acid sequence" and terms such as "polypeptide" or "protein" are not meant to limit the amino acid sequence to the complete, native amino acid sequence stated with the recited protein molecule.

As used herein, the term "native protein" indicates that a protein does not contain amino acid residues encoded by vector sequences; that is, the native protein contains only those amino acids found in the protein as it occurs in nature. A native protein may be produced by recombinant means or may be isolated from a naturally occurring source.

As used herein the term "portion" when in reference to a protein (as in "a portion of a given protein") refers to fragments of that protein. The fragments may range in size from four amino acid residues to the entire amino acid sequence minus one amino acid.

As applied to polypeptides, the term "substantial identity" means that two peptide sequences, when optimally aligned, such as by the programs GAP or BESTFIT using default gap weights, share at least 80 percent sequence identity, preferably at least 90 percent sequence identity, more preferably at least 95 percent sequence identity or more (e.g., 99 percent sequence identity). Preferably, residue positions that are not identical differ by conservative amino acid substitutions. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, and asparagine-glutamine.

Two pepetides will be "substantially the same" or "substantially identical" when at least about 50%, usually at least about 60%, more typically at least about 75%, and preferably at least about 90-95%, of the amino acids match over a defined length of the molecule. As used herein "substantially the same" also refers to sequences showing identity to the specified polypeptide sequence.

The terms "specific binding" or "specifically binding" when used in reference to the interaction of an antibody and a protein or peptide means that the interaction is dependent upon the presence of a particular structure (i.e., the antigenic determinant or epitope) on the protein; in other words the antibody is recognizing and binding to a specific protein structure rather than to proteins in general. For example, if an antibody is specific for epitope "A," the presence of a protein containing epitope A (or free, unlabelled A) in a reaction containing labeled "A" and the antibody will reduce the amount of labeled A bound to the antibody.

As used herein, the terms "non-specific binding" and "background binding" when used in reference to the interaction of an antibody and a protein or peptide refer to an interaction that is not dependent on the presence of a particular structure (i.e., the antibody is binding to proteins in general rather that a particular structure such as an epitope).

As used herein, the term "a reagent that specifically detects expression levels" refers to reagents used to detect the expression of one or more genes (e.g., including but not limited to, genes encoding vimentin and genes regulating vimentin secretion). Examples of suitable reagents include but are not limited to, nucleic acid probes capable of specifically hybridizing to the gene of interest, PCR primers capable of specifically amplifying the gene of interest, and antibodies capable of specifically binding to proteins expressed by the gene of interest. Other non-limiting examples can be found in the description and examples below.

The term "fragment" as used herein refers to a polypeptide that has an amino-terminal and/or carboxy-terminal deletion as compared to the native protein, but where the remaining amino acid sequence is identical to the corresponding positions in the amino acid sequence deduced from a full-length cDNA sequence. Fragments typically are at least 4 amino acids long, preferably at least 20 amino acids long, usually at least 50 amino acids long or longer, and span the portion of the polypeptide required for intermolecular binding of the compositions (claimed in the present invention) with its various ligands and/or substrates.

As used herein, the term "naturally-occurring" as applied to an object refers to the fact that an object can be found in nature. For example, a polypeptide or polynucleotide sequence that is present in an organism (including viruses) that can be isolated from a source in nature and which has not been intentionally modified by man in the laboratory is naturally occurring.

As used herein, the term "purified" or "to purify" refers to the removal of contaminants from a sample. For example, vimentin antibodies are purified by removal of contaminating non-immunoglobulin proteins; they are also purified by the removal of immunoglobulin that does not bind vimentin. The removal of non-immunoglobulin proteins and/or the removal of immunoglobulins that do not bind vimentin results in an increase in the percent of vimentin-reactive immunoglobulins in the sample. In another example, recombinant vimentin polypeptides are expressed in bacterial host cells and the polypeptides are purified by the removal of host cell proteins; the percent of recombinant vimentin polypeptides is thereby increased in the sample. As used herein, the term "purified" refers to molecules, either nucleic or amino acid sequences, which are removed from their natural environment, isolated or separated. An "isolated nucleic acid sequence" is therefore a purified nucleic acid sequence. "Substantially purified" molecules are at least 60% free, preferably at least 75% free, and more preferably at least 90% free from other components with which they are naturally associated.

As used herein, the term "nucleic acid molecule" refers to any nucleic acid containing molecule, including but not limited to, DNA or RNA. The term encompasses sequences that include any of the known base analogs of DNA and RNA including, but not limited to, 4-acetylcytosine, 8-hydroxy-N6-methyladenosine, aziridinylcytosine, pseudoisocytosine, 5-(carboxyhydroxymethyl) uracil, 5-fluorouracil, 5-bromouracil, 5-carboxymethylaminomethyl-2-thiouracil, 5-carboxymethylaminomethyluracil, dihydrouracil, inosine, N6-isopentenyladenine, 1-methyladenine, 1-methylpseudouracil, 1-methylguanine, 1-methylinosine, 2,2-dimethylguanine, 2-methyladenine, 2-methylguanine, 3-methylcytosine, 5-methylcytosine, N6-methyladenine, 7-methylguanine, 5-methylaminomethyluracil, 5-methoxyaminomethyl-2-thiouracil, beta-D-mannosylqueosine, 5'-methoxycarbonylmethyluracil, 5-methoxyuracil, 2-methylthio-N6-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, N-uracil-5-oxyacetic acid methylester, uracil-5-oxyacetic acid, pseudouracil, queosine, 2-thiocytosine, and 2,6-diaminopurine.

As used herein, the term "gene" refers to a nucleic acid (e.g., DNA) sequence that comprises coding sequences necessary for the production of a polypeptide, precursor, or RNA (e.g., rRNA, tRNA). The polypeptide can be encoded by a full length coding sequence or by any portion of the coding sequence so long as the desired activity or functional properties (e.g., enzymatic activity, ligand binding, signal transduction, immunogenicity, etc.) of the full-length or fragment are retained. The term also encompasses the coding region of a structural gene and the sequences located adjacent to the coding region on both the 5' and 3' ends for a distance of about 1 kb or more on either end such that the gene corresponds to the length of the full-length mRNA. Sequences located 5' of the coding region and present on the mRNA are referred to as 5' non-translated sequences. Sequences located 3' or downstream of the coding region and present on the mRNA are referred to as 3' non-translated sequences. The term "gene" encompasses both cDNA and genomic forms of a gene. A genomic form or clone of a gene contains the coding region interrupted with non-coding sequences termed "introns" or "intervening regions" or "intervening sequences." Introns are segments of a gene that are transcribed into nuclear RNA (hnRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide.

As used herein, the term "genome" refers to the genetic material (e.g., chromosomes) of an organism.

As used herein, the term "heterologous gene" refers to a gene that is not in its natural environment. For example, a heterologous gene includes a gene from one species introduced into another species. A heterologous gene also includes a gene native to an organism that has been altered in some way (e.g., mutated, added in multiple copies, linked to non-native regulatory sequences, etc). Heterologous genes are distinguished from endogenous genes in that the heterologous gene sequences are typically joined to DNA sequences that are not found naturally associated with the gene sequences in the chromosome or are associated with portions of the chromosome not found in nature (e.g., genes expressed in loci where the gene is not normally expressed).

As used herein, the term "gene expression" refers to the process of converting genetic information encoded in a gene into RNA (e.g., mRNA, rRNA, tRNA, or snRNA) through "transcription" of the gene (i.e., via the enzymatic action of an RNA polymerase), and for protein encoding genes, into protein through "translation" of mRNA. Gene expression can be regulated at many stages in the process. "Up-regulation" or "activation" refers to regulation that increases the production of gene expression products (i.e., RNA or protein), while "down-regulation" or "repression" refers to regulation that decrease production. Molecules (e.g., transcription factors) that are involved in up-regulation or down-regulation are often called "activators" and "repressors," respectively.

In addition to containing introns, genomic forms of a gene may also include sequences located on both the 5' and 3' end of the sequences that are present on the RNA transcript. These sequences are referred to as "flanking" sequences or regions (these flanking sequences are located 5' or 3' to the non-translated sequences present on the mRNA transcript). The 5' flanking region may contain regulatory sequences such as promoters and enhancers that control or influence the transcription of the gene. The 3' flanking region may contain sequences that direct the termination of transcription, post-transcriptional cleavage and polyadenylation.

As used herein, the term "site-specific recombination target sequences" refers to nucleic acid sequences that provide recognition sequences for recombination factors and the location where recombination takes place.

As used herein, the term "wild-type" refers to a gene or gene product isolated from a naturally occurring source. A wild-type gene is that which is most frequently observed in a population and is thus arbitrarily designed the "normal" or "wild-type" form of the gene. In contrast, the term "modified" or "mutant" refers to a gene or gene product that displays modifications in sequence and or functional properties (i.e., altered characteristics) when compared to the wild-type gene or gene product. It is noted that naturally occurring mutants can be isolated; these are identified by the fact that they have altered characteristics (including altered nucleic acid sequences) when compared to the wild-type gene or gene product.

As used herein, the terms "nucleic acid molecule encoding," "DNA sequence encoding," and "DNA encoding" refer to the order or sequence of deoxyribonucleotides along a strand of deoxyribonucleic acid. The order of these deoxyribonucleotides determines the order of amino acids along the polypeptide (protein) chain. The DNA sequence thus codes for the amino acid sequence.

As used herein, the terms "an oligonucleotide having a nucleotide sequence encoding a gene" and "polynucleotide having a nucleotide sequence encoding a gene," means a nucleic acid sequence comprising the coding region of a gene or in other words the nucleic acid sequence that encodes a gene product. The coding region may be present in a cDNA, genomic DNA or RNA form. When present in a DNA form, the oligonucleotide or polynucleotide may be single-stranded (i.e., the sense strand) or double-stranded. Suitable control elements such as enhancers/promoters, splice junctions, polyadenylation signals, etc. may be placed in close proximity to the coding region of the gene if needed to permit proper initiation of transcription and/or correct processing of the primary RNA transcript. Alternatively, the coding region utilized in the expression vectors of the present invention may contain endogenous enhancers/promoters, splice junctions, intervening sequences, polyadenylation signals, etc. or a combination of both endogenous and exogenous control elements.

As used herein, the term "oligonucleotide" refers to a short length of single-stranded polynucleotide chain. Oligonucleotides are typically less than 200 residues long (e.g., between 15 and 100), however, as used herein, the term is also intended to encompass longer polynucleotide chains. Oligonucleotides are often referred to by their length. For example a 24 residue oligonucleotide is referred to as a "24-mer". Oligonucleotides can form secondary and tertiary structures by self-hybridizing or by hybridizing to other polynucleotides. Such structures can include, but are not limited to, duplexes, hairpins, cruciforms, bends, and triplexes.

As used herein, the terms "complementary" or "complementarity" are used in reference to polynucleotides (i.e., a sequence of nucleotides) related by the base-pairing rules. For example, for the sequence "5'-A-G-T-3'," is complementary to the sequence "3'-T-C-A-5'." Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands. This is of particular importance in amplification reactions, as well as detection methods that depend upon binding between nucleic acids.

As used herein, the term "homology" refers to a degree of complementarity. There may be partial homology or complete homology (i.e., identity). A partially complementary sequence is a nucleic acid molecule that at least partially inhibits a completely complementary nucleic acid molecule from hybridizing to a target nucleic acid is "substantially homologous." The inhibition of hybridization of the completely complementary sequence to the target sequence may be examined using a hybridization assay (Southern or Northern blot, solution hybridization and the like) under conditions of low stringency. A substantially homologous sequence or probe will compete for and inhibit the binding (i.e., the hybridization) of a completely homologous nucleic acid molecule to a target under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target that is substantially non-complementary (e.g., less than about 30% identity); in the absence of non-specific binding the probe will not hybridize to the second non-complementary target.

When used in reference to a double-stranded nucleic acid sequence such as a cDNA or genomic clone, the term "substantially homologous" refers to any probe that can hybridize to either or both strands of the double-stranded nucleic acid sequence under conditions of low stringency as described above.

A gene may produce multiple RNA species that are generated by differential splicing of the primary RNA transcript. cDNAs that are splice variants of the same gene will contain regions of sequence identity or complete homology (representing the presence of the same exon or portion of the same exon on both cDNAs) and regions of complete non-identity (for example, representing the presence of exon "A" on cDNA 1 wherein cDNA 2 contains exon "B" instead). Because the two cDNAs contain regions of sequence identity they will both hybridize to a probe derived from the entire gene or portions of the gene containing sequences found on both cDNAs; the two splice variants are therefore substantially homologous to such a probe and to each other.

When used in reference to a single-stranded nucleic acid sequence, the term "substantially homologous" refers to any probe that can hybridize (i.e., it is the complement of) the single-stranded nucleic acid sequence under conditions of low stringency as described above.

As used herein, the term "hybridization" is used in reference to the pairing of complementary nucleic acids. Hybridization and the strength of hybridization (i.e., the strength of the association between the nucleic acids) is impacted by such factors as the degree of complementary between the nucleic acids, stringency of the conditions involved, the $T_m$ of the formed hybrid, and the G:C ratio within the nucleic acids.

A single molecule that contains pairing of complementary nucleic acids within its structure is said to be "self-hybridized."

As used herein, the term "$T_m$" is used in reference to the "melting temperature." The melting temperature is the temperature at which a population of double-stranded nucleic acid molecules becomes half dissociated into single strands. The equation for calculating the $T_m$ of nucleic acids is well known in the art. As indicated by standard references, a simple estimate of the $T_m$ value may be calculated by the equation: $T_m=81.5+0.41(\% \text{ G+C})$, when a nucleic acid is in aqueous solution at 1 M NaCl (See e.g., Anderson and Young, Quantitative Filter Hybridization, in Nucleic Acid Hybridization [1985]). Other references include more sophisticated computations that take structural as well as sequence characteristics into account for the calculation of $T_m$.

As used herein the term "stringency" is used in reference to the conditions of temperature, ionic strength, and the presence of other compounds such as organic solvents, under which nucleic acid hybridizations are conducted. Under "low stringency conditions" a nucleic acid sequence of interest will hybridize to its exact complement, sequences with single base mismatches, closely related sequences (e.g., sequences with 90% or greater homology), and sequences having only partial homology (e.g., sequences with 50-90% homology). Under "medium stringency conditions," a nucleic acid sequence of interest will hybridize only to its exact complement, sequences with single base mismatches, and closely relation sequences (e.g., 90% or greater homology). Under "high stringency conditions," a nucleic acid sequence of interest will hybridize only to its exact complement, and (depending on conditions such a temperature) sequences with single base mismatches. In other words, under conditions of high stringency the temperature can be raised so as to exclude hybridization to sequences with single base mismatches.

"High stringency conditions" when used in reference to nucleic acid hybridization comprise conditions equivalent to binding or hybridization at 42° C. in a solution consisting of 5×SSPE (43.8 g/l NaCl, 6.9 g/l NaH$_2$PO$_4$ H$_2$O and 1.85 g/l EDTA, pH adjusted to 7.4 with NaOH), 0.5% ADS, 5×Denhardt's reagent and 100 µg/ml denatured salmon sperm DNA followed by washing in a solution comprising 0.1×SSPE, 1.0% SDS at 42° C. when a probe of about 500 nucleotides in length is employed.

"Medium stringency conditions" when used in reference to nucleic acid hybridization comprise conditions equivalent to binding or hybridization at 42° C. in a solution consisting of 5×SSPE (43.8 g/l NaCl, 6.9 g/l NaH$_2$PO$_4$ H$_2$O and 1.85 g/l EDTA, pH adjusted to 7.4 with NaOH), 0.5% SDS, 5×Denhardt's reagent and 100 µg/ml denatured salmon sperm DNA followed by washing in a solution comprising 1.0×SSPE, 1.0% SDS at 42° C. when a probe of about 500 nucleotides in length is employed.

"Low stringency conditions" comprise conditions equivalent to binding or hybridization at 42° C. in a solution consisting of 5×SSPE (43.8 g/l NaCl, 6.9 g/l NaH$_2$PO$_4$ H$_2$O and 1.85 g/l EDTA, pH adjusted to 7.4 with NaOH), 0.1% SDS, 5×Denhardt's reagent [50×Denhardt's contains per 500 ml: 5 g Ficoll (Type 400, Pharamcia), 5 g BSA (Fraction V; Sigma)] and 100 µg/ml denatured salmon sperm DNA followed by washing in a solution comprising 5×SSPE, 0.1% SDS at 42° C. when a probe of about 500 nucleotides in length is employed.

The art knows well that numerous equivalent conditions may be employed to comprise low stringency conditions; factors such as the length and nature (DNA, RNA, base composition) of the probe and nature of the target (DNA, RNA, base composition, present in solution or immobilized, etc.) and the concentration of the salts and other components (e.g., the presence or absence of formamide, dextran sulfate, polyethylene glycol) are considered and the hybridization solution may be varied to generate conditions of low stringency hybridization different from, but equivalent to, the above listed conditions. In addition, the art knows conditions that promote hybridization under conditions of high stringency (e.g., increasing the temperature of the hybridization and/or wash steps, the use of formamide in the hybridization solution, etc.) (See definition above for "stringency").

"Amplification" is a special case of nucleic acid replication involving template specificity. It is to be contrasted with non-specific template replication (i.e., replication that is template-dependent but not dependent on a specific template). Template specificity is here distinguished from fidelity of replication (i.e., synthesis of the proper polynucleotide sequence) and nucleotide (ribo- or deoxyribo-) specificity. Template specificity is frequently described in terms of "target" specificity. Target sequences are "targets" in the sense that they are sought to be sorted out from other nucleic acid. Amplification techniques have been designed primarily for this sorting out.

Template specificity is achieved in most amplification techniques by the choice of enzyme. Amplification enzymes are enzymes that, under conditions they are used, will process only specific sequences of nucleic acid in a heterogeneous mixture of nucleic acid. For example, in the case of Qβ replicase, MDV-1 RNA is the specific template for the replicase (Kacian et al., Proc. Natl. Acad. Sci. USA 69:3038 [1972]). Other nucleic acids will not be replicated by this amplification enzyme. Similarly, in the case of T7 RNA polymerase, this amplification enzyme has a stringent specificity for its own promoters (Chamberlin et al., Nature 228:227 [1970]). In the case of T4 DNA ligase, the enzyme will not ligate the two oligonucleotides or polynucleotides, where there is a mismatch between the oligonucleotide or polynucleotide substrate and the template at the ligation junction (Wu and Wallace, Genomics 4:560 [1989]). Finally, Taq and Pfu polymerases, by virtue of their ability to function at high temperature, are found to display high specificity for the sequences bounded and thus defined by the primers; the high temperature results in thermodynamic conditions that favor primer hybridization with the target sequences and not hybridization with non-target sequences (H. A. Erlich (ed.), PCR Technology, Stockton Press [1989]).

As used herein, the term "amplifiable nucleic acid" is used in reference to nucleic acids that may be amplified by any amplification method. It is contemplated that "amplifiable nucleic acid" will usually comprise "sample template."

As used herein, the term "sample template" refers to nucleic acid originating from a sample that is analyzed for the presence of "target." In contrast, "background template" is used in reference to nucleic acid other than sample template that may or may not be present in a sample. Background template is most often inadvertent. It may be the result of carryover, or it may be due to the presence of nucleic acid contaminants sought to be purified away from the sample. For example, nucleic acids from organisms other than those to be detected may be present as background in a test sample.

As used herein, the term "primer" refers to an oligonucleotide, whether occurring naturally as in a purified restriction digest or produced synthetically, that is capable of acting as a point of initiation of synthesis when placed under conditions in which synthesis of a primer extension product that is complementary to a nucleic acid strand is induced, (i.e., in the presence of nucleotides and an inducing agent such as DNA polymerase and at a suitable temperature and pH). The primer is preferably single stranded for maximum efficiency in amplification, but may alternatively be double stranded. If double stranded, the primer is first treated to separate its strands before being used to prepare extension products. Preferably, the primer is an oligodeoxyribonucleotide. The primer must be sufficiently long to prime the synthesis of extension products in the presence of the inducing agent. The exact lengths of the primers will depend on many factors, including temperature, source of primer and the use of the method.

As used herein, the term "probe" refers to an oligonucleotide (i.e., a sequence of nucleotides), whether occurring naturally as in a purified restriction digest or produced synthetically, recombinantly or by PCR amplification, that is capable of hybridizing to at least a portion of another oligonucleotide of interest. A probe may be single-stranded or double-stranded. Probes are useful in the detection, identification and isolation of particular gene sequences. It is contemplated that any probe used in the present invention will be labeled with any "reporter molecule," so that is detectable in any detection system, including, but not limited to enzyme (e.g., ELISA, as well as enzyme-based histochemical assays), fluorescent, radioactive, and luminescent systems. It is not intended that the present invention be limited to any particular detection system or label.

As used herein the term "portion" when in reference to a nucleotide sequence (as in "a portion of a given nucleotide sequence") refers to fragments of that sequence. The fragments may range in size from four nucleotides to the entire nucleotide sequence minus one nucleotide (10 nucleotides, 20, 30, 40, 50, 100, 200, etc.).

As used herein, the term "target," in reference to amplification, refers to the region of nucleic acid bounded by the primers. Thus, the "target" is sought to be sorted out from other nucleic acid sequences. A "segment" is defined as a region of nucleic acid within the target sequence.

As used herein, the term "polymerase chain reaction" ("PCR") refers to the method of K. B. Mullis U.S. Pat. Nos. 4,683,195 4,683,202, and 4,965,188, hereby incorporated by reference, which describe a method for increasing the concentration of a segment of a target sequence in a mixture of genomic DNA without cloning or purification. This process for amplifying the target sequence consists of introducing a large excess of two oligonucleotide primers to the DNA mixture containing the desired target sequence, followed by a precise sequence of thermal cycling in the presence of a DNA polymerase. The two primers are complementary to their respective strands of the double stranded target sequence. To effect amplification, the mixture is denatured and the primers then annealed to their complementary sequences within the target molecule. Following annealing, the primers are extended with a polymerase so as to form a new pair of complementary strands. The steps of denaturation, primer annealing and polymerase extension can be repeated many times (i.e., denaturation, annealing and extension constitute one "cycle"; there can be numerous "cycles") to obtain a high concentration of an amplified segment of the desired target sequence. The length of the amplified segment of the desired target sequence is determined by the relative positions of the primers with respect to each other, and therefore, this length is a controllable parameter. By virtue of the repeating aspect of the process, the method is referred to as the "polymerase chain reaction" (hereinafter "PCR"). Because the desired amplified segments of the target sequence become the predominant sequences (in terms of concentration) in the mixture, they are said to be "PCR amplified".

With PCR, it is possible to amplify a single copy of a specific target sequence in genomic DNA to a level detectable by several different methodologies (e.g., hybridization with a labeled probe; incorporation of biotinylated primers followed by avidin-enzyme conjugate detection; incorporation of $^{32}$P-labeled deoxynucleotide triphosphates, such as dCTP or dATP, into the amplified segment). In addition to genomic DNA, any oligonucleotide or polynucleotide sequence can be amplified with the appropriate set of primer molecules. In particular, the amplified segments created by the PCR process are, themselves, efficient templates for subsequent PCR amplifications.

As used herein, the terms "PCR product" "PCR fragment," and "amplification product" refer to the resultant mixture of compounds after two or more cycles of the PCR steps of denaturation, annealing and extension are complete. These terms encompass the case where there has been amplification of one or more segments of one or more target sequences.

As used herein, the term "amplification reagents" refers to those reagents (deoxyribonucleotide triphosphates, buffer, etc.), needed for amplification except for primers, nucleic acid template and the amplification enzyme. Typically, amplification reagents along with other reaction components are placed and contained in a reaction vessel (test tube, microwell, etc.).

The terms "in operable combination" "in operable order," and "operably linked" as used herein refer to the linkage of nucleic acid sequences in such a manner that a nucleic acid molecule capable of directing the transcription of a given gene and/or the synthesis of a desired protein molecule is produced. The term also refers to the linkage of amino acid sequences in such a manner so that a functional protein is produced.

The term "isolated" when used in relation to a nucleic acid, as in "an isolated oligonucleotide" or "isolated polynucleotide" refers to a nucleic acid sequence that is identified and separated from at least one component or contaminant with which it is ordinarily associated in its natural source. Isolated nucleic acid is such present in a form or setting that is different from that in which it is found in nature. In contrast, non-isolated nucleic acids as nucleic acids such as DNA and RNA found in the state they exist in nature. For example, a given DNA sequence (e.g., a gene) is found on the host cell chromosome in proximity to neighboring genes; RNA sequences, such as a specific mRNA sequence encoding a specific protein, are found in the cell as a mixture with numerous other mRNAs that encode a multitude of proteins. However, isolated nucleic acid encoding a given protein includes, by way of example, such nucleic acid in cells ordinarily expressing the given protein where the nucleic acid is in a chromosomal location different from that of natural cells, or is otherwise flanked by a different nucleic acid sequence than that found in nature. The isolated nucleic acid, oligonucleotide, or polynucleotide may be present in single-stranded or double-stranded form. When an isolated nucleic acid, oligonucleotide or polynucleotide is to be utilized to express a protein, the oligonucleotide or polynucleotide will contain at a minimum the sense or coding strand (i.e., the oligonucleotide or polynucleotide may be single-stranded), but may contain both the sense and anti-sense strands (i.e., the oligonucleotide or polynucleotide may be double-stranded).

The term "Southern blot" refers to the analysis of DNA on agarose or acrylamide gels to fractionate the DNA according to size followed by transfer of the DNA from the gel to a solid support, such as nitrocellulose or a nylon membrane. The immobilized DNA is then probed with a labeled probe to detect DNA species complementary to the probe used. The DNA may be cleaved with restriction enzymes prior to electrophoresis. Following electrophoresis, the DNA may be partially depurinated and denatured prior to or during transfer to the solid support. Southern blots are a standard tool of molecular biologists (J. Sambrook et al., Molecular Cloning: A Laboratory Manual, Cold Spring Harbor Press, N.Y., pp 9.31-9.58 [1989]).

The term "Northern blot" as used herein refers to the analysis of RNA by electrophoresis of RNA on agarose gels to fractionate the RNA according to size followed by transfer of the RNA from the gel to a solid support, such as nitrocellulose or a nylon membrane. The immobilized RNA is then probed with a labeled probe to detect RNA species complementary to the probe used. Northern blots are a standard tool of molecular biologists (J. Sambrook, et al., supra, pp 7.39-7.52 [1989]).

The term "Western blot" refers to the analysis of protein(s) (or polypeptides) immobilized onto a support such as nitrocellulose or a membrane. The proteins are run on acrylamide gels to separate the proteins, followed by transfer of the protein from the gel to a solid support, such as nitrocellulose or a nylon membrane. The immobilized proteins are then exposed to antibodies with reactivity against an antigen of interest. The binding of the antibodies may be detected by various methods, including the use of radiolabeled antibodies.

As used herein, the term "vector" is used in reference to nucleic acid molecules that transfer DNA segment(s) from one cell to another. The term "vehicle" is sometimes used interchangeably with "vector." Vectors are often derived from plasmids, bacteriophages, or plant or animal viruses.

The term "expression vector" as used herein refers to a recombinant DNA molecule containing a desired coding sequence and appropriate nucleic acid sequences necessary for the expression of the operably linked coding sequence in a particular host organism. Nucleic acid sequences necessary for expression in prokaryotes usually include a promoter, an operator (optional), and a ribosome-binding site, often along with other sequences. Eukaryotic cells are known to utilize promoters, enhancers, and termination and polyadenylation signals.

As used herein, the term "eukaryote" refers to organisms distinguishable from "prokaryotes." It is intended that the term encompass all organisms with cells that exhibit the usual characteristics of eukaryotes, such as the presence of a true nucleus bounded by a nuclear membrane, within which lie the chromosomes, the presence of membrane-bound organelles, and other characteristics commonly observed in eukaryotic organisms. Thus, the term includes, but is not limited to such organisms as fungi, protozoa, and animals (e.g., humans).

As used herein, the terms "nucleic acid molecule encoding," "DNA sequence encoding," and "DNA encoding" refer to the order or sequence of deoxyribonucleotides along a strand of deoxyribonucleic acid. The order of these deoxyribonucleotides determines the order of amino acids along the polypeptide (protein) chain. The DNA sequence thus codes for the amino acid sequence.

DNA molecules are said to have "5' ends" and "3' ends" because mononucleotides are reacted to make oligonucleotides or polynucleotides in a manner such that the 5' phosphate of one mononucleotide pentose ring is attached to the 3' oxygen of its neighbor in one direction via a phosphodiester linkage. Therefore, an end of an oligonucleotides or polynucleotide, referred to as the "5' end" if its 5' phosphate is not linked to the 3' oxygen of a mononucleotide pentose ring and as the "3' end" if its 3' oxygen is not linked to a 5' phosphate of a subsequent mononucleotide pentose ring. As used herein, a nucleic acid sequence, even if internal to a larger oligonucleotide or polynucleotide, also may be said to have 5' and 3' ends. In either a linear or circular DNA molecule, discrete elements are referred to as being "upstream" or 5' of the "downstream" or 3' elements. This terminology reflects the fact that transcription proceeds in a 5' to 3' fashion along the DNA strand. The promoter and enhancer elements that direct transcription of a linked gene are generally located 5' or upstream of the coding region. However, enhancer elements can exert their effect even when located 3' of the promoter element and the coding region. Transcription termination and polyadenylation signals are located 3' or downstream of the coding region.

As used herein, the term "antisense" is used in reference to RNA sequences that are complementary to a specific RNA sequence (e.g., mRNA). Included within this definition are antisense RNA ("asRNA") molecules involved in gene regulation by bacteria. Antisense RNA may be produced by any method, including synthesis by splicing the gene(s) of interest in a reverse orientation to a viral promoter that permits the synthesis of a coding strand. Once introduced into an embryo, this transcribed strand combines with natural mRNA produced by the embryo to form duplexes. These duplexes then block either the further transcription of the mRNA or its translation. In this manner, mutant phenotypes may be generated. The term "antisense strand" is used in reference to a nucleic acid strand that is complementary to the "sense" strand. The designation (−) (i.e., "negative") is sometimes used in reference to the antisense strand, with the designation (+) sometimes used in reference to the sense (i.e., "positive") strand.

As used herein, the term "siRNAs" refers to small interfering RNAs. In some embodiments, siRNAs comprise a duplex, or double-stranded region, of about 18-25 nucleotides long; often siRNAs contain from about two to four unpaired nucleotides at the 3' end of each strand. At least one strand of the duplex or double-stranded region of a siRNA is substantially homologous to, or substantially complementary to, a target RNA molecule. The strand complementary to a target RNA molecule is the "antisense strand;" the strand homologous to the target RNA molecule is the "sense strand," and is also complementary to the siRNA antisense strand. siRNAs may also contain additional sequences; non-limiting examples of such sequences include linking sequences, or loops, as well as stem and other folded structures. siRNAs appear to function as key intermediaries in triggering RNA interference in invertebrates and in vertebrates, and in triggering sequence-specific RNA degradation during posttranscriptional gene silencing in plants.

The term "RNA interference" or "RNAi" refers to the silencing or decreasing of gene expression by siRNAs. It is the process of sequence-specific, post-transcriptional gene silencing in animals and plants, initiated by siRNA that is homologous in its duplex region to the sequence of the silenced gene. The gene may be endogenous or exogenous to the organism, present integrated into a chromosome or present in a transfection vector that is not integrated into the genome. The expression of the gene is either completely or partially inhibited. RNAi may also be considered to inhibit the function of a target RNA; the function of the target RNA may be complete or partial.

As used herein, the term "nucleic acid binding protein" refers to proteins that bind to nucleic acid, and in particular to proteins that cause increased (i.e., activators or transcription factors) or decreased (i.e., inhibitors) transcription from a gene.

As used herein, the term "mimetic" refers to a small molecule compound that mimics the binding of a ligand to its target. For example, a mimetic of a peptide inhibitor of a vimentin protein is a small molecule that binds to the same site of the vimentin protein, as does the peptide.

As used herein, the term "signal protein" refers to a protein that is co-expressed with a protein of interest and which, when detected by a suitable assay, provides indirect evidence of expression of the protein of interest. Examples of signal proteins include, but are not limited to, immunoglobulin heavy and light chains, beta-galactosidase, beta-lactamase, green fluorescent protein, and luciferase.

DETAILED DESCRIPTION OF THE INVENTION

The present invention relates to methods for screening and modulating the bioavailability of extracellular secretory vimentin. In particular, the present invention provides inhibitors and activators of secretory vimentin including antibodies, small interfering RNAs, and antisense oligonucleotides. The present invention thus provides novel drug targets for enhanced anti-microbial response, and methods of using such modulators to beneficially alter the pathophysiologic effects of secretory vimentin.

I. Drug Screening Using Secretory Vimentin

The present invention provides methods and compositions for using vimentin as a target for screening drugs that can alter, for example, the oxidative burst and cellular inflammatory responses. For example, drugs that induce or inhibit vimentin mediated inflammatory responses can be identified by screening for compounds that target secretory vimentin, or regulate secretory vimentin gene expression.

The present invention is not limited to a particular mechanism of action. Indeed, an understanding of the mechanism of action is not necessary to practice the present invention. Accordingly, it is contemplated that binding assays are useful for screening for compounds that increase or decrease vimentin binding to pathogens. In particular, it is contemplated that such screens are capable of identifying compounds that are useful for potentiating or diminishing vimentin activity and thus for treating microbial infections, and autoimmune disorders. The binding need not employ full-length vimentin. Indeed, portions of vimentin may be utilized in the binding assays.

In one screening method, candidate compounds are evaluated for their ability to alter secretory vimentin bioavailability by contacting vimentin, or fragments thereof, with the candidate compound and determining binding of the candidate compound to the peptide.

In another screening method, secretory vimentin or a fragment of secretory vimentin, are immobilized. Polypeptides can be immobilized using methods known in the art, such as adsorption onto a plastic microtiter plate or specific binding of a GST-fusion protein to a polymeric bead containing glutathione. For example, GST-vimentin is bound to glutathione-SEPHAROSE (agarose polysaccarhide polymer) beads. The immobilized peptide is then contacted with another peptide with which it is capable of binding in the presence and absence of a candidate compound. Unbound peptide is then removed and the complex solubilized and analyzed to determine the amount of bound labeled peptide. A decrease in binding is an indication that the candidate compound inhibits the interaction of vimentin with the other peptide. A variation of this method allows for the screening of compounds that are capable of disrupting a previously formed protein/protein complex. For example, in some embodiments a complex comprising vimentin or a vimentin fragment bound to another peptide is immobilized as described above and contacted with a candidate compound. The dissolution of the complex by the candidate compound correlates with the ability of the compound to disrupt or inhibit the interaction between vimentin and the other peptide.

Another technique for drug screening provides high throughput screening for compounds having suitable binding affinity to secretory vimentin peptides and is described in detail in WO 84/03564, incorporated herein by reference. Briefly, large numbers of different small peptide test compounds are synthesized on a solid substrate, such as plastic pins or some other surface. The peptide test compounds are then reacted with vimentin peptides and washed. Bound vimentin peptides are then detected by methods well known in the art.

Another technique uses vimentin antibodies, generated as discussed below. Such antibodies capable of specifically binding to vimentin peptides compete with a test compound for binding to vimentin. In this manner, the antibodies can be used to detect the presence of any peptide that shares one or more antigenic determinants of the vimentin peptide.

In some embodiments of the present invention, compounds are screened for their ability to inhibit the binding of pathogen components (e.g., including, but not limited to, bacterial cell surface proteins, fungal proteins, parasite proteins, and virus proteins) to vimentin. Any suitable screening assay may be utilized, including, but not limited to, those described herein.

The present invention contemplates many other means of screening compounds. The examples provided above are presented merely to illustrate a range of techniques available. One of ordinary skill in the art will appreciate that many other screening methods can be used.

In particular, the present invention contemplates the use of cell lines transfected with vimentin and variants or mutants thereof for screening compounds for activity, and in particular to high throughput screening of compounds from combinatorial libraries (e.g., libraries containing greater than $10^4$ compounds). The cell lines of the present invention can be used in a variety of screening methods. In some embodiments, the cells can be used in second messenger assays that monitor signal transduction following activation of cell-surface receptors triggering vimentin secretion. In other embodiments, the cells can be used in reporter gene assays that monitor cellular responses at the transcription/translation level. In still further embodiments, the cells can be used in cell proliferation assays to monitor the overall growth/no growth response of cells to external stimuli including secretory vimentin.

In second messenger assays, the host cells are preferably transfected as described above with vectors encoding vimentin or variants or mutants thereof. The host cells are then treated with a compound or plurality of compounds (e.g., from a combinatorial library) and assayed for the presence or absence of a response. It is contemplated that at least some of the compounds in the combinatorial library can serve as agonists, antagonists, activators, or inhibitors of the protein or proteins encoded by the vectors. It is also contemplated that at least some of the compounds in the combinatorial library can serve as agonists, antagonists, activators, or inhibitors of protein acting upstream or downstream of the protein encoded by the vector in a signal transduction pathway.

In some embodiments, the second messenger assays measure fluorescent signals from reporter molecules that respond to intracellular changes (e.g., $Ca^{2+}$ concentration, membrane potential, pH, $IP_3$, cAMP, arachidonic acid release) due to stimulation of membrane receptors and ion channels (e.g., ligand gated ion channels; see Denyer et al., Drug Discov. Today 3:323-32 [1998]; and Gonzales et al., Drug. Discov. Today 4:431-39 [1999]). Examples of reporter molecules include, but are not limited to, FRET (florescence resonance energy transfer) systems (e.g., Cuo-lipids and oxonols, EDAN/DABCYL), calcium sensitive indicators (e.g., Fluo-3, FURA 2, INDO 1, and FLUO3/AM, BAPTA AM), chloride-sensitive indicators (e.g., SPQ, SPA), potassium-sensitive indicators (e.g., PBFI), sodium-sensitive indicators (e.g., SBFI), and pH sensitive indicators (e.g., BCECF).

In general, the host cells are loaded with the indicator prior to exposure to the compound. Responses of the host cells to treatment with the compounds can be detected by methods known in the art, including, but not limited to, fluorescence microscopy, confocal microscopy (e.g., FCS systems), flow cytometry, microfluidic devices, FLIPR systems (See, e.g., Schroeder and Neagle, J. Biomol. Screening 1:75-80 [1996]), and plate-reading systems. In some preferred embodiments, the response (e.g., increase in fluorescent intensity) caused by compound of unknown activity is compared to the response generated by a known agonist and expressed as a percentage of the maximal response of the known agonist. The maximum response caused by a known agonist is defined as a 100% response. Likewise, the maximal response recorded after addition of an agonist to a sample containing a known or test antagonist is detectably lower than the 100% response.

The cells are also useful in reporter gene assays. Reporter gene assays involve the use of host cells transfected with vectors encoding a nucleic acid comprising transcriptional control elements of a target gene (i.e., a gene that controls the biological expression and function of a disease target) spliced to a coding sequence for a reporter gene. Therefore, activation of the target gene results in activation of the reporter gene product. As described above, it is contemplated vimentin binds with an antibody, and this binding results in inhibition of the oxidative burst in vitro. Therefore, in some embodiments, the reporter gene construct comprises the 5' regulatory region (e.g., promoters and/or enhancers) of a protein whose expression is controlled by the oxidative burst in operable association with a reporter gene (See Example 4 and Inohara et al., J. Biol. Chem. 275:27823-31 [2000] for a description of the luciferase reporter construct pBVIx-Luc). Examples of reporter genes finding use in the present invention include, but are not limited to, chloramphenicol transferase, alkaline phosphatase, firefly and bacterial luciferases, _-galactosidase, _-lactamase, and green fluorescent protein. The production of these proteins, with the exception of green fluorescent protein, is detected through the use of chemiluminescent, calorimetric, or bioluminescent products of specific substrates (e.g., X-gal and luciferin). Comparisons between compounds of known and unknown activities may be conducted as described above.

It is further contemplated that the site with which secretory vimentin interacts finds use as a novel target for drug action. Accordingly, uses of the methods of the present invention include, but are not limited to: 1) development of pro-drugs which deliver a peptide to extracellular sites, 2) using the structure-activity relations to design peptido-mimetic or small molecule vimentin activators and inhibitors, and 3) obtaining crystal structures of the complex of the vimentin and target proteins to specify a well-defined site for small molecule inhibitor design.

Synthesis of nonpeptide compounds that mimic peptide sequences is also known in the art. Eldred et al. (J. Med. Chem., 37:3882 [1994]) describe nonpeptide antagonists that mimic the Arg-Gly-Asp sequence. Likewise, Ku et al. (J. Med. Chem., 38:9 [1995]) give further elucidation of the synthesis of a series of such compounds. Such nonpeptide compounds that mimic peptide inhibitors of the present invention are specifically contemplated by the present invention.

The present invention also contemplates synthetic mimicking compounds that are multimeric compounds that repeat the relevant peptide sequence. As is known in the art, peptides can be synthesized by linking an amino group to a carboxyl group that has been activated by reaction with a coupling agent, such as dicyclohexylcarbodiimide (DCC). The attack of a free amino group on the activated carboxyl leads to the formation of a peptide bond and the release of dicyclohexylurea. It can be necessary to protect potentially reactive groups other than the amino and carboxyl groups intended to react. For example, the α-amino group of the component containing the activated carboxyl group can be blocked with a tertbutyloxy-carbonyl group. This protecting group can be subsequently removed by exposing the peptide to dilute acid, which leaves peptide bonds intact.

With this method, peptides can be readily synthesized by a solid phase method by adding amino acids stepwise to a growing peptide chain that is linked to an insoluble matrix, such as polystyrene beads. The carboxyl-terminal amino acid (with an amino protecting group) of the desired peptide sequence is first anchored to the polystyrene beads. The protecting group of the amino acid is then removed. The next amino acid (with the protecting group) is added with the coupling agent. This is followed by a washing cycle. The cycle is repeated as necessary.

II. Secretory Vimentin Antibodies

The present invention provides isolated antibodies. In preferred embodiments, the present invention provides monoclonal antibodies that specifically bind to secretory vimentin, vimentin fragments, byproducts, derivatives and analogs. These antibodies find use in the screening and therapeutic methods described herein.

An antibody against a protein of the present invention may be any monoclonal or polyclonal antibody, as long as it can recognize the protein. Antibodies can be produced by using a protein of the present invention as the antigen according to a conventional antibody or antiserum preparation process.

The present invention contemplates the use of both monoclonal and polyclonal antibodies. Any suitable method may be used to generate the antibodies used in the methods and compositions of the present invention, including but not limited to, those disclosed herein. For example, for preparation of a monoclonal antibody, protein, as such, or together with a suitable carrier or diluent is administered to an animal (e.g., a mammal) under conditions that permit the production of antibodies. For enhancing the antibody production capability, complete or incomplete Freund's adjuvant may be administered. Normally, the protein is administered once every 2 weeks to 6 weeks, in total, about 2 times to about 10 times. Animals suitable for use in such methods include, but are not limited to, primates, rabbits, dogs, guinea pigs, mice, rats, sheep, goats, etc.

For preparing monoclonal antibody-producing cells, an individual animal whose antibody titer has been confirmed (e.g., a mouse) is selected, and 2 days to 5 days after the final immunization, its spleen or lymph node is harvested and antibody-producing cells contained therein are fused with myeloma cells to prepare the desired monoclonal antibody producer hybridoma. Measurement of the antibody titer in antiserum can be carried out, for example, by reacting the labeled protein, as described hereinafter and antiserum and then measuring the activity of the labeling agent bound to the antibody. The cell fusion can be carried out according to known methods, for example, the method described by Koehler and Milstein (Nature 256:495 [1975]). As a fusion promoter, for example, polyethylene glycol (PEG) or Sendai virus (HVJ), preferably PEG is used.

Examples of myeloma cells include NS-1, P3U1, SP2/0, AP-1 and the like. The proportion of the number of antibody producer cells (spleen cells) and the number of myeloma cells to be used is preferably about 1:1 to about 20:1. PEG (preferably PEG 1000-PEG 6000) is preferably added in concentration of about 10% to about 80%. Cell fusion can be carried out efficiently by incubating a mixture of both cells at about 20° C. to about 40° C., preferably about 30° C. to about 37° C. for about 1 minute to 10 minutes.

Various methods may be used for screening for a hybridoma producing the antibody (e.g., against a tumor antigen or autoantibody of the present invention). For example, where a supernatant of the hybridoma is added to a solid phase (e.g., microplate) to which antibody is adsorbed directly or together with a carrier and then an anti-immunoglobulin antibody (if mouse cells are used in cell fusion, anti-mouse immunoglobulin antibody is used) or Protein A labeled with a radioactive substance or an enzyme is added to detect the monoclonal antibody against the protein bound to the solid phase. Alternately, a supernatant of the hybridoma is added to a solid phase to which an anti-immunoglobulin antibody or Protein A is adsorbed and then the protein labeled with a radioactive substance or an enzyme is added to detect the monoclonal antibody against the protein bound to the solid phase.

Selection of the monoclonal antibody can be carried out according to any known method or its modification. Normally, a medium for animal cells to which HAT (hypoxanthine, aminopterin, thymidine) are added is employed. Any selection and growth medium can be employed as long as the hybridoma can grow. For example, RPMI 1640 medium containing 1% to 20%, preferably 10% to 20% fetal bovine serum, GIT medium containing 1% to 10% fetal bovine serum, a serum free medium for cultivation of a hybridoma (SFM-101, Nissui Seiyaku) and the like can be used. Normally, the cultivation is carried out at 20° C. to 40° C., preferably 37° C. for about 5 days to 3 weeks, preferably 1 week to 2 weeks under about 5% $CO_2$ gas. The antibody titer of the supernatant of a hybridoma culture can be measured according to the same manner as described above with respect to the antibody titer of the anti-protein in the antiserum.

Separation and purification of a monoclonal antibody (e.g., against secretory vimentin of the present invention) can be carried out according to the same manner as those of conventional polyclonal antibodies such as separation and purification of immunoglobulins, for example, salting-out, alcoholic precipitation, isoelectric point precipitation, electrophoresis, adsorption and desorption with ion exchangers (e.g., DEAE), ultracentrifugation, gel filtration, or a specific purification method wherein only an antibody is collected with an active adsorbent such as an antigen-binding solid phase, Protein A or Protein G and dissociating the binding to obtain the antibody.

Polyclonal antibodies may be prepared by any known method or modifications of these methods including obtaining antibodies from patients. For example, a complex of an immunogen (an antigen against the protein) and a carrier protein is prepared and an animal is immunized by the complex according to the same manner as that described with respect to the above monoclonal antibody preparation. A material containing the antibody against is recovered from the immunized animal and the antibody is separated and purified.

As to the complex of the immunogen and the carrier protein to be used for immunization of an animal, any carrier protein and any mixing proportion of the carrier and a hapten can be employed as long as an antibody against the hapten, which is crosslinked on the carrier and used for immunization, is produced efficiently. For example, bovine serum albumin, bovine cycloglobulin, keyhole limpet hemocyanin, etc. may be coupled to an hapten in a weight ratio of about 0.1 part to about 20 parts, preferably, about 1 part to about 5 parts per 1 part of the hapten.

In addition, various condensing agents can be used for coupling of a hapten and a carrier. For example, glutaraldehyde, carbodiimide, maleimide activated ester, activated ester reagents containing thiol group or dithiopyridyl group, and the like find use with the present invention. The condensation product as such or together with a suitable carrier or diluent is administered to a site of an animal that permits the antibody production. For enhancing the antibody production capability, complete or incomplete Freund's adjuvant may be administered. Normally, the protein is administered once every 2 weeks to 6 weeks, in total, about 3 times to about 10 times.

The polyclonal antibody is recovered from blood, ascites and the like, of an animal immunized by the above method. The antibody titer in the antiserum can be measured according to the same manner as that described above with respect to the supernatant of the hybridoma culture. Separation and purification of the antibody can be carried out according to the same separation and purification method of immunoglobulin as that described with respect to the above monoclonal antibody.

The protein used herein as the immunogen is not limited to any particular type of immunogen. For example, a vimentin fragment of the present invention can be used as the immunogen. Further, fragments of the protein may be used. Fragments may be obtained by any methods including, but not limited to expressing a fragment of the gene, enzymatic processing of the protein, chemical synthesis, and the like.

III. Secretory Vimentin Antisense Oligonucleotides

In some embodiments, the present invention targets the expression of secreted vimentin. For example, in some embodiments, the present invention employs compositions comprising oligomeric antisense compounds, particularly oligonucleotides (e.g., those identified in the drug screening methods described above), for use in modulating the function of nucleic acid molecules encoding extracellular vimentin of the present invention, ultimately modulating the amount of secretory vimentin expressed. This is accomplished by providing antisense compounds that specifically hybridize with one or more nucleic acids encoding secretory vimentin of the present invention. The specific hybridization of an oligomeric compound with its target nucleic acid interferes with the normal function of the nucleic acid. This modulation of function of a target nucleic acid by compounds that specifically hybridize to it is generally referred to as "antisense." The functions of DNA to be interfered with include replication and transcription. The functions of RNA to be interfered with include all vital functions such as, for example, translocation of the RNA to the site of protein translation, translation of protein from the RNA, splicing of the RNA to yield one or more mRNA species, and catalytic activity that may be engaged in or facilitated by the RNA. The overall effect of such interference with target nucleic acid function is modulation of the expression of secreted vimentin of the present invention. In the context of the present invention, "modulation" means either an increase (stimulation) or a decrease (inhibition) in the expression of a gene. For example, expression may be inhibited to potentially prevent vimentin secretion.

It is preferred to target specific nucleic acids for antisense. "Targeting" an antisense compound to a particular nucleic acid, in the context of the present invention, is a multistep process. The process usually begins with the identification of a nucleic acid sequence whose function is to be modulated. This may be, for example, a cellular gene (or mRNA transcribed from the gene) whose expression is associated with a particular disorder or disease state, or a nucleic acid molecule from an infectious agent. In the present invention, the target is a nucleic acid molecule encoding extracellular vimentin of the present invention. The targeting process also includes determination of a site or sites within this gene for the antisense interaction to occur such that the desired effect, e.g., detection or modulation of expression of the protein, will result. Within the context of the present invention, a preferred intragenic site is the region encompassing the translation initiation or termination codon of the open reading frame (ORF) of the gene. Since the translation initiation codon is typically 5'-AUG (in transcribed mRNA molecules; 5'-ATG in the corresponding DNA molecule), the translation initiation codon is also referred to as the "AUG codon," the "start codon" or the "AUG start codon". A minority of genes have a translation initiation codon having the RNA sequence 5'-GUG, 5'-UUG or 5'-CUG, and 5'-AUA, 5'-ACG and 5'-CUG have been shown to function in vivo. Thus, the terms "translation initiation codon" and "start codon" can encompass many codon sequences, even though the initiator amino acid in each instance is typically methionine (in eukaryotes) or formylmethionine (in prokaryotes). Eukaryotic and prokaryotic genes may have two or more alternative start codons, any one of which may be preferentially utilized for translation initiation in a particular cell type or tissue, or under a particular set of conditions. In the context of the present invention, "start codon" and "translation initiation codon" refer to the codon or codons that are used in vivo to initiate translation of an mRNA molecule transcribed from a gene encoding a tumor antigen of the present invention, regardless of the sequence(s) of such codons.

Translation termination codon (or "stop codon") of a gene may have one of three sequences (i.e., 5'-UAA, 5'-UAG and 5'-UGA; the corresponding DNA sequences are 5'-TAA, 5'-TAG and 5'-TGA, respectively). The terms "start codon region" and "translation initiation codon region" refer to a portion of such an mRNA or gene that encompasses from about 25 to about 50 contiguous nucleotides in either direction (i.e., 5' or 3') from a translation initiation codon. Similarly, the terms "stop codon region" and "translation termination codon region" refer to a portion of such an mRNA or gene that encompasses from about 25 to about 50 contiguous nucleotides in either direction (i.e., 5' or 3') from a translation termination codon.

The open reading frame (ORF) or "coding region," which refers to the region between the translation initiation codon and the translation termination codon, is also a region that may be targeted effectively. Other target regions include the 5' untranslated region (5' UTR), referring to the portion of an mRNA in the 5' direction from the translation initiation codon, and thus including nucleotides between the 5' cap site and the translation initiation codon of an mRNA or corresponding nucleotides on the gene, and the 3' untranslated region (3' UTR), referring to the portion of an mRNA in the 3' direction from the translation termination codon, and thus including nucleotides between the translation termination codon and 3' end of an mRNA or corresponding nucleotides on the gene. The 5' cap of an mRNA comprises an N7-methylated guanosine residue joined to the 5'-most residue of the mRNA via a 5'-5' triphosphate linkage. The 5' cap region of an mRNA is considered to include the 5' cap structure itself as well as the first 50 nucleotides adjacent to the cap. The cap region may also be a preferred target region.

Although some eukaryotic mRNA transcripts are directly translated, many contain one or more regions, known as "introns," that are excised from a transcript before it is translated. The remaining (and therefore translated) regions are known as "exons" and are spliced together to form a continuous mRNA sequence. mRNA splice sites (i.e., intron-exon junctions) may also be preferred target regions, and are particularly useful in situations where aberrant splicing is implicated in disease, or where an overproduction of a particular mRNA splice product is implicated in disease. Aberrant fusion junctions due to rearrangements or deletions are also preferred targets. It has also been found that introns can also be effective, and therefore preferred, target regions for antisense compounds targeted, for example, to DNA or pre-mRNA.

In some embodiments, target sites for antisense inhibition are identified using commercially available software programs (e.g., Biognostik, Gottingen, Germany; SysArris Software, Bangalore, India; Antisense Research Group, University of Liverpool, Liverpool, England; GeneTrove, Carlsbad, Calif.). In other embodiments, target sites for antisense inhibition are identified using the accessible site method described in U.S. Patent WO0198537A2, herein incorporated by reference.

Once one or more target sites have been identified, oligonucleotides are chosen that are sufficiently complementary to the target (i.e., hybridize sufficiently well and with sufficient specificity) to give the desired effect. For example, in preferred embodiments of the present invention, antisense oligonucleotides are targeted to or near the start codon.

In the context of this invention, "hybridization," with respect to antisense compositions and methods, means hydrogen bonding, which may be Watson-Crick, Hoogsteen or reversed Hoogsteen hydrogen bonding, between complementary nucleoside or nucleotide bases. For example, adenine and thymine are complementary nucleobases that pair through the formation of hydrogen bonds. It is understood that the sequence of an antisense compound need not be 100% complementary to that of its target nucleic acid to be specifically hybridizable. An antisense compound is specifically hybridizable when binding of the compound to the target DNA or RNA molecule interferes with the normal function of the target DNA or RNA to cause a loss of utility, and there is a sufficient degree of complementarity to avoid non-specific binding of the antisense compound to non-target sequences under conditions in which specific binding is desired (i.e., under physiological conditions in the case of in vivo assays or therapeutic treatment, and in the case of in vitro assays, under conditions in which the assays are performed).

Antisense compounds are commonly used as research reagents and diagnostics. For example, antisense oligonucleotides, which are able to inhibit gene expression with specificity, can be used to elucidate the function of particular genes. Antisense compounds are also used, for example, to distinguish between functions of various members of a biological pathway.

The specificity and sensitivity of antisense is also applied for therapeutic uses. For example, antisense oligonucleotides have been employed as therapeutic moieties in the treatment of disease states in animals and man. Antisense oligonucleotides have been safely and effectively administered to humans and numerous clinical trials are presently underway. It is thus established that oligonucleotides are useful therapeutic modalities that can be configured to be useful in treatment regimes for treatment of cells, tissues, and animals, especially humans.

While antisense oligonucleotides are a preferred form of antisense compound, the present invention comprehends other oligomeric antisense compounds, including but not limited to oligonucleotide mimetics such as are described below. The antisense compounds in accordance with this invention preferably comprise from about 8 to about 30 nucleobases (i.e., from about 8 to about 30 linked bases), although both longer and shorter sequences may find use with the present invention. Particularly preferred antisense compounds are antisense oligonucleotides, even more preferably those comprising from about 12 to about 25 nucleobases.

Specific examples of preferred antisense compounds useful with the present invention include oligonucleotides containing modified backbones or non-natural internucleoside linkages. As defined in this specification, oligonucleotides having modified backbones include those that retain a phosphorus atom in the backbone and those that do not have a phosphorus atom in the backbone. For the purposes of this specification, modified oligonucleotides that do not have a phosphorus atom in their internucleoside backbone can also be considered to be oligonucleosides.

Preferred modified oligonucleotide backbones include, for example, phosphorothioates, chiral phosphorothioates, phosphorodithioates, phosphotriesters, aminoalkylphosphotriesters, methyl and other alkyl phosphonates including 3'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates having normal 3'-5' linkages, 2'-5' linked analogs of these, and those having inverted polarity wherein the adjacent pairs of nucleoside units are linked 3'-5' to 5'-3' or 2'-5' to 5'-2'. Various salts, mixed salts and free acid forms are also included.

Preferred modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); sloganeer backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

In other preferred oligonucleotide mimetics, both the sugar and the internucleoside linkage (i.e., the backbone) of the nucleotide units are replaced with novel groups. The base units are maintained for hybridization with an appropriate nucleic acid target compound. One such oligomeric compound, an oligonucleotide mimetic that has been shown to have excellent hybridization properties, is referred to as a peptide nucleic acid (PNA). In PNA compounds, the sugar-backbone of an oligonucleotide is replaced with an amide containing backbone, in particular an aminoethylglycine backbone. The nucleobases are retained and are bound directly or indirectly to aza nitrogen atoms of the amide portion of the backbone. Representative United States patents that teach the preparation of PNA compounds include, but are not limited to, U.S. Pat. Nos.: 5,539,082; 5,714,331; and 5,719,262, each of which is herein incorporated by reference. Further teaching of PNA compounds can be found in Nielsen et al., Science 254:1497 (1991).

Most preferred embodiments of the invention are oligonucleotides with phosphorothioate backbones and oligonucleosides with heteroatom backbones, and in particular —$CH_2$—, —NH—O—$CH_2$—, —$CH_2$—N($CH_3$)—O—$CH_2$— [known as a methylene (methylimino) or MMI backbone], —$CH_2$—O—N($CH_3$)—$CH_2$—, —$CH_2$—N($CH_3$)—N($CH_3$)—$CH_2$—, and —O—N($CH_3$)—$CH_2$—$CH_2$— [wherein the native phosphodiester backbone is represented as —O—P—O—$CH_2$—] of the above referenced U.S. Pat. No. 5,489,677, and the amide backbones of the above referenced U.S. Pat. No. 5,602,240. Also preferred are oligonucleotides having morpholino backbone structures of the above-referenced U.S. Pat. No. 5,034,506.

Modified oligonucleotides may also contain one or more substituted sugar moieties. Preferred oligonucleotides comprise one of the following at the 2' position: OH; F; O—, S—, or N-alkyl; O—, S—, or N-alkenyl; O—, S— or N-alkynyl; or O-alkyl-O-alkyl, wherein the alkyl, alkenyl and alkynyl may be substituted or unsubstituted $C_1$ to $C_{10}$ alkyl or $C_2$ to $C_{10}$ alkenyl and alkynyl. Particularly preferred are O[($CH_2$)$_n$O]$_m$$CH_3$, O($CH_2$)$_n$O$CH_3$, O($CH_2$)$_n$$NH_2$, O($CH_2$)$_n$$CH_3$, O($CH2$)$_n$O$NH_2$, and O($CH_2$)$_n$ON[($CH_2$)$_n$$CH_3$)]$_2$, where n and m are from 1 to about 10. Other preferred oligonucleotides comprise one of the following at the 2' position: $C_1$ to $C_{10}$ lower alkyl, substituted lower alkyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. A preferred modification includes 2'-methoxyethoxy (2'-O—$CH_2CH_2OCH_3$, also known as 2'-O-(2-methoxyethyl) or 2'-MOE) (Martin et al., Helv. Chim. Acta 78:486 [1995]) i.e., an alkoxyalkoxy group. A further preferred modification includes 2'-dimethylamninooxyethoxy (i.e., a O($CH_2$)$_2$ON($CH_3$)$_2$ group), also known as 2'-DMAOE, and 2'-dimethylaminoethoxyethoxy (also known in the art as 2'-O-dimethylaminoethoxyethyl or 2'-DMAEOE), i.e., 2'-O—$CH_2$—O—$CH_2$—N($CH_3$)$_2$.

Other preferred modifications include 2'-methoxy(2'-O—$CH_3$), 2'-aminopropoxy(2'-O$CH_2CH_2CH_2NH_2$) and 2'-fluoro (2'-F). Similar modifications may also be made at other positions on the oligonucleotide, particularly the 3' position of the sugar on the 3' terminal nucleotide or in 2'-5' linked oligonucleotides and the 5' position of 5' terminal nucleotide. Oligonucleotides may also have sugar mimetics such as cyclobutyl moieties in place of the pentofuranosyl sugar.

Oligonucleotides may also include nucleobase (often referred to in the art simply as "base") modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 8-azaguanine and 8-azaadenine, 7-deazaguanine and 7-deazaadenine and 3-deazaguanine and 3-deazaadenine. Further nucleobases include those disclosed in U.S. Pat. No. 3,687,808. Certain of these nucleobases are particularly useful for increasing the binding affinity of the oligomeric compounds of the invention. These include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6-1.2. degree ° C. and are presently preferred base substitutions, even more particularly when combined with 2'-O-methoxyethyl sugar modifications.

Another modification of the oligonucleotides of the present invention involves chemically linking to the oligonucleotide one or more moieties or conjugates that enhance the activity, cellular distribution or cellular uptake of the oligonucleotide. Such moieties include but are not limited to lipid moieties such as a cholesterol moiety, cholic acid, a thioether, (e.g., hexyl-S-tritylthiol), a thiocholesterol, an aliphatic chain, (e.g., dodecandiol or undecyl residues), a phospholipid, (e.g., di-hexadecyl-rac-glycerol or triethylammonium 1,2-di-O-hexadecyl-rac-glycero-3-H-phosphonate), a polyamine or a polyethylene glycol chain or adamantane acetic acid, a palmityl moiety, or an octadecylamine or hexylamino-carbonyl-oxycholesterol moiety.

One skilled in the relevant art knows well how to generate oligonucleotides containing the above-described modifications. The present invention is not limited to the antisense oligonucleotides described above. Any suitable modification or substitution may be utilized.

It is not necessary for all positions in a given compound to be uniformly modified, and in fact more than one of the aforementioned modifications may be incorporated in a single compound or even at a single nucleoside within an oligonucleotide. The present invention also includes antisense compounds that are chimeric compounds. "Chimeric" antisense compounds or "chimeras," in the context of the present invention, are antisense compounds, particularly oligonucleotides, which contain two or more chemically distinct regions, each made up of at least one monomer unit, i.e., a nucleotide in the case of an oligonucleotide compound. These oligonucleotides typically contain at least one region wherein the oligonucleotide is modified so as to confer upon the oligonucleotide-increased resistance to nuclease degradation, increased cellular uptake, and/or increased binding affinity for the target nucleic acid. An additional region of the oligonucleotide may serve as a substrate for enzymes capable of cleaving RNA:DNA or RNA:RNA hybrids. By way of example, RNaseH is a cellular endonuclease that cleaves the RNA strand of an RNA:DNA duplex. Activation of RNase H, therefore, results in cleavage of the RNA target, thereby greatly enhancing the efficiency of oligonucleotide inhibition of gene expression. Consequently, comparable results can often be obtained with shorter oligonucleotides when chimeric oligonucleotides are used, compared to phosphorothioate deoxyoligonucleotides hybridizing to the same target region. Cleavage of the RNA target can be routinely detected by gel electrophoresis and, if necessary, associated nucleic acid hybridization techniques known in the art.

Chimeric antisense compounds of the present invention may be formed as composite structures of two or more oligonucleotides, modified oligonucleotides, oligonucleosides and/or oligonucleotide mimetics as described above.

The present invention also includes pharmaceutical compositions and formulations that include the antisense compounds of the present invention as described below.

IV. Secretory Vimentin RNA Interference (RNAi)

RNAi represents an evolutionary conserved cellular defense for controlling the expression of foreign genes in most eukaryotes, including humans. RNAi is triggered by double-stranded RNA (dsRNA) and causes sequence-specific mRNA degradation of single-stranded target RNAs homologous in response to dsRNA. The mediators of mRNA degradation are small interfering RNA duplexes (siRNAs), which are normally produced from long dsRNA by enzymatic cleavage in the cell. siRNAs are generally approximately twenty-one nucleotides in length (e.g. 21-23 nucleotides in length), and have a base-paired structure characterized by two nucleotide 3'-overhangs. Following the introduction of a small RNA, or RNAi, into the cell, it is believed the sequence is delivered to an enzyme complex called RISC (RNA-induced silencing complex). RISC recognizes the target and cleaves it with an endonuclease. It is noted that if larger RNA sequences are delivered to a cell, RNase III enzyme (Dicer) converts longer dsRNA into 21-23 nt ds siRNA fragments.

Chemically synthesized siRNAs have become powerful reagents for genome-wide analysis of mammalian gene function in cultured somatic cells. Beyond their value for validation of gene function, siRNAs also hold great potential as gene-specific therapeutic agents (Tuschl and Borkhardt, Molecular Intervent. 2002; 2(3):158-67, herein incorporated by reference).

The transfection of siRNAs into animal cells results in the potent, long-lasting post-transcriptional silencing of specific genes (Caplen et al, Proc Natl Acad Sci U.S.A. 2001; 98: 9742-7; Elbashir et al., Nature. 2001; 411:4948; Elbashir et al., Genes Dev. 2001; 15: 188-200; and Elbashir et al., EMBO J. 2001; 20: 6877-88, all of which are herein incorporated by reference). Methods and compositions for performing RNAi with siRNAs are described, for example, in U.S. Pat. No. 6,506,559, herein incorporated by reference.

siRNAs are effective at lowering the amounts of targeted RNA, and by extension proteins, frequently to undetectable levels. The silencing effect can last several months, and is highly specific, because one nucleotide mismatch between the target RNA and the central region of the siRNA is frequently sufficient to prevent silencing Brummelkamp et al, Science 2002; 296:550-3; and Holen et al, Nucleic Acids Res. 2002; 30:1757-66, both of which are herein incorporated by reference.

A. RNAi for Vimentin

As discussed above, the present invention provides RNAi for inhibiting the expression of the vimentin. Preferably, inhibition of the level of vimentin expression in cells, such as the MDM of a patient, prevents and/or reduces the symptoms of infectious disease, such as sepsis.

B. Designing and Testing RNAi for Vimentin

In order to design siRNAs for vimentin (e.g. that target vimentin mRNA) software design tools are available in the art (e.g. on the internet). For example, Oligoengine's web page has one such design tool that finds RNAi candidates based on Elbashir's (Elbashir, 2002) criteria. Other design tools may also be used, such as the Cenix Bioscience design tool offered by Ambion. In addition, there is also the Si2 silencing duplex offered by Oligoengine.

There are also RNA folding software programs available that allow one to determine if the mRNA has a tendency to fold on its own and form a "hair-pin" (which in the case of dsRNAi is not as desirable since one goal is to have the RNAi attach to the mRNA and not itself). One preferred configuration is an open configuration with three or less bonds. Generally, a positive delta G is desirable to show that it would not tend to fold on itself spontaneously. siRNA candidate molecules that are generated can be, for example, screened in an animal model of sepsis for the quantitative evaluation of vimentin expression in vivo using similar techniques as described above.

C. Expression Cassettes

Vimentin specific siRNAs of the present invention may be synthesized chemically. Chemical synthesis can be achieved by any method known or discovered in the art. Alternatively, vimentin specific siRNAs of the present invention may be synthesized by methods that comprise synthesis by transcription. In some embodiments, transcription is in vitro, as from a DNA template and bacteriophage RNA polymerase promoter, in other embodiments, synthesis is in vivo, as from a gene and a promoter. Separate-stranded duplex siRNA, where the two strands are synthesized separately and annealed, can also be synthesized chemically by any method known or discovered in the art. Alternatively, ds siRNA are synthesized by methods that comprise synthesis by transcription. In some embodiments, the two strands of the double-stranded region of a siRNA are expressed separately by two different expression cassettes, either in vitro (e.g., in a transcription system) or in vivo in a host cell, and then brought together to form a duplex.

Thus, in another aspect, the present invention provides a composition comprising an expression cassette comprising a promoter and a gene that encodes a siRNA specific for vimentin. In some embodiments, the transcribed siRNA forms a single strand of a separate-stranded duplex (or double-stranded, or ds) siRNA of about 18 to 25 base pairs long; thus, formation of ds siRNA requires transcription of each of the two different strands of a ds siRNA. The term "gene" in the expression cassette refers to a nucleic acid sequence that comprises coding sequences necessary for the production of a siRNA. Thus, a gene includes but is not limited to coding sequences for a strand of a ds siRNA.

Generally, a DNA expression cassette comprises a chemically synthesized or recombinant DNA molecule containing at least one gene, or desired coding sequence for a single strand of a ds siRNA, and appropriate nucleic acid sequences necessary for the expression of the operably linked coding sequence, either in vitro or in vivo. Expression in vitro may include expression in transcription systems and in transcription/ translation systems. Expression in vivo may include expression in a particular host cell and/or organism. Nucleic acid sequences necessary for expression in a prokaryotic cell or in a prokaryotic in vitro expression system are well known and usually include a promoter, an operator, and a ribosome binding site, often along with other sequences. Eukaryotic in vitro transcription systems and cells are known to utilize promoters, enhancers, and termination and polyadenylation signals. Nucleic acid sequences necessary for expression via bacterial RNA polymerases (such as T3, T7, and SP6), referred to as a transcription template in the art, include a template DNA strand which has a polymerase promoter region followed by the complement of the RNA sequence desired (or the coding sequence or gene for the siRNA). In order to create a transcription template, a complementary strand is annealed to the promoter portion of the template strand.

In any of the expression cassettes described above, the gene may encode a transcript that contains at least one cleavage site, such that when cleaved results in at least two cleavage products. Such products can include the two opposite strands of a ds siRNA. In an expression system for expression in a eukaryotic cell, the promoter may be constitutive or inducible; the promoter may also be tissue or organ specific (e.g. specific to the immune system), or specific to a developmental phase. Preferably, the promoter is positioned 5' to the transcribed region. Other promoters are also contemplated; such promoters include other polymerase III promoters and microRNA promoters.

Preferably, a eukaryotic expression cassette further comprises a transcription termination signal suitable for use with the promoter; for example, when the promoter is recognized by RNA polymerase III, the termination signal is an RNA polymerase III termination signal. The cassette may also include sites for stable integration into a host cell genome.

D. Vectors

In other aspects of the present invention, the compositions comprise a vector comprising a gene encoding an siRNA specific for vimentin or preferably at least one expression cassette comprising a promoter and a gene which encodes a sequence necessary for the production of a siRNA specific for vimentin (an siRNA gene). The vectors may further comprise marker genes, reporter genes, selection genes, or genes of interest, such as experimental genes. Vectors of the present invention include cloning vectors and expression vectors. Expression vectors may be used in in vitro transcription/ translation systems, as well as in in vivo in a host cell. Expression vectors used in vivo in a host cell may be transfected into a host cell, either transiently, or stably. Thus, a vector may also include sites for stable integration into a host cell genome.

In some embodiments, it is useful to clone a siRNA gene downstream of a bacteriophage RNA polymerase promoter into a multicopy plasmid. A variety of transcription vectors containing bacteriophage RNA polymerase promoters (such as T7 promoters) are available. Alternatively, DNA synthesis can be used to add a bacteriophage RNA polymerase promoter upstream of a siRNA coding sequence. The cloned plasmid DNA, linearized with a restriction enzyme, can then be used as a transcription template (See for example Milligan, J F and Uhlenbeck, O C (1989) Methods in Enzymology 180: 51-64).

In other embodiments of the present invention, vectors include, but are not limited to, chromosomal, nonchromosomal and synthetic DNA sequences (e.g., derivatives of viral DNA such as vaccinia, adenovirus, fowl pox virus, and pseudorabies). It is contemplated that any vector may be used as long as it is expressed in the appropriate system (either in vitro or in vivo) and viable in the host when used in vivo; these two criteria are sufficient for transient transfection. For stable transfection, the vector is also replicable in the host.

Large numbers of suitable vectors are known to those of skill in the art, and are commercially available. In some embodiments of the present invention, mammalian expression vectors comprise an origin of replication, suitable promoters and enhancers, and also any necessary ribosome binding sites, polyadenylation sites, splice donor and acceptor sites, transcriptional termination sequences, and 5' flanking non-transcribed sequences. In other embodiments, DNA sequences derived from the SV40 splice, and polyadenylation sites may be used to provide the required non-transcribed genetic elements.

In certain embodiments of the present invention, a gene sequence in an expression vector which is not part of an expression cassette comprising a siRNA gene (specific for vimentin) is operatively linked to an appropriate expression control sequence(s) (promoter) to direct mRNA synthesis. In some embodiments, the gene sequence is a marker gene or a selection gene. Promoters useful in the present invention include, but are not limited to, the cytomegalovirus (CMV) immediate early, herpes simplex virus (HSV) thymidine kinase, and mouse metallothionein promoters and other promoters known to control expression of gene in mammalian cells or their viruses. In other embodiments of the present invention, recombinant expression vectors include origins of replication and selectable markers permitting transformation of the host cell (e.g., dihydrofolate reductase or neomycin resistance for eukaryotic cell culture).

In some embodiments of the present invention, transcription of DNA encoding a gene is increased by inserting an enhancer sequence into the vector. Enhancers are cis-acting elements of DNA, usually about from 10 to 300 bp that act on a promoter to increase its transcription. Enhancers useful in the present invention include, but are not limited to, a cytomegalovirus early promoter enhancer, the polyoma enhancer on the late side of the replication origin, and adenovirus enhancers.

Preferably the design of a vector is configured to deliver the RNAi for more permanent inhibition. For example the pSilencer siRNA expression vector offered by Ambion, the pSuper RNAi system offered by Oligoengine, and the GneSilencer System offered by IMGENEX. These are all plasmid vector based RNAis. BD Biosciences offer the RNAi-Ready pSIREN Vectors, that allow both a Plasmid-based vectors and an Adenoviral or a Retroviral delivery formats. Ambion is expected to release an adenoviral vector for siRNA shortly. For the design of a vector there is no limitation regarding the folding pattern since there is no concern regarding the formation of a hairpin or at least there are no studies that found any difference in performance related to the mRNA folding pattern. It is noted that Ambion offers a design tool for a vector on their web page, and BD Biosciences offers a manual for the design of a vector, both of which are useful for designing vectors for siRNA.

E. Cell Transfection

In yet other aspects, the present invention provides compositions comprising cells transfected by an expression cassette of the present invention as described above, or by a vector of the present invention, where the vector comprises an expression cassette (or simply the siRNA gene) of the present invention, as described above. In some embodiments of the present invention, the host cell is a mammalian cell. A transfected cell may be a cultured cell or a tissue, organ, or organismal cell. Specific examples of cultured host cells include, but are not limited to, Chinese hamster ovary (CHO) cells, COS-7 lines of monkey kidney fibroblasts, 293T, C127, 3T3, HeLa, orbital fibroblasts, BHK cell lines, and lymphocytes (e.g., T-lymphocytes). Specific examples of host cells in vivo include monocytes, monocyte-derived macrophages, and lymphocytes.

The cells may be transfected transiently or stably (e.g. DNA expressing the siRNA is stably integrated and expressed by the host cell's genome). The cells may also be transfected with an expression cassette of the present invention, or they are transfected with an expression vector of the present invention. In some embodiments, transfected cells are cultured mammalian cells, preferably human cells. In other embodiments, they are tissue, organ, or organismal cells (e.g. monocytes or monocyte-derived macrophages).

In the present invention, cells to be transfected in vitro are typically cultured prior to transfection according to methods that are well known in the art, as for example by the preferred methods as defined by the American Tissue Culture Collection. In certain embodiments of the present invention, cells are transfected with siRNAs that are synthesized exogenously (or in vitro, as by chemical methods or in vitro transcription methods), or they are transfected with expression cassettes or vectors, which express siRNAs within the transfected cell.

In some embodiments, cells are transfected with siRNAs by any method known or discovered in the art that allows a cell to take up exogenous RNA and remain viable. Non-limiting examples include electroporation, microinjection, transduction, cell fusion, DEAE dextran, calcium phosphate precipitation, use of a gene gun, osmotic shock, temperature shock, and electroporation, and pressure treatment. In alternative, embodiments, the siRNAs are introduced in vivo by lipofection, as has been reported (as, for example, by Elbashir et al. (2001) Nature 411: 494-498, herein incorporated by reference).

In other embodiments expression cassettes or vectors comprising at least one expression cassette are introduced into the desired host cells by methods known in the art, including but not limited to transfection, electroporation, microinjection, transduction, cell fusion, DEAE dextran, calcium phosphate precipitation, use of a gene gun, or use of a DNA vector transporter (See e.g., Wu et al. (1992) J. Biol. Chem., 267: 963; Wu and Wu (1988) J. Biol. Chem., 263:14621; and Williams et al. (1991) Proc. Natl. Acad. Sci. USA 88:272). Receptor-mediated DNA delivery approaches are also used (Curiel et al. (1992) Hum. Gene Ther., 3:147; and Wu and Wu (1987) J. Biol. Chem., 262:4429). In some embodiments, various methods are used to enhance transfection of the cells. These methods include but are not limited to osmotic shock, temperature shock, and electroporation, and pressure treatment.

Alternatively, the vector can be introduced in vivo by lipofection. For the past decade, there has been increasing use of liposomes for encapsulation and transfection of nucleic acids in vitro. Synthetic cationic lipids designed to limit the difficulties and dangers encountered with liposome-mediated transfection can be used to prepare liposomes for in vivo transfection of a gene encoding a marker. The use of cationic lipids may promote encapsulation of negatively charged nucleic acids, and also promote fusion with negatively charged cell membranes. Particularly useful lipid compounds and compositions for transfer of nucleic acids are described in WO95/18863 and WO96/17823, and in U.S. Pat. No. 5,459,127, herein incorporated by reference. Other molecules are also useful for facilitating transfection of a nucleic acid in vivo, such as a cationic oligopeptide (e.g., WO95/21931), peptides derived from DNA binding proteins (e.g., WO96/25508), or a cationic polymer (e.g., WO95/21931).

It is also possible to introduce a sequence encoding a siRNA in vivo as a naked DNA, either as an expression cassette or as a vector. Methods for formulating and administering naked DNA to mammalian muscle tissue are disclosed in U.S. Pat. Nos. 5,580,859 and 5,589,466, both of which are herein incorporated by reference.

Stable transfection typically requires the presence of a selectable marker in the vector used for transfection. Transfected cells are then subjected to a selection procedure. Generally, selection involves growing the cells in a toxic substance, such as G418 or Hygromycin B, such that only those cells expressing a transfected marker gene conferring resistance to the toxic substance upon the transfected cell survive and grow. Such selection techniques are well known in the art. Typical selectable markers are well known, and include genes encoding resistance to G418 or hygromycin B.

In preferred embodiments, the transfecting agent is OLIGOFECTAMINE. OLIGOFECTAMINE is a lipid based transfection reagent. Additional example of lipid based transfection reagents that were designed for the transfection of dsRNAis are the Transit-TKO reagent which is provided by Mirus (Madison, Wis.), and the jetSI which was introduced by Polyplus-trasfection SAS. In addition, the Silencer siRNA Transfection Kit provided by Ambion's includes siPORT Amine and siPORT Lipid transfection agents. Roche offers the Fugene 6 transfection reagents that are also lipid based. There is an option to use electroporation in cell culture. Preferably a plasmid vector delivery system is transfected into the cell with OLIGOFECTAMINE provided by Invitrogen or with siPORT XP-1 transfection agent provided by Ambion.

In certain embodiments, certain chemical modifications of the dsRNAis such as changing the lipophilicity of the molecule may be employed (e.g., attachment of lipophilic residues at the 3' termini of the dsRNA). Delivery of dsRNAs into organisms may also be achieved with methods previously developed for the application of antisense oligonucleotides such as injection of liposomes-encapsulated molecules.

F. Kits

The present invention also provides kits comprising at least one expression cassette comprising a siRNA gene specific for vimentin. In some aspects, a transcript from the expression cassette forms a double stranded siRNA of about 18 to 25 base pairs long. In other embodiments, the expression cassette is contained within a vector, as described above, where the vector can be used in in vitro transcription or transcription/translation systems, or used in vivo to transfect cells, either transiently or stably.

In other aspects, the kit comprises at least two expression cassettes, each of which comprises a siRNA gene, such that at least one gene encodes one strand of a siRNA that combines with a strand encoded by a second cassette to form a ds siRNA; the ds siRNA so produced is any of the embodiments described above. These cassettes may comprise a promoter and a sequence encoding one strand of a ds siRNA. In some further embodiments, the two expression cassettes are present in a single vector; in other embodiments, the two expression cassettes are present in two different vectors. A vector with at least one expression cassette, or two different vectors, each comprising a single expression cassette, can be used in in vitro transcription or transcription/translation systems, or used in vivo to transfect cells, either transiently or stably.

In yet other aspects, the kit comprises at least one expression cassettes which comprises a gene which encodes two separate strands of a ds siRNA and a processing site between the sequences encoding each strand such that, when the gene is transcribed, the transcript is processed, such as by cleavage, to result in two separate strands which can combine to form a ds siRNA, as described above.

In some embodiments, the present invention provides kits comprising; a) a composition comprising small interfering RNA duplexes (siRNAs) configured to inhibit expression of vimentin protein, and b) printed material with instructions for employing the composition for treating a target cell expressing vimentin protein via expression of vimentin mRNA under conditions such that the vimentin mRNA is cleaved or otherwise disabled. In certain embodiments, the printed material comprises instructions for employing the composition for treating infectious diseases.

G. Generating Vimentin Specific siRNA

The present invention also provides methods of synthesizing siRNAs specific for vimentin (e.g., human vimentin). The siRNAs may be synthesized in vitro or in vivo. In vitro synthesis includes chemical synthesis and synthesis by in vitro transcription. In vitro transcription is achieved in a transcription system, as from a bacteriophage RNA polymerase, or in a transcription/translation system, as from a eukaryotic RNA polymerase. In vivo synthesis occurs in a transfected host cell.

The siRNAs synthesized in vitro, either chemically or by transcription, are used to transfect cells. Therefore, the present invention also provides methods of transfecting host cells with siRNAs synthesized in vitro; in particular embodiments, the siRNAs are synthesized by in vitro transcription. The present invention further provides methods of silencing the vimentin gene in vivo by transfecting cells with siRNAs synthesized in vitro. In other methods, the siRNAs is expressed in vitro in a transcription/translation system from an expression cassette or expression vector, along with an expression vector encoding and expressing a reporter gene.

The present invention also provides methods of expressing siRNAs in vivo by transfecting cells with expression cassettes or vectors that direct synthesis of siRNAs in vivo. The present invention also provides methods of silencing genes in vivo by transfecting cells with expression cassettes or vectors that direct synthesis of siRNAs in vivo H. Therapeutic Applications The present invention also provides methods and compositions suitable for gene therapy to alter gene expression, production, or function (e.g. to treat a human patient with infectious disease). As described above, the present invention provides compositions comprising expression cassettes comprising a gene encoding a siRNA specific for vimentin, and vectors comprising such expression cassettes.

Viral vectors commonly used for in vivo or ex vivo targeting and therapy procedures are generally DNA-based vectors and retroviral vectors. Methods for constructing and using viral vectors are known in the art (See e.g., Miller and Rosman (1992) BioTech., 7:980-990, herein incorporated by reference). Preferably, the viral vectors are replication defective, that is, they are unable to replicate autonomously in the target cell. In general, the genome of the replication defective viral vectors lacks at least one region that is necessary for the replication of the virus in the infected cell. These regions can either be eliminated (in whole or in part), or be rendered non-functional by any technique known to a person skilled in the art. These techniques include the total removal, substitution (by other sequences, in particular by the inserted nucleic acid), partial deletion or addition of one or more bases to an essential (for replication) region. Such techniques may be performed in vitro (i.e., on the isolated DNA) or in situ, using the techniques of genetic manipulation or by treatment with mutagenic agents.

Preferably, the replication defective virus retains the sequences of its genome that are necessary for encapsidating the viral particles. DNA viral vectors include an attenuated or defective DNA viruses, including, but not limited to, herpes simplex virus (HSV), papillomavirus, Epstein Barr virus (EBV), adenovirus, adeno-associated virus (AAV), and the like. Defective viruses, that entirely or almost entirely lack viral genes, are preferred, as defective virus is not infective after introduction into a cell. Use of defective viral vectors allows for administration to cells in a specific, localized area (such as, for example, transcutaneous or operative administration to immune tissue), without concern that the vector can infect other cells. Thus, a specific tissue can be specifically targeted. Examples of particular vectors include, but are not limited to, a defective herpes virus 1 (HSV1) vector (Kaplitt et al. (1991) Mol. Cell. Neurosci., 2:320-330), defective herpes virus vector lacking a glycoprotein L gene (See e.g., Patent Publication RD 371005 A), or other defective herpes virus vectors (See e.g., WO 94/21807; and WO 92/05263); an attenuated adenovirus vector, such as the vector described by Stratford-Perricaudet et al. ((1992) J. Clin. Invest., 90:626-630; See also, La Salle et al. (1993) Science 259:988-990); and a defective adeno-associated virus vector (Samulski et al. (1987) J. Virol., 61:3096-3101; Samulski et al. (1989) J. Virol., 63:3822-3828; and Lebkowski et al. (1988) Mol. Cell. Biol., 8:3988-3996).

Preferably, for in vivo administration, an appropriate immunosuppressive treatment is employed in conjunction with the viral vector (e.g., adenovirus vector), to avoid immuno-deactivation of the viral vector and transfected cells. For example, immunosuppressive cytokines, such as interleukin-12 (IL-12), interferon-gamma (IFN-γ), or anti-CD4 antibody, can be administered to block humoral or cellular immune responses to the viral vectors. In addition, it is advantageous to employ a viral vector that is engineered to express a minimal number of antigens.

In some embodiments, the vector is an adenovirus vector. Adenoviruses are eukaryotic DNA viruses that can be modified to efficiently deliver a nucleic acid of the invention to a variety of cell types. Various serotypes of adenovirus exist. Of these serotypes, type 2 or type 5 human adenoviruses (Ad 2 or Ad 5), or adenoviruses of animal origin (See e.g., WO 94/26914) are preferred. Examples of useful adenoviruses of animal origin include adenoviruses of canine, bovine, murine (e.g., Mav1, Beard et al., Virol. (1990) 75-81), ovine, porcine, avian, and simian (e.g., SAV) origin.

Preferably, the replication defective adenoviral vectors of the invention comprise the ITRs, an encapsidation sequence and the nucleic acid of interest. Still more preferably, at least the E1 region of the adenoviral vector is non-functional. The deletion in the E1 region preferably extends from nucleotides 455 to 3329 in the sequence of the Ad5 adenovirus (PvuII-BglII fragment) or 382 to 3446 (HinfII-Sau3A fragment). Other regions may also be modified, in particular the E3 region (e.g., WO 95/02697), the E2 region (e.g., WO 94/28938), the E4 region (e.g., WO 94/28152, WO 94/12649 and WO 95/02697), or in any of the late genes L1-L5.

In particular embodiments, the adenoviral vector has a deletion in the E1 region (Ad 1.0). Examples of E1-deleted adenoviruses are disclosed in EP 185,573, the contents of which are incorporated herein by reference. In another embodiment, the adenoviral vector has a deletion in the E1 and E4 regions (Ad 3.0). Examples of E1/E4-deleted adenoviruses are disclosed in WO 95/02697 and WO 96/22378. In still another embodiment, the adenoviral vector has a deletion in the E1 region into which the E4 region and the nucleic acid sequence are inserted.

The replication defective recombinant adenoviruses according to the invention can be prepared by any technique known to the person skilled in the art (See e.g., Levrero et al. (1991) Gene 101:195; EP 185 573; and Graham (1984) EMBO J., 3:2917). In particular, they can be prepared by homologous recombination between an adenovirus and a plasmid that carries, inter alia, the DNA sequence of interest (e.g. the sequence encoding the siRNA specific for vimentin). The homologous recombination is accomplished following co-transfection of the adenovirus and plasmid into an appropriate cell line. The cell line that is employed should preferably (i) be transformable by the elements to be used, and (ii) contain the sequences that are able to complement the part of the genome of the replication defective adenovirus, preferably in integrated form in order to avoid the risks of recombination. Examples of cell lines that may be used are the human embryonic kidney cell line 293 (Graham et al. (1977) J. Gen. Virol., 36:59), which contains the left-hand portion of the genome of an Ad5 adenovirus (12%) integrated into its genome, and cell lines that are able to complement the E1 and E4 functions, as described in applications WO 94/26914 and WO 95/02697. Recombinant adenoviruses are recovered and purified using standard molecular biological techniques that are well known to one of ordinary skill in the art.

The adeno-associated viruses (AAV) are DNA viruses of relatively small size that can integrate, in a stable and site-specific manner, into the genome of the cells that they infect. They are able to infect a wide spectrum of cells without inducing effects on cellular growth, morphology or differentiation, and they do not appear to be involved in human pathologies. The AAV genome has been cloned, sequenced and characterized. It encompasses approximately 4700 bases and contains an inverted terminal repeat (ITR) region of approximately 145 bases at each end, which serves as an origin of replication for the virus. The remainder of the genome is divided into two essential regions that carry the encapsidation functions: the left-hand part of the genome, that contains the rep gene involved in viral replication and expression of the viral genes; and the right-hand part of the genome, that contains the cap gene encoding the capsid proteins of the virus.

The use of vectors derived from the AAVs for transferring genes in vitro and in vivo has been described (See e.g., WO 91/18088; WO 93/09239; U.S. Pat. No. 4,797,368; U.S. Pat. No., 5,139,941; and EP 488 528, all of which are herein incorporated by reference). These publications describe various AAV-derived constructs in which the rep and/or cap genes are deleted and replaced by a gene of interest, and the use of these constructs for transferring the gene of interest in vitro (into cultured cells) or in vivo (directly into an organism). The replication defective recombinant AAVs according to the invention can be prepared by co-transfecting a plasmid containing the nucleic acid sequence of interest flanked by two AAV inverted terminal repeat (ITR) regions, and a plasmid carrying the AAV encapsidation genes (rep and cap genes), into a cell line that is infected with a human helper virus (for example an adenovirus). The AAV recombinants that are produced are then purified by standard techniques.

In another embodiment, the gene can be introduced in a retroviral vector (e.g., as described in U.S. Pat. Nos. 5,399,346, 4,650,764, 4,980,289 and 5,124,263; all of which are herein incorporated by reference; Mann et al. (1983) Cell 33:153; Markowitz et al. (1988) J. Virol., 62:1120; WO 95/07358; and Kuo et al. (1993) Blood 82:845). The retroviruses are integrating viruses that infect dividing cells. The retrovirus genome includes two LTRs, an encapsidation sequence and three coding regions (gag, pol and env). In recombinant retroviral vectors, the gag, pol and env genes are generally deleted, in whole or in part, and replaced with a heterologous nucleic acid sequence of interest. These vectors can be constructed from different types of retrovirus, such as, HIV, MoMuLV ("murine Moloney leukemia virus" MSV ("murine Moloney sarcoma virus"), HaSV ("Harvey sarcoma virus"); SNV ("spleen necrosis virus"); RSV ("*Rous sarcoma virus*") and Friend virus. Defective retroviral vectors are also disclosed in WO 95/02697. In preferred embodiments, the retrovirus (or other vector) allows the siRNA gene to integrate into the host cells genome (thus being expressed by the cell and the cell's progeny).

In general, in order to construct recombinant retroviruses containing a nucleic acid sequence, a plasmid is constructed that contains the LTRs, the encapsidation sequence and the coding sequence. This construct is used to transfect a packaging cell line, which cell line is able to supply in trans the retroviral functions that are deficient in the plasmid. In general, the packaging cell lines are thus able to express the gag, pol and env genes. Such packaging cell lines have been described in the prior art, in particular the cell line PA317 (U.S. Pat. No. 4,861,719, herein incorporated by reference), the PsiCRIP cell line (See, WO90/02806), and WO89/07150). In addition, the recombinant retroviral vectors can contain modifications within the LTRs for suppressing transcriptional activity as well as extensive encapsidation sequences that may include a part of the gag gene (Bender et al. (1987) J. Virol., 61:1639). Recombinant retroviral vectors are purified by standard techniques known to those having ordinary skill in the art. In some embodiments, retroviral vectors encode siRNAs with strand specificity; this avoids self-targeting of the viral genomic RNA; in particular embodiments, the retroviral vector comprise a U6 promoter (Ilves, H. et al. (1996) Gene 171, 203-8).

In certain embodiments, cells are taken from a patient and transfected (transiently or stably) and then reintroduced into the patient. In particular embodiments, the cells reintroduced into the patient have the siRNA gene integrated into their genome.

In some embodiments, as certain dsRNA are base-labile with a propensity to hydrolyze in aqueous media, the RNAi-based drug is delivered using a polymer-based delivery mechanism. Examples are the products provided by Skin Visible. In some embodiments, for the delivery into the in vivo cell (the cytoplasm) as a drug, the Polymer Vector delivery may be used with or without the attachment of inactivated viruses. In some embodiments, the siRNA (e.g. polymer vector) may be delivered via, for example, systemic application.

In certain preferred embodiments, a slow drug release options such as the "Encapsulated Cell Technology" (from Neurotech) or other slow release systems that will be placed potentially in the bloodstream is used to treat a patient with siRNA duplexes (or vectors encoding the same) that target vimentin. However, other systemic applications may also be employed to deliver the siRNA or vectors encoding siRNA specific for vimentin. The present invention also includes pharmaceutical compositions and formulations that include the siRNA compounds of the present invention as described below.

V. Secretory Vimentin Pharmaceutical Compositions

The present invention further provides pharmaceutical compositions that may comprise peptide inhibitors and activators of secretory vimentin, alone or in combination with at least one other agent, such as a stabilizing compound, and may be administered in any sterile, biocompatible pharmaceutical carrier, including, but not limited to, saline, buffered saline, dextrose, and water.

The methods of the present invention find use in treating diseases or altering physiological states characterized by abnormal bioavailability of secretory vimentin. The present invention provides a method for inhibiting inflammation, comprising providing a subject, and one or more compounds that decrease the bioavailability of secretory vimentin, and administering to the subject one or more said compounds. In some embodiments the compound decreases vimentin secretion. In another embodiment, the compound increases secretory vimentin metabolism. In a preferred embodiment the compound comprises a proteinase.

For example, peptides can be administered to the patient intravenously in a pharmaceutically acceptable carrier such as physiological saline. Standard methods for intracellular delivery of peptides can be used (e.g., delivery via liposome). Such methods are well known to those of ordinary skill in the art. The formulations of this invention are useful for parenteral administration, such as intravenous, subcutaneous, intramuscular, and intraperitoneal. Therapeutic administration of a polypeptide intracellularly can also be accomplished using gene therapy as described above.

As is well known in the medical arts, dosages for any one patient depends upon many factors, including the patient's size, body surface area, age, the particular compound to be administered, sex, time and route of administration, general health, genetic susceptibilities, and interaction with other drugs being concurrently administered.

Accordingly, in some embodiments of the present invention, peptides can be administered to a patient alone, or in combination with drugs or hormones or in pharmaceutical compositions where they are mixed with excipient(s) or other pharmaceutically acceptable carriers. In one embodiment of the present invention, the pharmaceutically acceptable carrier is pharmaceutically inert. In another embodiment of the present invention, peptides may be administered alone to individuals subject to or suffering from a disease.

Depending on the condition being treated, these pharmaceutical compositions may be formulated and administered systemically or locally. Techniques for formulation and administration may be found in the latest edition of "Remington's Pharmaceutical Sciences" (Mack Publishing Co, Easton Pa.). Suitable routes may, for example, include oral or transmucosal administration; as well as parenteral delivery, including intramuscular, subcutaneous, intramedullary, intrathecal, intraventricular, intravenous, intraperitoneal, or intranasal administration.

For injection, the pharmaceutical compositions of the invention may be formulated in aqueous solutions, preferably in physiologically compatible buffers such as Hanks' solution, Ringer's solution, or physiologically buffered saline. For tissue or cellular administration, penetrants appropriate to the particular barrier to be permeated are used in the formulation. Such penetrants are generally known in the art.

In other embodiments, the pharmaceutical compositions of the present invention can be formulated using pharmaceutically acceptable carriers well known in the art in dosages suitable for oral administration. Such carriers enable the pharmaceutical compositions to be formulated as tablets, pills, capsules, liquids, gels, syrups, slurries, suspensions and the like, for oral or nasal ingestion by a patient to be treated.

Pharmaceutical compositions suitable for use in the present invention include compositions wherein the active ingredients are contained in an effective amount to achieve the intended purpose. For example, an effective amount of vimentin inhibitor peptide may be that amount that increases an oxidative burst. Determination of effective amounts is well within the capability of those skilled in the art, especially in light of the disclosure provided herein.

In addition to the active ingredients these pharmaceutical compositions may contain suitable pharmaceutically acceptable carriers comprising excipients and auxiliaries that facilitate processing of the active compounds into preparations that can be used pharmaceutically. The preparations formulated for oral administration may be in the form of tablets, dragees, capsules, or solutions.

The pharmaceutical compositions of the present invention may be manufactured in a manner that is itself known (e.g., by means of conventional mixing, dissolving, granulating, dragee-making, levigating, emulsifying, encapsulating, entrapping or lyophilizing processes).

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances that increase the viscosity of the suspension, such as sodium carboxymethyl cellulose, sorbitol, or dextran. Optionally, the suspension may also contain suitable stabilizers or agents that increase the solubility of the compounds to allow for the preparation of highly concentrated solutions.

Pharmaceutical preparations for oral use can be obtained by combining the active compounds with solid excipient, optionally grinding a resulting mixture, and processing the mixture of granules, after adding suitable auxiliaries, if desired, to obtain tablets or dragee cores. Suitable excipients are carbohydrate or protein fillers such as sugars, including lactose, sucrose, mannitol, or sorbitol; starch from corn, wheat, rice, potato, etc; cellulose such as methyl cellulose, hydroxypropylmethyl-cellulose, or sodium carboxymethyl-cellulose; and gums including arabic and tragacanth; and proteins such as gelatin and collagen. If desired, disintegrating or solubilizing agents may be added, such as the cross-linked polyvinyl pyrrolidone, agar, alginic acid or a salt thereof such as sodium alginate.

Dragee cores are provided with suitable coatings such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compounds, (i.e., dosage).

Pharmaceutical preparations that can be used orally include push-fit capsules made of gelatin, as well as soft, sealed capsules made of gelatin and a coating such as glycerol or sorbitol. The push-fit capsules can contain the active ingredients mixed with fillers or binders such as lactose or starches, lubricants such as talc or magnesium stearate, and, optionally, stabilizers. In soft capsules, the active compounds may be dissolved or suspended in suitable liquids, such as fatty oils, liquid paraffin, or liquid polyethylene glycol with or without stabilizers.

Compositions comprising a compound of the invention formulated in a pharmaceutical acceptable carrier may be prepared, placed in an appropriate container, and labeled for treatment of an indicated condition. For peptide inhibitors of secretory vimentin, conditions indicated on the label may include treatment of conditions related to abnormal secretory vimentin activity.

The pharmaceutical composition may be provided as a salt and can be formed with many acids, including but not limited to hydrochloric, sulfuric, acetic, lactic, tartaric, malic, succinic, etc. Salts tend to be more soluble in aqueous or other protonic solvents that are the corresponding free base forms. In other cases, the preferred preparation may be a lyophilized powder in 1 mM-50 mM histidine, 0.1%-2% sucrose, 2%-7% mannitol at a pH range of 4.5 to 5.5 that is combined with buffer prior to use.

For any compound used in the method of the invention, the therapeutically effective dose can be estimated initially from cell culture assays. Then, preferably, dosage can be formulated in animal models (particularly murine models) to achieve a desirable circulating concentration range.

A therapeutically effective dose refers to that amount of peptide that ameliorates symptoms of the disease state. Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index, and it can be expressed as the ratio $LD_{50}/ED_{50}$. Compounds that exhibit large therapeutic indices are preferred. The data obtained from these cell culture assays and additional animal studies can be used in formulating a range of dosage for human use. The dosage of such compounds lies preferably within a range of circulating concentrations that include the $ED_{50}$ with little or no toxicity. The dosage varies within this range depending upon the dosage form employed, sensitivity of the patient, and the route of administration.

The exact dosage is chosen by the individual physician in view of the patient to be treated. Dosage and administration are adjusted to provide sufficient levels of the active moiety or to maintain the desired effect. Additional factors which may be taken into account include the severity of the disease state; age, weight, and gender of the patient; diet, time and frequency of administration, drug combination(s), reaction sensitivities, and tolerance/response to therapy. Long acting pharmaceutical compositions might be administered every 3 to 4 days, every week, or once every two weeks depending on half-life and clearance rate of the particular formulation.

Normal dosage amounts may vary from 0.1 to 100,000 micrograms, up to a total dose of about I g, depending upon the route of administration. Guidance as to particular dosages and methods of delivery is provided in the literature (See e.g., U.S. Pat. Nos. 4,657,760; 5,206,344; or 5,225,212, all of which are herein incorporated by reference). Administration to the bone marrow may necessitate delivery in a manner different from intravenous injections.

This invention further pertains to novel agents identified by the above-described screening assays. Accordingly, it is within the scope of this invention to further use an agent identified as described herein (e.g., an anti-vimentin antibody, a vimentin antisense oligonucleotide, a vimentin siRNA, a secretory vimentin peptide mimetic) in an appropriate animal model (such as those described herein) to determine the efficacy, toxicity, side effects, or mechanism of action, of treatment with such an agent. Furthermore, novel agents identified by the above-described screening assays can be, e.g., used for treatments as described herein.

Experimental

Below are examples of specific embodiments for carrying out the present invention. The examples are offered for illustrative purposes only and are not intended to limit the scope of the present invention in any way. In the experimental disclosure which follows, the following abbreviations apply: M (molar); mM (millimolar); µM (micromolar); nM (nanomolar); mol (moles); mmol (millimoles); µmol (micromoles); nmol (nanomoles); gm (grams); mg (milligrams); µg (micrograms); pg (picograms); L (liters); ml (milliliters); µl (microliters); cm (centimeters); mm (millimeters); µm (micrometers); nm (nanometers); ° C. (degrees Centigrade).

Methods

Cell Preparation

Monocyte-derived macrophages (MDMs) were prepared as previously described[40]. Briefly, heparinized venous blood was collected upon consent from healthy volunteers, and peripheral blood mononuclear cells (PBMC) were separated by Ficoll-Hypaque (Pharmacia Biotech AB, Uppsala, Sweden) density gradient centrifugation. MDM were purified by adherence to plastic for 2 h at 3 °C. at a concentration of $5 \times 10^5$ ml$^{-1}$. Adherent cells were consistently >90% monocytes as described[40]. Adherence-purified human monocytes were cultured in X-vivo medium supplemented with 40% human AB serum (Bio-Whittaker, Walkersville, Md.) and 100 units of penicillin and 50 units of streptomycin per ml[12].

Immunohistochemistry

Cells were cultured using a glass chamber slide system (Nalge Nunc International, Naperville, Ill.). Cultures were washed with PBS and fixed for 10 min at 4° C. with PBS containing 4% paraformaldehyde. Cells were washed again, blocked by incubation for 1 h with 0.2% BSA in PBS, and incubated with mouse monoclonal anti-vimentin V9 (Research Genetics, Inc) diluted 1:100 or goat anti-vimentin (Chemicon International, CA) diluted 1:50 in PBS with 0.1% saponin (permeabilized) or without saponin (non-permeabilized) for 1 h. Slides were rewashed, blocked with goat serum for 1 h, and incubated with 10 µg ml$^{-1}$ Alexa Fluor™ 488 (fluorescein) conjugated to rabbit anti-goat or 594 (rhodamine) conjugated to goat anti-mouse antibody (Molecular Probes, Eugene, Oreg.). The ER was stained with 2.5 µg ml$^{-1}$ rhodamine B hexyl ester (Molecular Probes, Eugene, Oreg.) for 30 min together with the secondary antibody as previously described[41] The Golgi was detected by anti-human golgin-97 mouse monoclonal CDF4 (Molecular Probes) using 2 µg ml$^{-1}$ and 10 µg ml$^{-1}$ Alexa Fluor™ 594 conjugated to goat anti-mouse antibody. Slides were washed, dried and mounted with SlowFade Antifade reagent (Molecular Probes, Eugene, Oreg.). Fluorescence was viewed with a Leitz Orthoplan microscope or Bio-Rad MRC-600 laser scanning confocal microscope using a 40× lens, or 60× using a Zeiss LSM 510 laser scanning microscope. Photographs were taken with a Sony DKC5000, 3CCD RGB camera.

Flow Cytometric Analysis

Six and twelve day human MDM adherent cells were collected by incubation in PBS+10 mM EDTA for 30 min at 4° C. MDM were incubated in staining buffer (DPBS+1% FBS+0.09% sodium azide) with mouse IgG$_{2a}$ for 20 min at 4 °C. to block non-specific binding of IgG to target cells. MDM were then washed with staining buffer and stained for vimentin for 30 min at 4° C. using mouse monoclonal anti-vimentin antibody (Research Genetics, Inc) diluted 1:200, or mouse IgG$_{2a}$ as an isotype control. The cells were washed in staining buffer and incubated with 5 µg ml$^{-1}$ Alexa Fluor™ 488 (fluorescein) conjugated to goat anti-mouse antibody (Molecular Probes, Eugene, Oreg.). Cell-surface expression of vimentin was determined by flow cytometric analysis using an XL Z14107 cytometer. (Becton Dickinson, San Diego, Calif.)

Western Blots

Cells were maintained for 12-48 h in serum-free medium. When applicable, during the incubation in serum-free media cells were treated for 12 h with 10-500 ng ml$^{-1}$ IL-10, 0.5-5 ng ml$^{-1}$ TNF-α, 4 µg ml$^{-1}$ tunicamycin, E-64 [100 M] (Sigma), or 2 or 4 µg ml$^{-1}$ monensin (Pharmingen). Alternatively, cells were treated for 2 h with GÖ 6983 [250 nM], SB 203580 [100 µM], or OA [100 nM] (Calbiochem) followed by 12 h incubation in serum-free media or treatment with TNF-α. The viability of the cells up to 48 h was almost 100% as measured by MTT assay (Boehringer Mannheim, Indianapolis, Ind.) and LDH release as previously described[12]. Supernatants were collected and centrifuged for 20 min at 1500 RPM to remove cell debris and concentrated by a centrifugal filter device (Millipore) in the presence of a protease inhibitor cocktail (Boehringer Mannheim, Indianapolis, Ind.) and were either used immediately or stored at −70° C. Cells were washed and lysed with 1 ml lysis buffer (50 mM Tris pH 7.5, 150 mM NaCl, 1% NP-40 0.1% SDS, 0.5% Na-Deoxycholate and complete EDTA-free protease inhibitor cocktail) was added to the cells and allowed to incubate on ice for 15 min. The lysate was centrifuged at 10,000 rpm for 20 min at 4° C., the supernatant recovered, and the protein extract was either used immediately or stored at −70° C. Equal amounts of protein (20 µg) were loaded under reducing conditions and separated by 10% SDS PAGE. The gel was transferred to nitrocellulose and immunoblotted with mouse monoclonal anti-vimentin antibody V9 (Research Genetics, Inc), goat anti-vimentin antibody (Chemicon International, Calif.) or goat anti-actin (Santa-Cruz Biotechnology, Inc) followed by a horseradish peroxidase-conjugated appropriate secondary antibody. Chemiluminescent signal was detected using the Super Signal West Pico system (Pierce Chemical Co, Rockford, Ill.).

Metabolic Labeling and Immunoprecipitation

Monocytes were washed and pre-incubated in RPMI medium without methionine (Gibco-BRL, Grand Island, N.Y.). Monocytes were then labeled by adding 100 µCi ml$^{-1}$ $^{35}$S methionine (Amersham Pharmacia, Piscataway, N.J.) along with 10% dialyzed AB human serum for 24 h. Medium was removed and replaced by serum free medium for 3-48 h. Supernatant and cell extract were prepared as described above. Vimentin or actin was immunoprecipitated using anti-vimentin or anti-actin antibodies directly conjugated to agarose beads (Santa Cruz). Proteins phosphorylated on serine/threonine residues were immunoprecipitated by polyclonal antibodies specific for phospho-(Ser/Thr) (Cell Signaling). Samples were separated by 10% SDS-PAGE electrophoresis under reducing conditions, and the gel was treated with Amplify fluorographic reagent (Amersham Pharmacia) before autoradiography.

In vivo Phosphorylation of Vimentin 12 day MDM ($1.5 \times 10^6$) were rinsed three times with phosphate-free RPMI medium (Gibco-BRL, Grand Island, N.Y.). Cells were incubated in 5 ml of phosphate-free RPMI media and allowed to equilibrate at 37 °C. in a 6 well plate for 2 h. The media was replaced with 1 ml/well of phosphate-free RPMI media with 10% dialysed human serum and 0.166 mCi of [$^{32}$P] orthophosphoric acid (Amersham Pharmacia Biotech) for 6 h of incubation. In addition to the control, some wells were treated with GÖ 6983 [250 nM] or OA [100 nM]. Following treatment, medium was removed and replaced by serum free medium for 18 h. Supernatant and cells were prepared for immunoprecipitation as described above (Metabolic Labeling section). Phosphorylated vimentin protein was immunoprecipitated as above, and the samples were separated by 10% SDS-PAGE electrophoresis under reducing conditions. Proteins were transferred to nitrocellulose and subjected to autoradiography for 4 h then immunoblotted with mouse monoclonal anti-vimentin antibody (Research Genetics, Inc.), stripped and re-probed with goat polyclonal anti-vimentin antibody (Chemicon International, Calif.), followed by horseradish peroxidase-conjugated goat anti-mouse or rabbit anti-goat secondary antibodies. Chemiluminescent signal was detected using the Super Signal West Pico system (Pierce Chemical Co, Rockford, Ill.).

Oxidative Burst Assay

MDM were plated in 24-well non-tissue culture treated dishes for 10 days in 40% human serum. The MDM were pre-incubated with 180 µg ml$^{-1}$ mouse IgG or 180 µg ml$^{-1}$ anti-vimentin IgG antibody (Sigma) for 12 h. Adherent monocytes (2-5×10$^5$) were detached with PBS containing 5 mM EDTA and 2% inactivated FBS, and incubated at 4° C. for 20 min. Detached monocytes were then collected, washed, and resuspended in DPBS supplemented with glucose (10 mM) and transferred to a 96 well plate. Cells were incubated with 50 µM luminol and 100 nM PMA (Sigma) for 5 min at 37° C. Light emission was measured by Chemiluminescence Microlumat LB 96 P (EG&G Berthold).

Phagocytic and Killing Activity of Macrophages

MDM were plated in 24-well non-tissue culture treated dishes for 10 days in 40% human serum. Cells were pre-incubated with 180 µg ml$^{-1}$ mouse IgG (Sigma) or 180 µg ml$^{-1}$ anti-vimentin IgG antibody (Sigma) for 12 h. The cells were then infected with 1 x 10$^6$ colony forming units of *E. coli* (DH5-α, Gibco-BRL, Grand Island, NY). After 1 h incubation, the wells were extensively washed to remove non-phagocytosed bacteria, and the wells in one plate were lysed with sterile 0.5% TRITON X-100 (polyethylene glycol p-(1, 1,3,3-tetramethylbutyl)-phenyl ether) for the bacterial phago-cytosis assay. Fresh media was added to the other plate and this was incubated for an additional 2 h, after which the cells were lysed with 0.5% TRITON X-100 (polyethylene glycol p-(1,1,3,3-tetramethylbutyl)-phenyl ether) for the bacterial killing assay. Serially diluted cell lysates were plated on agar (Difco, Detroit MI) and incubated overnight at 37° C., and the number of colonies was counted. Killing rate =[1-(CFU at 3h/CFU at 1h)]×100 [42].

EXAMPLE 1

Vimentin is Found on the Surface of Mature MDM

Figure 1:
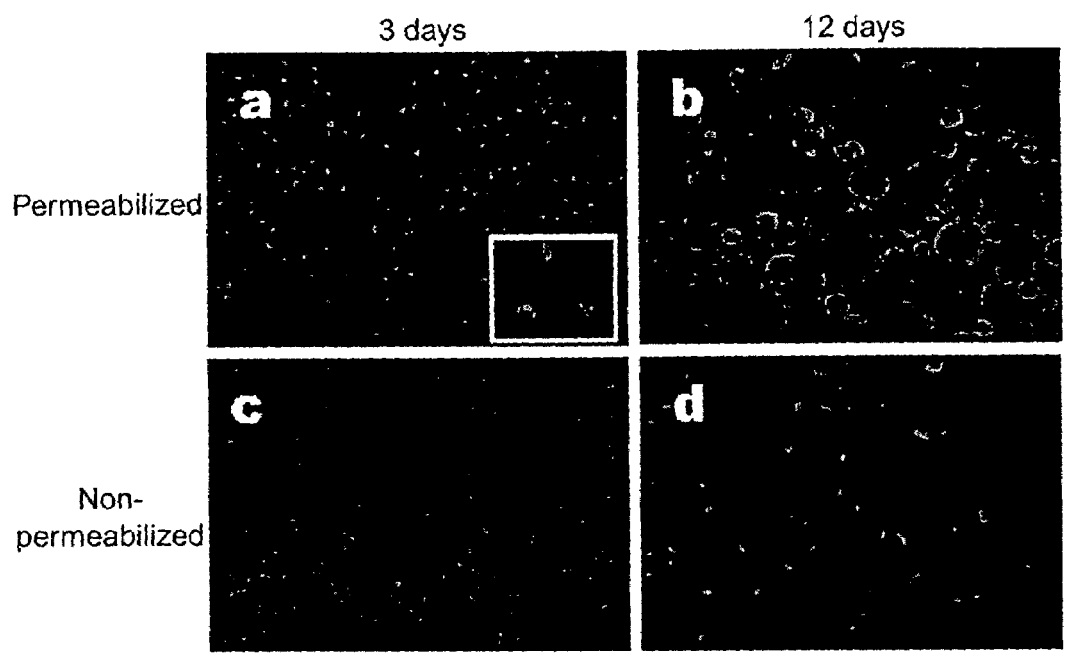
FIG. 1 shows localization of vimentin in human MDM by immunofluorescent staining of 3 day (a and c) or 12 day (b and d) MDM. Permeabilized (a and b), or non-permeabilized (c and d) cells were stained with anti-vimentin (red), and in blue with DAPI to detect nuclei (Magnification, 40×). The inset in (a) is magnified 160×. (e) Flow cytometry shows vimentin on the surface of purified MDM cultured with 40% human serum for six or twelve days. Cells were stained with anti-vimentin (histograms in solid lines) or isotype matched control (histograms in dotted lines). Results presented are representative of three independent experiments.
Figure 1E:
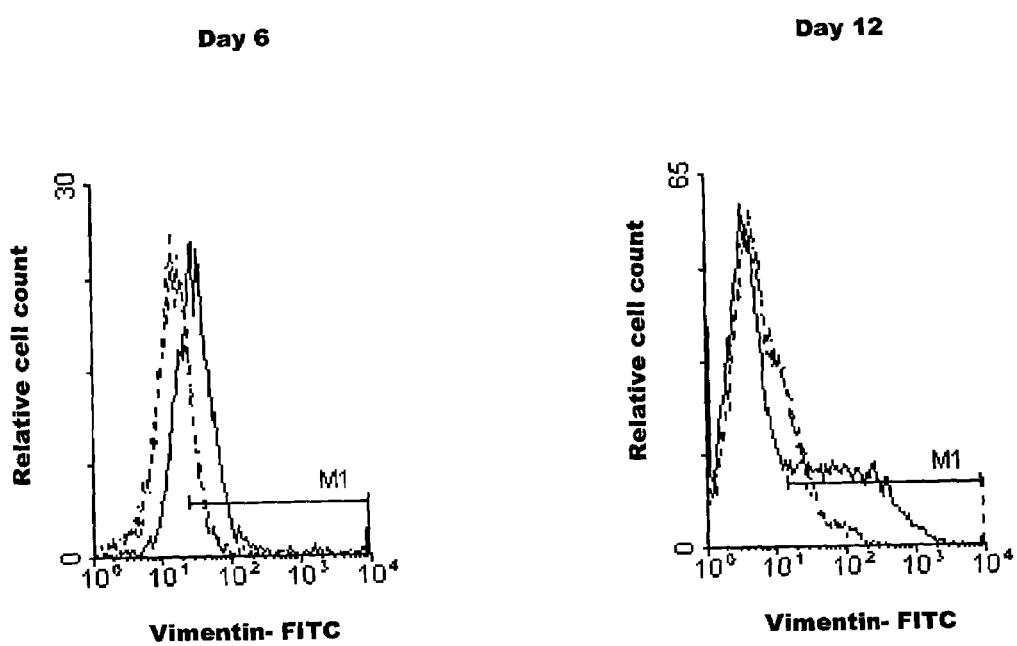

Experiments conducted during the development of the present invention investigated the distribution of vimentin in a model of inflammatory macrophages, in which human monocytes are cultured in 40% human serum and then differentiate over a period of 3-12 days into MDM. These cells become larger in size and develop a destructive phenotype associated with inflammatory disease states in vivo: they secrete enzymatically active forms of the cysteine proteases of the cathepsin family, become multinucleated, and can destroy elastin[11,12]. The distribution of vimentin was examined in these cells by immunofluorescence analysis (FIG. 1). In permeabilized cells[8], on day 3 vimentin had a perinuclear distribution (FIG. 1a, inset). However, by day 12, the pattern of vimentin distribution had changed, with much of the vimentin now concentrated around the plasma membrane (FIG. 1b). In order to assess whether the vimentin seen at the edges of cells could indicate the presence of this protein on the outside of the plasma membrane, immunofluorescence studies were performed on non-permeabilized MDM. Non-permeabilized cells stained positively with anti-vimentin (FIGS. 1c and d), indicating that vimentin was on the outer surface of the cell. Flow cytometry analysis verified the presence of vimentin on the surface of 12 day MDM (FIG. 1e).

EXAMPLE 2

Vimentin is Secreted by Mature MDM

Figure 2G:
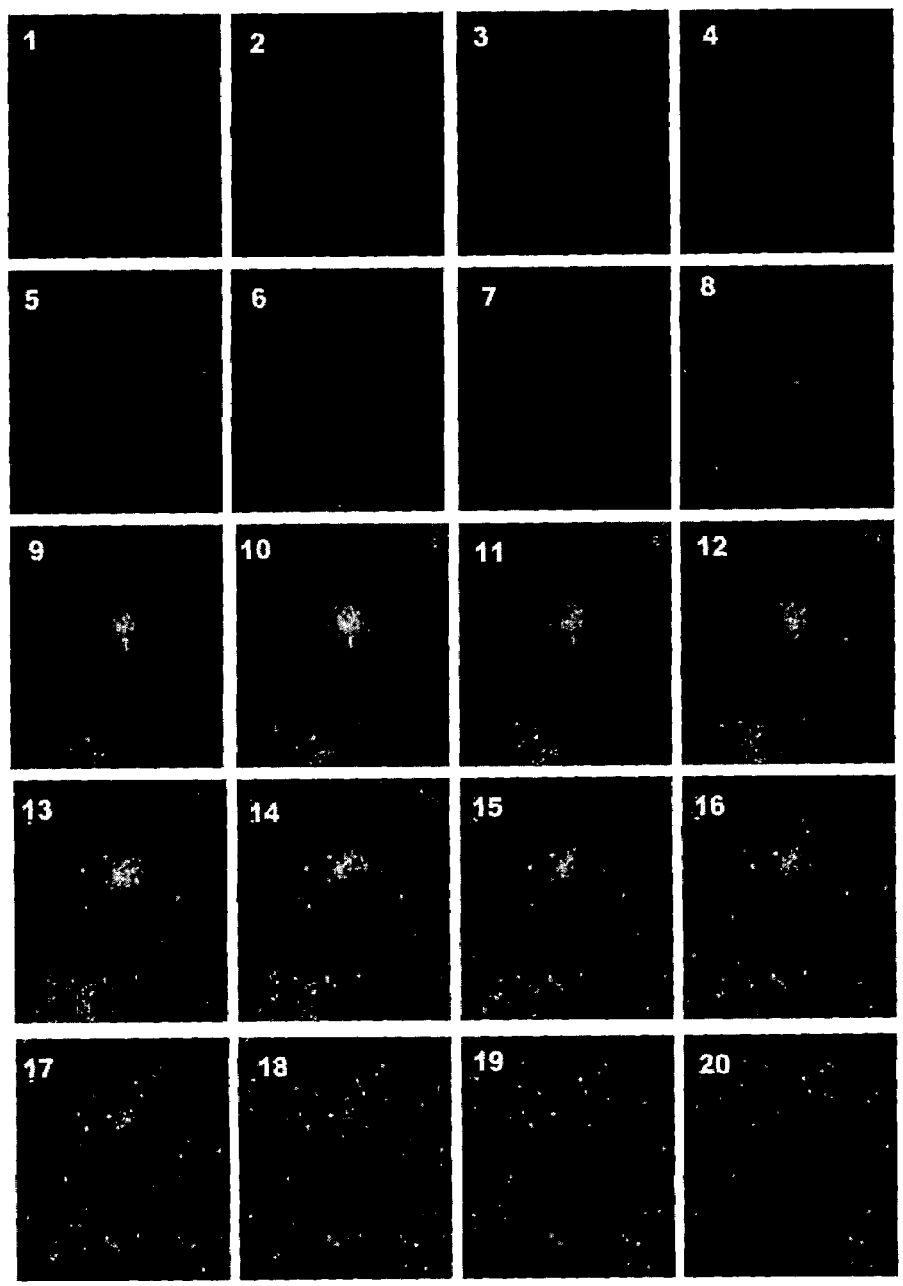
FIG. 2 shows that vimentin is secreted via the classical ER/Golgi pathway, and that secretion is time-dependent and specific. Immunofluorescent staining of 12 day MDM is shown. Confocal microscopy [Magnification, 40× for (a-c); 60× for (d-f)] was used to show staining with anti-vimentin in green (a and d), B hexyl ester in red (detects ER in b), anti-golgin-97 in red (detects Golgi in e), colocalization of (a) and (b) in yellow (c), and colocalization of (d) and (e) in yellow (f). In (g,) (panels 1-20), the colocalization of vimentin and the Golgi (as shown in FIG. 2f) was analyzed by consecutive optical sectioning along the z-axis of 12 day MDM. Pictures were taken by confocal laser-scanning microscopy (magnification 60×) and images along the z-axis from the bottom to the top of the cell with 0.4 μm optical sections are shown. In (h), eleven day MDM were incubated with the Golgi blocker monensin or with the N-glycosylation inhibitor tunicamycin. Secreted vimentin was analyzed in the supernatants by Western blot. The arrows indicate the two main forms of vimentin detected, 62 kD and 52 kD in size.
Figure 2H:
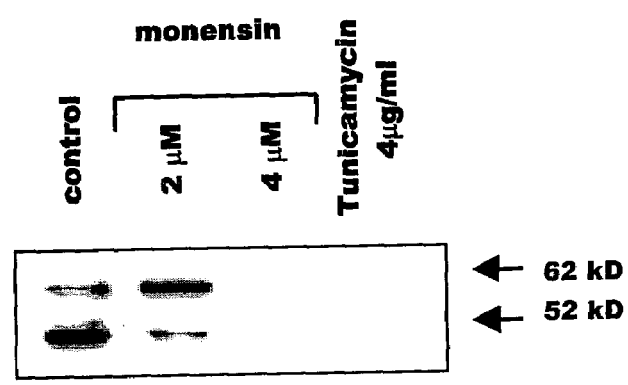

To confirm earlier findings that vimentin can be found in the Golgi and ER[8,14,] immunohistochemical analysis was performed using antibodies to vimentin and ER or Golgi markers. These specific markers detected co-localization between vimentin and the ER (FIG. 2 a-c), as well as between vimentin and the Golgi (FIG. 2 d-f). In order to better address the issue of co-localization, consecutive optical section images were captured along the z-axis of the 12 day MDM preparation (FIG. 2 g). As shown in the figure, this method clearly demonstrated the co-localization of vimentin with the Golgi. This confirms that the co-localization does not result from the presence of vimentin above or below the Golgi body, but in it. When proteins fractionated from supernatants of the 12 day MDM were analyzed by microcapillary mass spectrometry (see Table 1 (SEQ ID NO:1)) and by Western blot analysis with a specific anti-vimentin monoclonal antibody (FIG. 2h), vimentin was readily identified. Full-lenth vimentin is set forth as SEQ ID NO: 1 while amino acid sequence fragments are set forth as SEQ ID NOS:2-8). In order to confirm that vimentin was being actively secreted through the Golgi apparatus, the ability of the Golgi blocker monensin and the glycosylation blocker tunicamycin to inhibit the apparent secretion of vimentin from MDM was tested. Monensin and tunicamycin eliminate secretion of vimentin from the mature MDM as measured by Western blot (FIG. 2h).

Figure 3A:
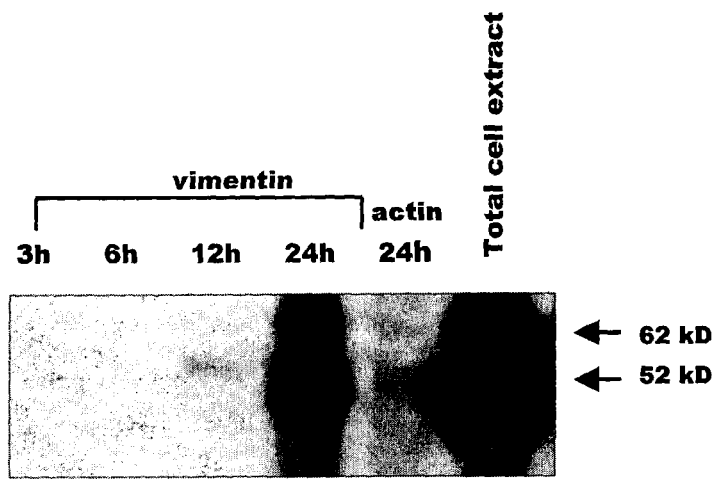
Figure 3B:
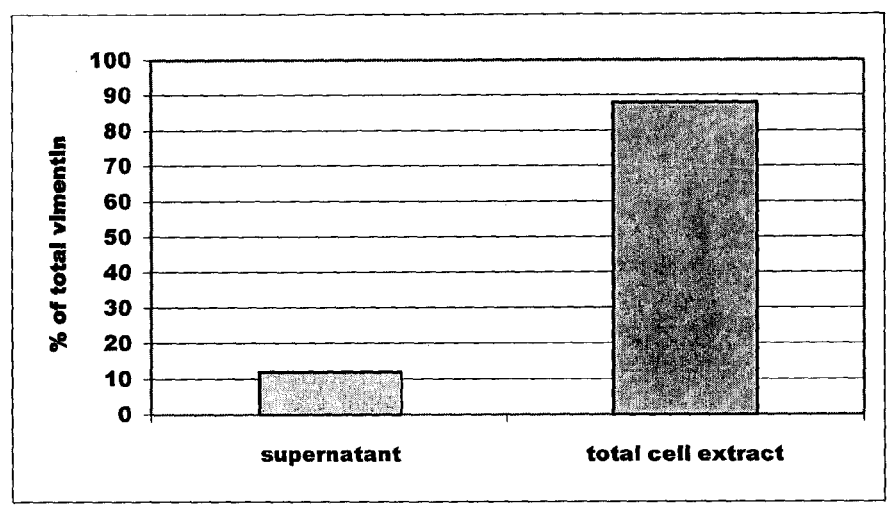

The specificity of vimentin secretion was verified by a combination of pulse-chase/immunoprecipitation experiments using 12 day MDM. As can be seen in FIG. 3a secretion of vimentin was first detected 12 hours after labeling, and was very strong at 24 hours. This was in marked contrast to the yet more abundant cellular protein, actin, which was barely detectable in the supernatants at 24 hours (FIG. 3a, lane 5). Unlike vimentin, another prominent cytoskeletal protein, β-tubulin, was found only in the cytoplasm and not in the supernatants of mature MDM (not shown). Densitometric analysis of a shorter exposure of the autoradiograph shown in FIG. 3a revealed that 12% of the total labeled vimentin was secreted during the 24 h after the chase (FIG. 3b).

Figure 3C:
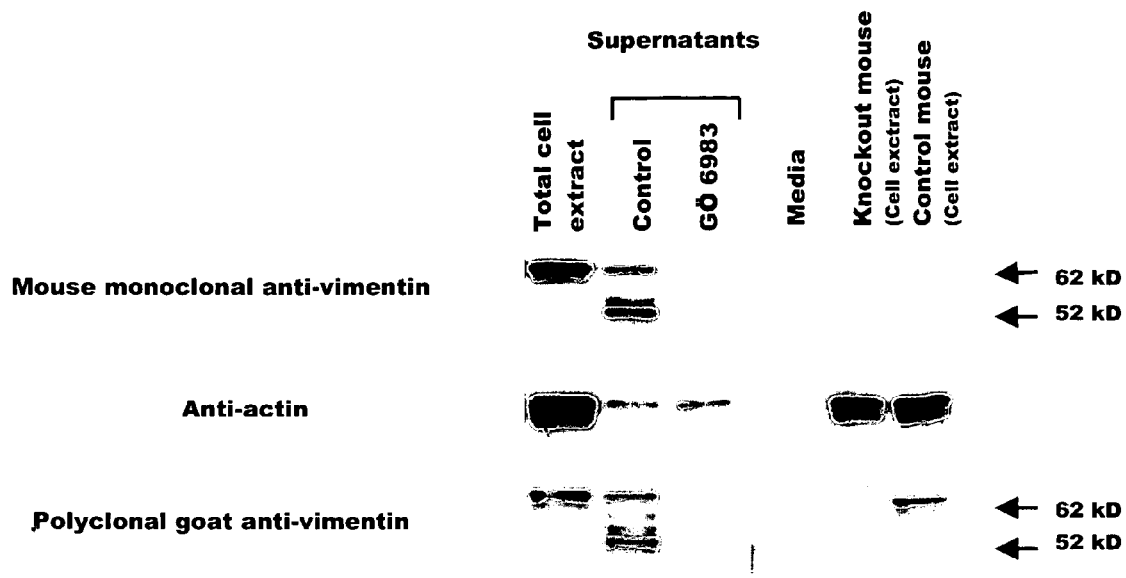
In FIG. 3c, eleven day MDM were incubated with or without the specific PKC inhibitor GÖ6983, and vimentin (top and lower panels) or actin (middle panel) was detected in the supernatants by Western blot analysis. Since the mouse monoclonal antibody (V9) used does not cross-react with murine vimentin, secretion of vimentin was also detected using a goat polyclonal anti-vimentin antibody (bottom panel), demonstrating no detection of vimentin in peritoneal macrophages from vimentin knock-out mice or in serum free media.
Figure 3D:
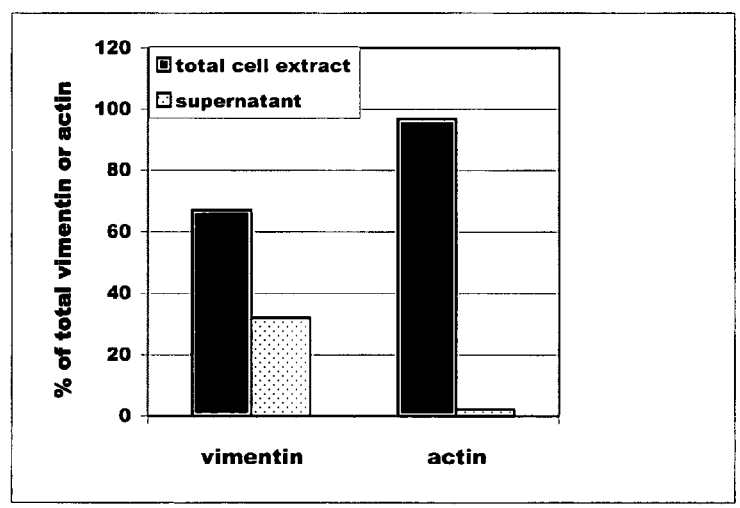
In FIG. 3d, the densitometric quantitation of vimentin compared to actin in the cell and supernatant fractions (as detected in FIG. 3c, top and middle panels, respectively) is shown.

As peripheral blood monocytes are known to acquire resistance to cell death as they mature into MDM, and as 12 day MDM exhibited no increased apoptosis and were equally viable as the 3 day MDM as measured by MTT assay (not shown), the presence of vimentin in the supernatant cannot be attributed simply to cell death. The observed lack of cellular necrosis or apoptosis is further supported by published findings in which extra-cellular LDH was measured to assess the cell viability of MDM cultured using the same technique. These studies also showed that macrophages remain viable past day 12 even when left up to 48 h in the absence of serum[12]. The ratios of vimentin and actin detected in the supernatant to the ones found in the cytoplasm of 12 day MDM were compared using Western Blot analysis. Substantially more vimentin than actin was detected in the supernatant (FIG. 3c-d). Quantification of these signals by densitometry demonstrated that 67% of vimentin is intracellular and 32% is extracellular, while 97.75% of actin is intracellular and 2.25% is extracellular.

Figure 4A:
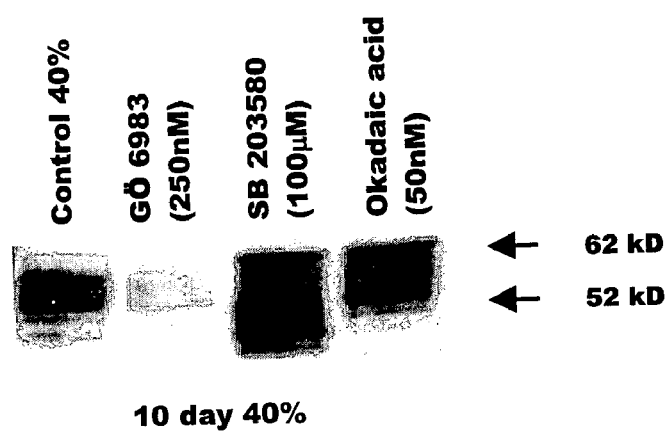
Figure 4B:
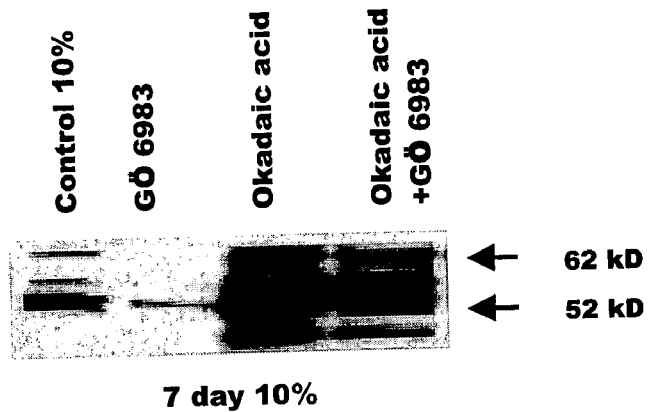

Detection of vimentin in the supernatant was almost completely blocked using the PKC inhibitor GÖ6983 (FIGS. 3c and 4a-b). However, this agent does not modify the amount of actin detected in the supernatants, further indicating that the presence of vimentin in the extracellular fraction is a consequence of an active process of secretion (FIG. 3c).

Since vimentin was often detected in Western blot analysis as multiple bands in the 52-62 kD range, the specificity of the monoclonal antibody that was used in these experiments was confirmed. A polyclonal goat anti-vimentin antibody (FIG. 3c, bottom panel) showed the same pattern of reactivity as the monoclonal antibody when 12 day MDM cell and supernatant were analyzed (FIG. 3c, lanes 1 and 2). Moreover, the same polyclonal antibody displayed no reactivity against cell lysates of peritoneal macrophages isolated from vimentin knock-out mice[4] (FIG. 3c, bottom panel, lane 5). As specified by the manufacturer, the monoclonal anti-vimentin antibody does not recognize mouse vimentin (FIG. 3c, top panel, lanes 5 and 6). In addition, vimentin was not detected in serum-free tissue culture medium prior to MDM culture with either antibody (FIG. 3c, lane 4). Taken together, these findings further confirm the specificity of the antibodies used in these studies.

Figure 3E:
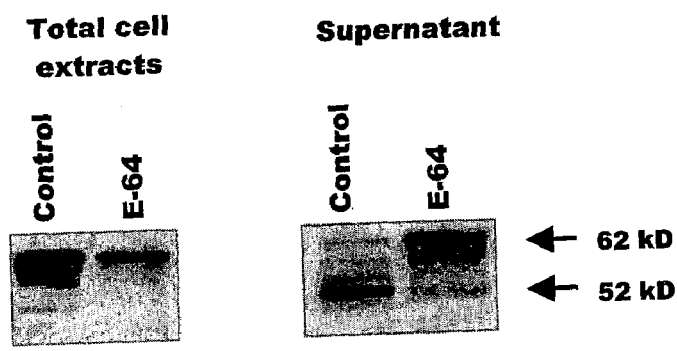

Intermediate filaments are highly sensitive to degradation by $Ca^{2+}$-activated, neutral thiol proteinases like calpain II and thrombin[15-17]. In order to confirm that the presence of more than one vimentin band results from proteolysis, 12 day MDM were treated with the cysteine proteinase inhibitor E-64, and a marked decrease of these proteolytic products both intracellularly and in the supernatant was observed (FIG. 3e). Therefore, the presence of several forms of vimentin is due largely to proteolysis.

EXAMPLE 3

Vimentin Secretion is Dependent Upon Cellular Activation

Because phosphorylation of vimentin plays a key role in its dynamic rearrangement, the contribution of kinase pathways to vimentin secretion was investigated. FIG. 4a shows that enhancement of kinase activity by protein phosphatase blockade using okadaic acid (OA) led to an increase in extracellular vimentin levels (compare lanes 1 and 4). Since the secretion of vimentin from cells treated with 40% human serum is already high, the effect of OA on 7 day MDM treated with 10% serum was assessed, and >10 fold increase in vimentin secretion was observed (FIG. 4b, compare lanes 1 and 3). Vimentin is phosphorylated by a number of protein kinases, including PKC[22,23], which has been implicated in the differentiation of promyeloid HL-60 cells. Therefore, mature MDM were treated with the specific PKC inhibitor GÖ6983. Western blotting revealed that vimentin secretion was significantly blocked in cells treated for 2 h with the PKC blocker (FIGS. 4a and 4b, compare lanes 1 and 2 in each panel). On the other hand, the p38 mitogen-activated protein kinase specific inhibitor SB203580 did not block secretion (FIG. 4a, lane 3). Enhancement of vimentin secretion by the broadly active phosphatase inhibitor OA (FIG. 4b, lane 3) can also be partially decreased by GÖ6983 (FIG. 4b, compare lanes 3 and 4), further supporting a role for PKC activity in this process.

Figure 4C:
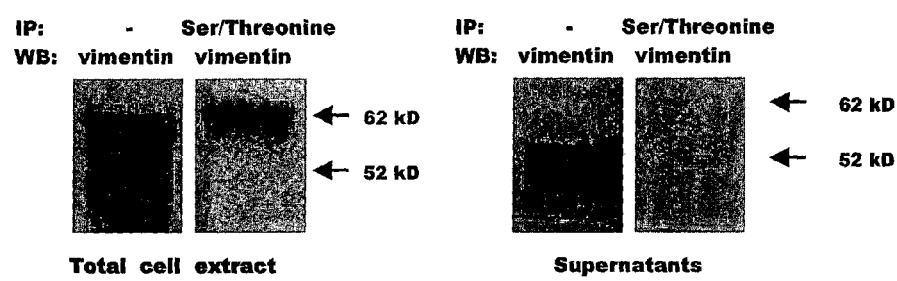
Figure 4D:
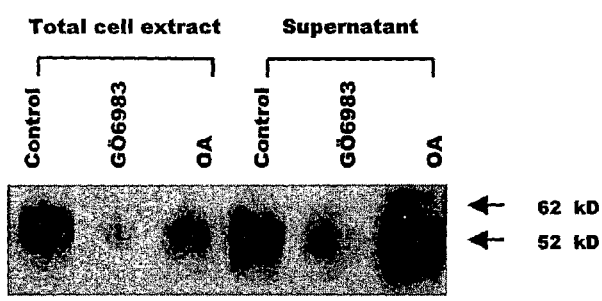

PKC phosphorylates vimentin in vitro and the PKC pathway directly phosphorylates vimentin in vivo[24]. To determine if the secreted vimentin is indeed phosphorylated, an antibody specific for phosphorylated serine and threonine residues was used to immunoprecipitate proteins from both the cytoplasm and supernatant of activated MDM. Phosphorylated vimentin was detected in the immunoprecipitate from both the cellular extract and the supernatant using anti-vimentin monoclonal antibody (FIG. 4c). In addition, the specific PKC inhibitor GÖ6983 markedly decreased the amount of phosphorylated vimentin in the cytoplasm as well as in the supernatant (FIG. 4d, lanes 2 and 5), demonstrating that the PKC pathway mediates the majority of the phosphorylation of vimentin which takes place in MDM. Further, as treatment with OA results in an increase in phosphorylated vimentin in the supernatants but not in the cells (FIG. 4d, compare lanes 3 and 6), these findings indicate that phosphorylation of vimentin enhances its secretion.

In order to further elucidate the phosphorylation pattern of the secreted vimentin, [$^{32}$P] orthophosphate was incorporated in 12 day MDM in the presence or absence of GÖ46983 or OA. These studies demonstrated phosphorylation of the two major forms of vimentin in the intracellular and supernatant fractions (FIG. 4e, lanes 3 and 6). The lower form (52 kD) in the supernatant is more markedly phoshophorylated than the corresponding intracellular form, which can be seen by comparing the autoradiograph to the Western blots shown below (FIG. 4e). Further, phosphorylation of serine/threonine residues with OA preferentially enhances secretion of the 52 kD form, in agreement with what is shown in FIG. 4d. The PKC blocker GÖ6983 again eliminated essentially all the secretion of vimentin, although this was seen only by Western blot due to the lower sensitivity of the direct labeling assay. Taken together, the findings indicate a mechanism by which activation of PKC causes direct phosphorylation of vimentin at serine/threonine residues, thus marking the protein for the secretory pathway. PKC and other kinase pathways might also play an indirect role in vimentin secretion, as is discussed further below.

Figure 5:
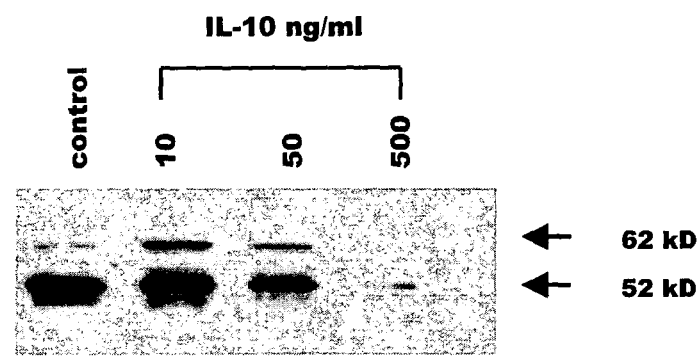
FIG. 5 shows that IL-10 inhibits, while TNF-α increases, secretion of vimentin from monocytes. (a) Eleven day MDM, grown in 40% human serum, were incubated for 12 h with 10, 50, or 500 ng ml$^{-1}$ of IL-10, and secreted vimentin detected by Western blot as above. (b) Peripheral blood monocytes were maintained in 10% human serum for 1 day and incubated for 12 h with medium only or 0.5, 1, or 5 ng ml$^{-1}$ TNF-α, (lanes 1, 2, 3 and 4, respectively). Secreted vimentin was detected in the supernatant as in (a). (c) Densitometric quantitation of the experiment shown in (b).
Figure 5:
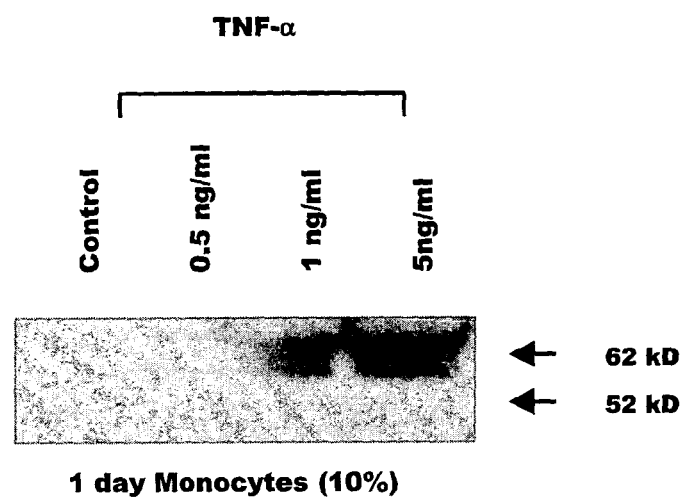
Figure 5:
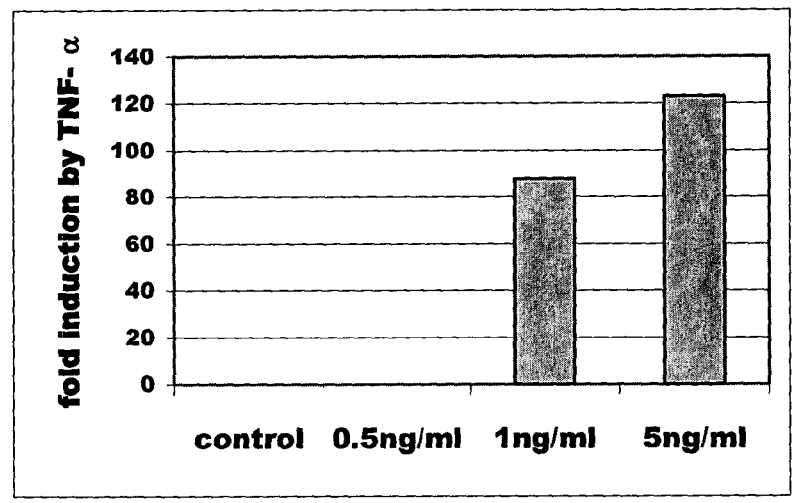

The anti-inflammatory cytokine IL-10, a potent inhibitor of activated macrophages, exerts its effect by inhibiting the PKC pathway[25,26]. Consistent with these findings, IL-10 markedly decreased the secretion of vimentin as shown by Western blot of the supernatants of 12 day MDM (FIG. 5a). Since this physiological anti-inflammatory signal blocks vimentin secretion, we asked whether known pro-inflammatory stimulators could enhance this process. TNF-α is a well-characterized cytokine that is known to act in opposition to IL-10 in macrophages[27]. In FIGS. 5b and 5c we show that very low doses of TNF-α can induce the secretion of vimentin up to 120 fold by 1 day human monocytes maintained in 10% human serum. In currently accepted models of the TNF-α pathway, signaling does not occur through PKC. Consistent with this theory, the secretion of vimentin from 40% treated MDM was not blocked by GÖ6983 in the presence of TNF-α. Thus, both the PKC and TNF-α activation pathways mediate the secretion of vimentin by MDM.

EXAMPLE 4

Antibodies to Vimentin Decrease Superoxide Production and Bacterial Killing by Mature MDM In vitro Experiments were conducted to address whether vimentin affects the inflammatory response of MDM in vitro. When phagocytic monocytes interact with particulate agents, or are stimulated with PMA, the cells respond by activating oxidative metabolism, with a respiratory burst that generates hydrogen peroxide and superoxide anion. These metabolites constitute part of the host defense system against invading microorganisms 28. Therefore, the role of extracellular vimentin in the inflammatory response was investigated by adding anti-vimentin antibody to mature 12 day MDM and then measuring their ability to generate oxidative metabolites in response to PMA. These experiments showed that anti-vimentin antibodies reduced the oxidative burst of these cells when compared to control antibody-treated cells (FIG. 6a).

This result indicates that extracellular vimentin is involved in the response to pathogens. In order to evaluate the effect of vimentin upon the phagocytosis of bacteria, activated MDM were exposed to Escherichia coli (E. coli) in the presence of anti-vimentin or control antibody, and internalized bacteria were harvested from macrophages after 1 hour. In this assay, the anti-vimentin antibody had no effect (FIG. 6b). To look at the intracellular component of pathogen processing, the same assay was performed, but with an additional 2 hour incubation between removal of non-phagocytized bacteria and lysis, allowing time for the MDM to kill any internalized bacteria. In keeping with the above observation that anti-vimentin antibodies can inhibit the oxidative burst, the antibodies were able to increase the amount of viable E. coli recovered from the MDM, indicating a reduction in the ability of MDM to kill bacteria (FIG. 6c).

EXAMPLE 5

Macrophages From Vimentin Knockout Mice Produce Increased Superoxide and Nitric Oxide In vitro Experiments conducted during the development of the present invention demonstrate increased superoxide production by peritoneal macrophages from vimentin knockout mice compared to wild-type mice (FIG. 7a). Resident peritoneal macrophages were harvested from mice with total of 8 mice from each group. Cells were incubated with 50 µM luminol and 100 nM PMA for 5 min at 37° C. Light emission was measured by Chemiluminescence Microlumat LB 96 P (EG&G Berthold). The data shown in FIG. 7a are an average of three different experiments. *p value=0.018. FIG. 7b shows increased nitric oxide production by peritoneal macrophages from vimentin knockout mice compared to wild-type mice. Peritoneal macrophages in 10% F.C.S were incubated for 48 h with IFN γ 50 ng/ml and LPS 1000 ng/m. The media were collected and analyzed for the presence of NO by Griess reagent. Four wild-type and five knockout mice were used in these experiments. *p value=0.057.

EXAMPLE 6

Figure 8:
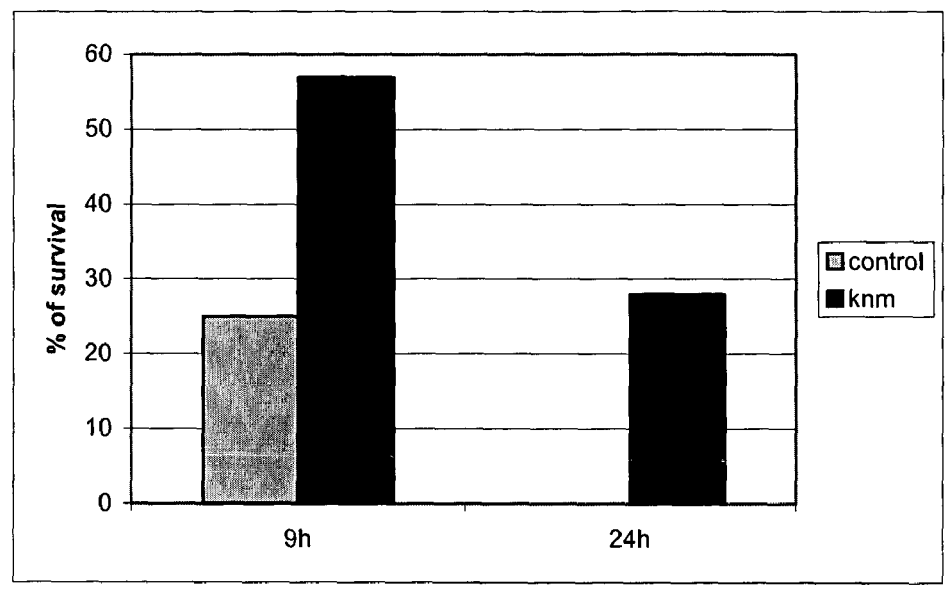
FIG. 8 shows E. coli septicemia and mortality after intraperitoneal bacterial challenge in vimentin knockout mice. (a) shows that when vimentin knockout mice (7 mice) and wild type mice (4 mice) are injected intraperitoneally with a lethal dose of E. coli strain 96 (2×10$^{10}$), over 50% of the knock out mice are alive at 9 hours, and over 25% at 24 hours. By comparison only 25% of the wild-type mice are alive at 9 hours, and none at 24 hours. (b) shows that at three hours after injection, blood from wild-type mice contained 6 log CFU, whereas blood from knock out mice supported less than one log CFU of bacterial growth.
Figure 8:
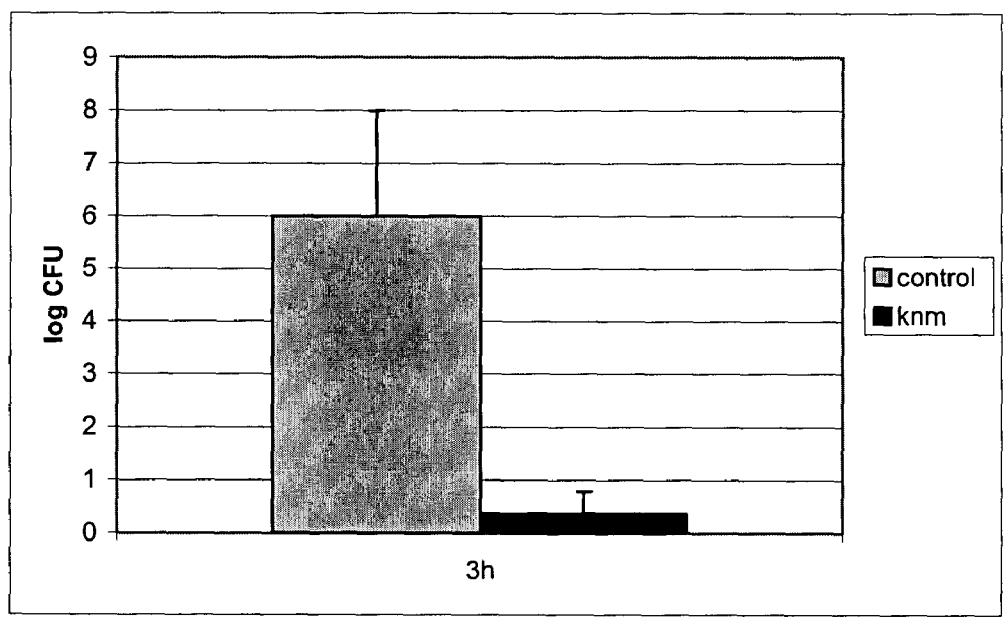

Vimentin Knockout Mice Exhibit Improved Response to E. coli Septicemia and Reduced Mortality In vivo Experiments conducted during the development of the present invention demonstrate reduced E. coli septicemia and mortality after intraperitoneal bacterial challenge in vimentin knockout mice. FIG. 8a shows that when vimentin knockout mice (7 mice) and wild type mice (4 mice) are injected intraperitoneally with a lethal dose of E. coli strain 96 ($2 \times 10^{10}$), over 50% of the knockout mice are alive at 9 hours, and over 25% of the knockout mice are alive at 24 hours. Conversely, only 25% of the wild-type mice are alive at 9 hours, and none at 24 hours. FIG. 8b shows that at three hours after injection, blood from wild-type mice contains 6 log colony-forming units (CFU), whereas blood from knock out mice supported less than one log CFU of bacterial growth.

EXAMPLE 7

Anti-Vimentin Antibodies Protect Mice From Lethal Doses of E. coli. In Vivo

Figure 9:
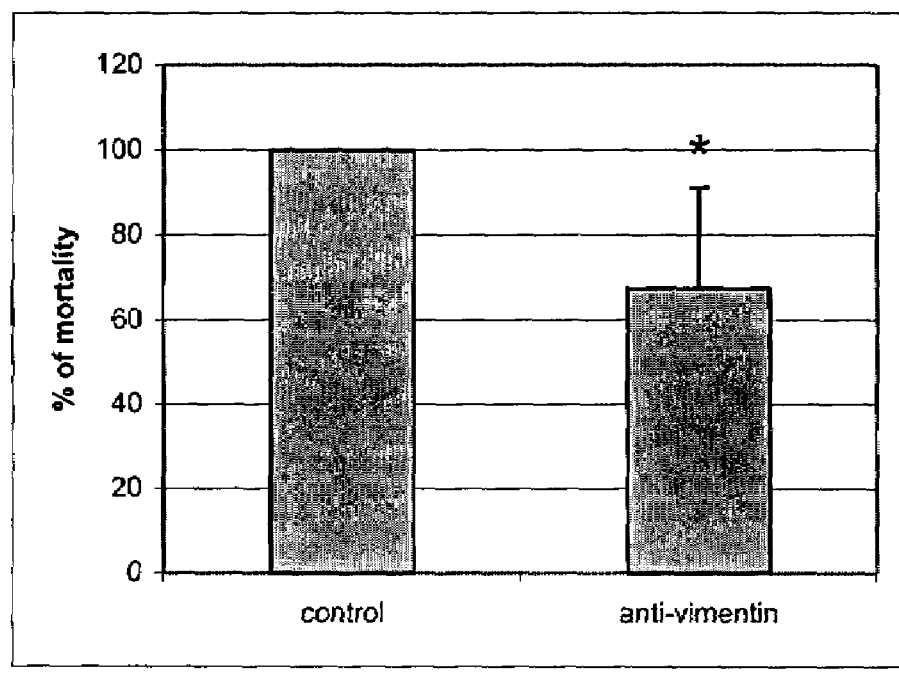
FIG. 9 shows that anti-vimentin antibodies protect mice from intraperitoneal infection with lethal does of E.coli. 13 week old mice were injected I.P. with lethal doses of E. Coli (J-96). Mice died between 3 h to 6 h after infection. Mice were injected I.P. with 150 ul goat serum (control) or 150 ul goat anti-vimentin serum 15 min prior to the E. coli injection. Mice receiving goat anti-vimentin show a 38% reduction in mortality compared to those receiving anti-vimentin antibody free serum. A total of 10 mice in the control group were compared to 11 mice in the anti-vimentin group. *p value=0.035.

Experiments conducted during the development of the present invention demonstrate that anti-vimentin antibodies protect mice from intraperitoneal infection with lethal does of E.coli. 13-week-old mice were injected intraperitoneally with lethal doses of E. Coli (J-96). Mice died between 3 h to 6 h after infection. Control mice were injected intraperitoneally with 150 ul goat serum 15 min prior to the E. coli injection. Treatment mice were injected with 150 ul goat anti-vimentin serum 15 min prior to the E. coli injection. Mice receiving goat anti-vimentin show a 38% reduction in mortality compared to those receiving anti-vimentin antibody free serum (FIG. 9). A total of 10 mice in the control group were compared to 11 mice in the anti-vimentin group. *p value=0.035. These results demonstrate the specific, beneficial effect of anti-vimentin therapy in a well-characterized in vivo model of bacterial sepsis.

All publications and patents mentioned are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in the relevant fields are intended to be within the scope of the following claims.

REFERENCES

1. Traub, P. Intermediate Filaments A Review, (Springer-Verlag, New York, Tokyo, 1985).
2. Fuchs, E. & Weber, K. Intermediate filaments: structure, dynamics, function, and disease. Annu Rev Biochem 63, 345-82 (1994).
3. Christian, J. L., Edelstein, N. G. & Moon, R. T. Overexpression of wild-type and dominant negative mutant vimentin subunits in developing Xenopus embryos. New Biol 2, 700-11. (1990).
4. Colucci-Guyon, E. et al. Mice lacking vimentin develop and reproduce without an obvious phenotype. Cell 79, 679-94. (1994).
5. Eckes, B. et al. Impaired mechanical stability, migration and contractile capacity in vimentin-deficient fibroblasts. J Cell Sci 111, 1897-907 (1998).
6. Galou, M. et al. Disrupted glial fibrillary acidic protein network in astrocytes from vimentin knockout mice. J Cell Biol 133, 853-63. (1996).
7. Eckes, B. et al. Impaired wound healing in embryonic and adult mice lacking vimentin. J Cell Sci 113, 2455-62 (2000).
8. Cain, H., Kraus, B., Krauspe, R., Osborn, M. & Weber, K. Vimentin filaments in peritoneal macrophages at various stages of differentiation and with altered function. Virchows Arch B Cell Pathol Incl Mol Pathol 42, 65-81 (1983).
9. Rius, C., Cabanas, C. & Aller, P. The induction of vimentin gene expression by sodium butyrate in human promonocytic leukemia U937 cells. Exp Cell Res 188, 129-34 (1990).
10. Rius, C. & Aller, P. Vimentin expression as a late event in the in vitro differentiation of human promonocytic cells. J Cell Sci 101, 395-401(1992).
11. Reddy, V. Y., Zhang, Q. Y. & Weiss, S. J. Pericellular mobilization of the tissue-destructive cysteine proteinases, cathepsins B, L, and S, by human monocyte-derived macrophages. Proc Natl Acad Sci USA 92, 3849-53 (1995).

12. Punturieri, A. et al. Regulation of Elastinolytic Cysteine Proteinase Activity in Normal and Cathepsin K-deficient Human Macrophages. *J Exp Med* 192, 789-800 (2000).
13. Cain, H., Krauspe, R. & Kraus, B. The cytoskeleton in activated and in functionally disordered cells of the macrophage system. *Pathol Res Pract* 175, 162-79 (1982).
14. Gao, Y. & Sztul, E. A novel interaction of the Golgi complex with the vimentin intermediate filament cytoskeleton. *J Cell Biol* 152, 877-94. (2001).
15. Traub, P. Large scale isolation, purification, and partial characterization of the intermediate filament-specific, Ca2+-activated proteinase from porcine kidney and Ehrlich ascites tumor cells: a comparative study. *Arch Biochem Biophys* 228, 120-32. (1984).
16. Traub, P., Scherbarth, A., Willingale-Theune, J., Paulin-Levasseur, M. & Shoeman, R. Differential sensitivity of vimentin and nuclear lamins from Ehrlich ascites tumor cells toward Ca2+-activated neutral thiol proteinase. *Eur J Cell Biol* 46, 478-90. (1988).
17. Yoshida, H., Murachi, T. & Tsukahara, I. Degradation of actin and vimentin by calpain II, a Ca2+-dependent cysteine proteinase, in bovine lens. *FEBS Lett* 170, 259-62. (1984).
18. Perides, G., Kuhn, S., Scherbarth, A. & Traub, P. Probing of the structural stability of vimentin and desmin-type intermediate filaments with Ca2+-activated proteinase, thrombin and lysine-specific endoproteinase Lys-C. *Eur J Cell Biol* 43, 450-8. (1987).
19. Tozser, J. et al. Effect of serine and tyrosine phosphorylation on retroviral proteinase substrates. *Eur J Biochem* 265, 423-9. (1999).
20. Ben-Ze'ev, A., Babiss, L. E. & Fisher, P. B. Cleavage of vimentin in dense cell cultures. Inhibition upon transformation by type 5 adenovirus. *Exp Cell Res* 166, 47-62. (1986).
21. Belin, M. T. & Boulanger, P. Processing of vimentin occurs during the early stages of adenovirus infection. *J Virol* 61, 2559-66. (1987).
22. Cheng, T. J. & Lai, Y. K. Identification of mitogen-activated protein kinase-activated protein kinase-2 as a vimentin kinase activated by okadaic acid in 9L rat brain tumor cells. *J Cell Biochem* 71, 169-81. (1998).
23. Turowski, P., Myles, T., Hemmings, B. A., Fernandez, A. & Lamb, N. J. Vimentin dephosphorylation by protein phosphatase 2A is modulated by the targeting subunit B55. *Mol Biol Cell* 10, 1997-2015 (1999).
24. Yasui, Y. et al. Protein kinases required for segregation of vimentin filaments in mitotic process. *Oncogene* 20, 2868-76. (2001).
25. Lo, C. -J., Fu, M. & Cryer, H. G. Interleukin 10 Inhibits Alveolar Macrophage Production of Inflammatory Mediators Involved in Adult Respiratory Distress Syndrome. *Journal of Surgical Research* 79, 179-184 (1998).
26. Bhattacharyya, S., Ghosh, S., Jhonson, P. L., Bhattacharya, S. K. & Majumdar, S. Immunomodulatory Role of Interleukin-10 in Visceral Leishmaniasis: Defective Activation of Protein Kinase C-Mediated Signal Transduction Events. *Infect. Immun.* 69, 1499-1507 (2001).
27. Bogdan, C., Vodovotz, Y. & Nathan, C. Macrophage deactivation by interleukin 10. *J Exp Med* 174, 1549-55. (1991).
28. Schlosser-Silverman, E., Elgrably-Weiss, M., Rosenshine, I., Kohen, R. & Altuvia, S. Characterization of Escherichia coli DNA lesions generated within J774 macrophages. *J Bacteriol* 182, 5225-30 (2000).
29. Klymkowsky, M. W., Bachant, J. B. & Domingo, A. Functions of intermediate filaments. *Cell Motil Cytoskeleton* 14, 309-31 (1989).
30. Lehto, V. P., Hovi, T., Vartio, T., Badley, R. A. & Virtanen, I. Reorganization of cytoskeletal and contractile elements during transition of human monocytes into adherent macrophages. *Lab Invest* 47, 391-9 (1982).
31. Owen, P. J., Johnson, G. D. & Lord, J. M. Protein kinase C-delta associates with vimentin intermediate filaments in differentiated HL60 cells. *Exp Cell Res* 225, 366-73 (1996).
32. Chu, J. J. et al. Taxol induces concomitant hyperphosphorylation and reorganization of vimentin intermediate filaments in 9L rat brain tumor cells. *J Cell Biochem* 68, 472-83. (1998).
33. Szalay, J. et al. Associations of PKC isoforms with the cytoskeleton of B16F10 melanoma cells. *J Histochem Cytochem* 49, 49-66. (2001).
34. Shoeman, R. L. et al. Human immunodeficiency virus type 1 protease cleaves the intermediate filament proteins vimentin, desmin, and glial fibrillary acidic protein. *Proc Natl Acad Sci USA* 87, 6336-40. (1990).
35. Kontny, E., Kurowska, M., Szczepanska, K. & Maslinski, W. Rottlerin, a PKC isozyme-selective inhibitor, affects signaling events and cytokine production in human monocytes. *J Leukoc Biol* 67, 249-58. (2000).
36. Hansson, G. K., Lagerstedt, E., Bengtsson, A. & Heideman, M. IgG binding to cytoskeletal intermediate filaments activates the complement cascade. *Exp Cell Res* 170, 338-50 (1987).
37. Sanchez, A., Ossorio, C., Alvaro-Gracia, J. M., Padilla, R. & Avila, J. A subset of antibodies from the sera of patients with systemic lupus erythematosus react with vimentin and DNA. *J Rheumatol* 17, 205-9 (1990).
38. Senecal, J. L. & Rauch, J. Hybridoma lupus autoantibodies can bind major cytoskeletal filaments in the absence of DNA-binding activity. *Arthritis Rheum* 31, 864-75 (1988).
39. Franch, A., Castellote, C., Vila, J. L., Vilaro, S. & Castell, M. Anticytoskeletal autoantibody development in adjuvant arthritis. *J Rheumatol* 21, 489-97 (1994).
40. Lane, B. R. et al. TNF-alpha inhibits HIV-1 replication in peripheral blood monocytes and alveolar macrophages by inducing the production of RANTES and decreasing C—C chemokine receptor 5 (CCR5) expression. *J Immunol* 163, 3653-61 (1999).
41. Terasaki, M. & Reese, T. S. Characterization of endoplasmic reticulum by co-localization of BiP and dicarbocyanine dyes. *J Cell Sci* 101, 315-22. (1992).
42. Matsukawa, A. et al. Pivotal role of the CC chemokine, macrophage-derived chemokine, in the innate immune response. *J Immunol* 164, 5362-8 (2000).

1TABLE 1 Isolation and Partial Amino Acid Sequence Analysis of Vimentin from the Supernatant of MDM* 1 mstrsvssss yrrmfggpgt asrpsssrsy vttstrtysl gsalrpstsr slyasspggv 61 yatrssavrl rssvpgvrll qdsvdfslad aintefkntr tnekvelqel ndrfanyidk 121 vrfleqqnki llaeleqlkg qgksrlgdly eeemrelrrq vdqltndkar veverdnla 181 dimrlreklq eemlqreeae ntlqsfrqdv dnaslarldl erkveslqee iaflkklhee 241 eiqelqaqiq eqhvqidvdv skpdltaalr dvrqqyesva aknlqeaeew ykskfadls 301 aanrnndalr qakqesteyr rqvqsltcev dalkgtnesl erqmremeen faveaanyqd 361 tigrlqdeiq nmkeemarhl reyqdllnvk maldieiaty rkllegeesr islplpnfss 421 lnlretnlds lplvdthskr tlliktvetr dgqvinetsq hhddle *Amino acid stretches identified as identical to vimentin during protein sequence analysis are underlined. Sequence analysis was performed at the Harvard Microchemistry Facility by microcapillary reverse-phase HPLC nano-electrospray tandem mass spectrometry (.mu.LC/MS/MS) on a Finnigan LCQ quadrupole ion trap mass spectrometer. SEQ ID NO:1 refers to the full length vimentin sequence of amino acids 1 to 466. SEQ ID NO:2 refers to amino acids 105 to 113. SEQ ID NO:3 refers to amino acids 130 to 140. SEQ ID NO:4 refers to amino acids 160 to 170. SEQ ID NO:5 refers to amino acids 295 to 304. SEQ ID NO:6 refers to amino acids 346 to 373. SEQ ID NO:7 refers to amino acids 411 to 420. SEQ ID NO:8 refers to amino acids 425 to 440.

---

What is claimed is:

1. A method for reducing the risk of mortality associated with a pathogen in a subject, comprising:
   a) providing:
      i) a subject having said pathogen; and
      ii) an anti-vimentin antibody that binds to vimentin and inhibits vimentin activity; and
   b) administering said anti-vimentin antibody to said subject having said pathogen under conditions such that said administering reduces the risk of mortality associated with said pathogen.

2. The method of claim 1, wherein said pathogen is a bacterial pathogen.

3. The method of claim 1, wherein said anti-vimentin antibody comprises a monoclonal antibody.

4. The method of claim 1, wherein said anti-vimentin antibody comprises a polyclonal antibody.

5. The method of claim 1, wherein said subject is a human subject.

6. The method of claim 1, wherein said antibody is a humanized antibody.

7. The method of claim 1, wherein said administration is parenteral administration.

8. The method of claim 1, wherein said subject having said pathogen has sepsis.

9. The method of claim 2, wherein said bacterial pathogen is *E. coli*.

* * * * *

SEQUENCE LISTING

<160> NUMBER OF SEQ ID NOS: 8

<210> SEQ ID NO 1
<211> LENGTH: 466
<212> TYPE: PRT
<213> ORGANISM: Homo sapiens

<400> SEQUENCE: 1

```
Met Ser Thr Arg Ser Val Ser Ser Ser Tyr Arg Arg Met Phe Gly
1               5                   10                  15

Gly Pro Gly Thr Ala Ser Arg Pro Ser Ser Ser Arg Ser Tyr Val Thr
                20                  25                  30

Thr Ser Thr Arg Thr Tyr Ser Leu Gly Ser Ala Leu Arg Pro Ser Thr
                35                  40                  45

Ser Arg Ser Leu Tyr Ala Ser Ser Pro Gly Gly Val Tyr Ala Thr Arg
        50                  55                  60

Ser Ser Ala Val Arg Leu Arg Ser Ser Val Pro Gly Val Arg Leu Leu
65                  70                  75                  80

Gln Asp Ser Val Asp Phe Ser Leu Ala Asp Ala Ile Asn Thr Glu Phe
                85                  90                  95

Lys Asn Thr Arg Thr Asn Glu Lys Val Glu Leu Gln Glu Leu Asn Asp
                100                 105                 110

Arg Phe Ala Asn Tyr Ile Asp Lys Val Arg Phe Leu Glu Gln Gln Asn
                115                 120                 125

Lys Ile Leu Leu Ala Glu Leu Glu Gln Leu Lys Gly Gln Gly Lys Ser
        130                 135                 140

Arg Leu Gly Asp Leu Tyr Glu Glu Glu Met Arg Glu Leu Arg Arg Gln
145                 150                 155                 160

Val Asp Gln Leu Thr Asn Asp Lys Ala Arg Val Glu Val Glu Arg Asp
                165                 170                 175

Asn Leu Ala Glu Asp Ile Met Arg Leu Arg Glu Lys Leu Gln Glu Glu
                180                 185                 190

Met Leu Gln Arg Glu Glu Ala Glu Asn Thr Leu Gln Ser Phe Arg Gln
        195                 200                 205

Asp Val Asp Asn Ala Ser Leu Ala Arg Leu Asp Leu Glu Arg Lys Val
        210                 215                 220

Glu Ser Leu Gln Glu Glu Ile Ala Phe Leu Lys Lys Leu His Glu Glu
225                 230                 235                 240

Glu Ile Gln Glu Leu Gln Ala Gln Ile Gln Glu Gln His Val Gln Ile
                245                 250                 255

Asp Val Asp Val Ser Lys Pro Asp Leu Thr Ala Ala Leu Arg Asp Val
                260                 265                 270

Arg Gln Gln Tyr Glu Ser Val Ala Ala Lys Asn Leu Gln Glu Ala Glu
        275                 280                 285

Glu Trp Tyr Lys Ser Lys Phe Ala Asp Leu Ser Glu Ala Ala Asn Arg
        290                 295                 300

Asn Asn Asp Ala Leu Arg Gln Ala Lys Gln Glu Ser Thr Glu Tyr Arg
305                 310                 315                 320

Arg Gln Val Gln Ser Leu Thr Cys Glu Val Asp Ala Leu Lys Gly Thr
                325                 330                 335
```

-continued

```
Asn Glu Ser Leu Glu Arg Gln Met Arg Glu Met Glu Glu Asn Phe Ala
            340                 345                 350

Val Glu Ala Ala Asn Tyr Gln Asp Thr Ile Gly Arg Leu Gln Asp Glu
        355                 360                 365

Ile Gln Asn Met Lys Glu Met Ala Arg His Leu Arg Glu Tyr Gln
    370                 375                 380

Asp Leu Leu Asn Val Lys Met Ala Leu Asp Ile Glu Ile Ala Thr Tyr
385                 390                 395                 400

Arg Lys Leu Leu Glu Gly Glu Ser Arg Ile Ser Leu Pro Leu Pro
                405                 410                 415

Asn Phe Ser Ser Leu Asn Leu Arg Glu Thr Asn Leu Asp Ser Leu Pro
                420                 425                 430

Leu Val Asp Thr His Ser Lys Arg Thr Leu Leu Ile Lys Thr Val Glu
            435                 440                 445

Thr Arg Asp Gly Gln Val Ile Asn Glu Thr Ser Gln His His Asp Asp
    450                 455                 460

Leu Glu
465

<210> SEQ ID NO 2
<211> LENGTH: 9
<212> TYPE: PRT
<213> ORGANISM: Homo sapiens

<400> SEQUENCE: 2

Val Glu Leu Gln Glu Leu Asn Asp Arg
1               5

<210> SEQ ID NO 3
<211> LENGTH: 11
<212> TYPE: PRT
<213> ORGANISM: Homo sapiens

<400> SEQUENCE: 3

Ile Leu Leu Ala Glu Leu Glu Gln Leu Lys Gly
1               5                   10

<210> SEQ ID NO 4
<211> LENGTH: 11
<212> TYPE: PRT
<213> ORGANISM: Homo sapiens

<400> SEQUENCE: 4

Gln Val Asp Gln Leu Thr Asn Asp Lys Ala Arg
1               5                   10

<210> SEQ ID NO 5
<211> LENGTH: 10
<212> TYPE: PRT
<213> ORGANISM: Homo sapiens

<400> SEQUENCE: 5

Phe Ala Asp Leu Ser Glu Ala Ala Asn Arg
1               5                   10

<210> SEQ ID NO 6
<211> LENGTH: 28
<212> TYPE: PRT
<213> ORGANISM: Homo sapiens

<400> SEQUENCE: 6
```

```
-continued

Glu Met Glu Glu Asn Phe Ala Val Glu Ala Ala Asn Tyr Gln Asp Thr
1               5                   10                  15

Ile Gly Arg Leu Gln Asp Glu Ile Gln Asn Met Lys
            20                  25

<210> SEQ ID NO 7
<211> LENGTH: 10
<212> TYPE: PRT
<213> ORGANISM: Homo sapiens

<400> SEQUENCE: 7

Ile Ser Leu Pro Leu Pro Asn Phe Ser Ser
1               5                   10

<210> SEQ ID NO 8
<211> LENGTH: 16
<212> TYPE: PRT
<213> ORGANISM: Homo sapiens

<400> SEQUENCE: 8

Glu Thr Asn Leu Asp Ser Leu Pro Leu Val Asp Thr His Ser Lys Arg
1               5                   10                  15
```